United States Patent
Foehr et al.

(10) Patent No.: US 9,557,340 B2
(45) Date of Patent: Jan. 31, 2017

(54) ASSAYS FOR DETECTION OF PHENYLALANINE AMMONIA-LYASE AND ANTIBODIES TO PHENYLALANINE AMMONIA-LYASE

(71) Applicant: BioMarin Pharmaceutical Inc., Novato, CA (US)

(72) Inventors: Erik Damien Foehr, San Rafael, CA (US); Bin Zhao, San Ramon, CA (US); Carlos Fabricio Santamaria, San Francisco, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 0 days.

(21) Appl. No.: 14/741,339

(22) Filed: Jun. 16, 2015

(65) Prior Publication Data

US 2016/0139144 A1 May 19, 2016

Related U.S. Application Data

(63) Continuation of application No. 13/056,606, filed as application No. PCT/US2009/004386 on Jul. 30, 2009, now abandoned.

(60) Provisional application No. 61/084,961, filed on Jul. 30, 2008.

(51) Int. Cl.
*G01N 33/68* (2006.01)
*G01N 33/573* (2006.01)

(52) U.S. Cl.
CPC ........ *G01N 33/6854* (2013.01); *G01N 33/573* (2013.01); *G01N 2333/988* (2013.01)

(58) Field of Classification Search
None
See application file for complete search history.

(56) References Cited

U.S. PATENT DOCUMENTS

| | | |
|---|---|---|
| 4,252,822 A | 2/1981 | Berry |
| 4,562,151 A | 12/1985 | Kishore |
| 5,166,322 A | 11/1992 | Shaw et al. |
| 5,206,344 A | 4/1993 | Katre et al. |
| 5,466,781 A | 11/1995 | Dorin et al. |
| 5,690,929 A | 11/1997 | Lishko et al. |
| 5,753,487 A | 5/1998 | Eigtved et al. |
| 5,766,897 A | 6/1998 | Braxton |
| 5,981,239 A | 11/1999 | Liu |
| 6,057,292 A | 5/2000 | Cunningham et al. |
| 6,312,939 B1 | 11/2001 | Roberts et al. |
| 6,433,148 B1 | 8/2002 | Abrahan et al. |
| 6,451,986 B1 | 9/2002 | Pettit |
| 6,461,849 B1 | 10/2002 | Olsen et al. |
| 6,548,644 B1 | 4/2003 | Pettit |
| 6,586,398 B1 | 7/2003 | Kinstler et al. |
| 6,596,849 B1 | 7/2003 | Roffler et al. |
| 6,617,118 B2 | 9/2003 | Roffler et al. |
| 6,686,164 B1 | 2/2004 | Olsen et al. |
| 6,737,259 B1 | 5/2004 | Clark |
| 6,939,541 B2 | 9/2005 | Roberts et al. |
| 6,939,941 B2 | 9/2005 | Gilmore et al. |
| 6,967,097 B2 | 11/2005 | Yoshida et al. |
| 7,531,341 B1 | 5/2009 | Vellard et al. |
| 7,534,595 B2 | 5/2009 | Vellard et al. |
| 7,537,923 B2 | 5/2009 | Kakkis et al. |
| 7,553,653 B2 | 6/2009 | Gamez et al. |
| 7,560,263 B2 | 7/2009 | Kakkis et al. |
| 7,790,433 B2 | 9/2010 | Kakkis et al. |
| 8,114,958 B2 | 2/2012 | Soares et al. |
| 8,263,415 B2 | 9/2012 | Berling et al. |
| 2003/0082238 A1 | 5/2003 | Babich et al. |
| 2004/0126358 A1 | 7/2004 | Warne et al. |
| 2005/0163708 A1 | 7/2005 | Robinson et al. |
| 2008/0008695 A1 | 1/2008 | Vellard et al. |
| 2008/0064856 A1 | 3/2008 | Warne et al. |
| 2009/0038023 A1 | 2/2009 | Weiner et al. |
| 2011/0201022 A1 | 8/2011 | Foehr et al. |

FOREIGN PATENT DOCUMENTS

| | | |
|---|---|---|
| EP | 0 167 411 A2 | 1/1986 |
| TW | 200902052 | 1/2009 |
| WO | WO 90/12874 | 11/1990 |
| WO | WO 02/094853 | 11/2002 |
| WO | WO 03/018759 | 3/2003 |
| WO | WO 03/072743 | 9/2003 |
| WO | WO 2004/044169 | 5/2004 |
| WO | WO 2006/034373 | 3/2006 |
| WO | WO 2006/099207 | 9/2006 |

(Continued)

OTHER PUBLICATIONS

Ponce, Elvira, Jay Moskovitz, and Gregory Grabowski. "Enzyme therapy in Gaucher disease type 1: effect of neutralizing antibodies to acid β-glucosidase." Blood 90.1 (1997): 43-48.*
U.S. Appl. No. 61/301,478, filed Feb. 4, 2010, Zecherle et al.
Abell et al., "An In Vivo Evaluation of the Chemotherapeutic Potency of Phenylalanine Ammonia-Lyase," *Cancer Research*, 33:2529-2532 (1973).
Abell et al., "Phenylalanine Ammonia-Lyase from the Yeast *Rhodotorula Glutinis,*" *Methods in Enzymology*, 142:242-253 (1987).
Abell et al., "The Effects of Phenylalanine Ammonia-Lyase on Leukemic Lymphocytes in Vitro," *Cancer Research*, 32:285-290 (1972).
Abrams et al., "Rational Antigen Modification as a Strategy to Upregulate or Downregulate Antigen Recognition," *Current Opinion Immunology*, 12:85-91 (2000).
Alunni et al., "Mechanisms of Inhibition of Phenylalanine Ammonia-Lyase by Phenol Inhibitors and Phenol/Glycine Synergistic Inhibitors," *Archives of Biochemistry and Biophysics*, 412:170-175 (2003).

(Continued)

*Primary Examiner* — Robert Yamasaki
(74) *Attorney, Agent, or Firm* — Jones Day

(57) ABSTRACT

Provided herein are methods of detecting the presence of a pegylated enzyme, an enzyme-specific antibody (e.g., a neutralizing antibody or of a particular isotype), or a polyethylene glycol (PEG)-specific antibody in a sample, such as a bodily fluid or tissue of a patient. In certain embodiments, the enzyme is phenylalanine ammonia-lyase (PAL), such as *Anabaena variabilis* (Av) PAL administered to the patient as part of an enzyme substitution therapy for diseases or disorders, such as phenylketonuria (PKU), or cancer therapy.

14 Claims, 22 Drawing Sheets

(56) References Cited

FOREIGN PATENT DOCUMENTS

| WO | WO 2008/069958 | 6/2008 |
|----|----------------|--------|
| WO | WO 2008/153776 | 12/2008 |
| WO | WO 2009/025760 | 2/2009 |
| WO | WO 2010/014225 | 2/2010 |
| WO | WO 2011/097335 | 8/2011 |

OTHER PUBLICATIONS

Ambrus et al., "Depletion of Phenylalanine in the Blood of Phenylketonuric Patients Using a PAL-Enzyme Reactor, an In Vitro Study," *Research Communications in Chemical Pathology and Pharmacology*, 37(1):105-111 (1982).
Ambrus et al., "Extracorporeal Enzyme Reactors for Depletion of Phenylalanine in Phenylketonuria," *Annals of Internal Medicine*, 106:531-537 (1987).
Ambrus et al., "In Vivo Safety of Hollow Fiber Enzyme-Reactors with Immobilized Phenylalanine Ammonia-Lyase in a Large Animal Model for Phenylketonuria," *The Journal of Pharmacology and Experimental Therapeutics*, 224(3):598-602 (1983).
Ambrus et al., "Phenylalanine Depletion for the Management of Phenylketonuria: Use of Enzyme Reactors with Immobilized Enzymes," *Science*, 201:837-839 (1978).
Anson J. G., "Complete Nucleotide Sequence of the Rhodosporidium Toroloides Gene Coding for Phenylalanine Ammonia-lyase," *Gene* 58:189-199 (1987).
Ao et al., "Fluoroimmunoassay for Antigen Based on Fluorescence Quenching Signal of Gold Nanoparticles," *Anal. Chem.*, 78(4):1104-1106 (2006).
Baedeker et al., "Structures of two Histidine Ammonia-Lyase Modifications and Implications for the Catalytic Mechanism," *European Journal of Biochemistry*, 269:1790-1797 (2002).
Becker et al., "Cloning, Sequencing, and Biochemical Characterization of the Nostocyclopeptide Biosynthetic Gene Cluster: Molecular Basis for Imine Macrocyclization," *Gene*, 325:35-42 (2004).
Bezanson et al., "Biosynthesis of Cinnamamide and Detection of Phenylalanine Ammonia-Lyase in *Streptomyces Verticillatus*," *Canadian Journal of Microbiology*, 16:147-151 (1970).
Billett et al., "A Specific and Reversible Macromolecular Inhibitor of Phenylalanine Ammonia-Lyase and Cinnamic Acid-4-Hydroxylase in Gherkins," *Biochim. Biophys. Acta.*, 524:219-230 (1978).
Bourget et al., "Artificial Cell-Microencapsulated Phenylalanine Ammonia-Lyase," *Applied Biochemistry and Biotechnology*, 10:57-59 (1984).
Bourget et al., "Phenylalanine Ammonia-Lyase Immobilized in Semipermeable Microcapsules for Enzyme Replacement in Phenylketonuria," *Federation of European Biochemical Societies Letters*, 180(1):5-8 (1985).
Bourget et al., "Phenylalanine Ammonica-Lyase Immobilized in Microcapsules for the Depletion of Phenylalanine in Plasma in Phenylketonuric Rat Model," *Biochimica et Biophysica Acta*, 883:432-438 (1986).
Brannigan et al., "Protein Engineering 20 Years on," *Nature Reviews, Molecular Cell Biology*, 3:964-970 (2002).
Calabrese et al., "Crystal Structure of Phenylalanine Ammonia-Lyase: Multiple Helix Dipoles Implicated in Catalysis," *Biochemistry*, 43(36):11403-11416 (2004).
Caliceti et al., "Pharmacokinetic and biodistribution properties of poly(ethylene glycol)-protein conjugates," *Adv. Drug Deliv. Rev.*, 55(10):1261-1277 (2003).
Chang et al., "A New Theory of Enterorecirculation of Amino Acids and its Use for Depleting Unwanted Amino Acids Using Oral Enzyme-Artificial Cells, as in Removing Phenylalanine in Phenylketonuria," *Art. Cells Blood Subs. And Immob. Biotech.*, 23(1):1-21 (1995).
Chang et al., "Procedures for Microencapsulation of Enzymes, Cells and Genetically Engineered Microorganisms," *Molecular Biotechnology*, 17:249-260 (2001).

Chen et al., "Tuning the Activity of an Enzyme for Unusual Environments: Sequential Random Mutagenesis of Subtilisin E for Catalysis in Dimethylformamide," *Proc. Natl. Acad. Sci. U.S.A.*, 90:5618-5622 (1993).
Cheng et al., "Accelerated Clearance of Polyethylene Glycol-Modified Proteins by Anti-Polyethylene Glycol IgM," *Bioconjugate Chem.* 10:520-528 (1999).
Cheng et al., "Efficient Clearance of Poly(ethylene glycol)-Modified Immunoenzyme with Anti-PEG Monoclonal Antibody for Prodrug Cancer Therapy," *Bioconjugate Chem.* 11:258-266 (2000).
Chi et al., "Physical Stability of Proteins in Aqueous Solution: Mechanism and Driving Forces in Nonnative Protein Aggregation," *Pharmaceutical Research*, 21(6):1325-1336 (2003).
Chirino et al., "Minimizing the Immunogenicity of Protein Therapeutics," *Drug Discovery Today*, 9(2):82-90 (2004).
Christiansen et al., "The Role of the MoFe protein alpha-125-Phe and beta-125-Phe Residues in *Azotobacter Vinelandii* MoFe-Fe Protein Interaction," *Journal of Inorganic Biochemistry*, 80:195-204 (2000).
Cui et al., "Synthesis of $Ag_{core}Au_{shell}$ Bimetallic Nanoparticles for Immunoassay Based on Surface-Enhanced Raman Spectroscopy," *J. Phys. Chem. B*, 110(9):4002-4006 (2006).
D'Agostino, "Tetrahydrobiopterin and Mild Phenylketonuria," *New England Journal of Medicine*, 348:1723-1724 (2003).
Da Cunha, "Purification, Characterization and Induction of L-Phenylalanine Ammonia-Lyase in *Phaseolus Vulgaris*," *European Journal of Biochemistry*, 178:243-248 (1988).
Dai et al., "Electrochemical Sensor for Immunoassay of Carcinoembryonic Antigen Based on Thionine Monolayer Modified Gold Electrode," *Cancer Detection and Prevention*, 29:233-240 (2005).
Database NCBI, Accession No. ABA23953, Sep. 15, 2005.
Database NCBI, Accession No. CAA31209, Mar. 23, 1993.
Database NCBI, Accession No. X51513, Nov. 28, 1996, the whole sequence.
Davis, "Mimicking Posttranslational Modifications of Proteins," *Science*, 303:480-482 (2004).
Delgado et al., "The Uses and Properties of PEG-Linked Proteins," *Critical Reviews in Therapeutic Drug Carrier Systems*, 9(3-4):249-304 (1992).
Dengler, et al., "Development of a Propidium Iodide Fluorescence Assay for Proliferation and Cytotoxicity Assays," *Anti-Cancer Drugs*, 6:522-532 (1995).
Dermer (1994) "Another anniversary for the war on cancer" *Bio/Technology* 12:320.
Egrie et al., "Development and Characterization of Novel Erythropoiesis Stimulating Protein (NESP)," *British Journal of Cancer*, 84(Suppl. 1):3-10 (2001).
Elstad et al., "Modulation of B16-B16 Murine Melanoma Metastatic Phenotype by Tyrosine and Phenylalanine Restriction in the Absence of Host Selection Pressures," *Anticancer Research*, 13:523-528 (1993).
Elstad et al., "Tyrosine and Phenylalanine Restriction Sensitizes Adriamycin-Resistant P388 Leukemia Cells to Adriamycin," *Nutrition and Cancer*, 25:47-60 (1996).
Evans et al., "Bioconversion of Trans-Cinnamic Acid to L-Phenylalanine in an Immobilized Whole Cell Reactor," *Biotech. Bioeng.* 30:1067-1072 (1987).
Faulkner et al., "High-level Expression of the Phenylalanine Ammonia-lyase-encoding Gene from Rhodosporidium Toruloides in *Saccharomyces cerevisiae* and *Escherichia coli* using a Bifunctional Expression System," *Gene* 143:13-20 (1994).
Filpula et al., "Nucleotide Sequence of Gene for Phenylalanine Ammonia-lyase from Rhodotorula Rubra," *Nucleic Acids Res.* 16:11381 (1988).
Foehr (2009) "Development and Validation of an Assay to Detect Activity Neutralizing Antibodies (Nab assay) to rAvPAL-PEG" *2009 AAPS National Biotechnology Conference*. Available at : http://abstracts.aapspharmaceutica.com/ExpoNBC09/CC/forms/attendee/index.aspx?content=sessionInfo&sessionId=272 (last visited Jun. 27, 2011).
Freshney Culture of Animal Cells: A Manual of Basic Technique (Alan R Liss, Inc., New York, NY), pp. 3-4 (1983).

(56) References Cited

OTHER PUBLICATIONS

Fritz et al., "Phenylalanine Ammonia-Lyase," *The Journal of Biological Chemistry*, 251(15):4646-4650 (1976).
Fu et al., "Focal Adhesion Kinase-Dependent Apoptosis of Melanoma Induced Tyrosine and Phenylalanine Deficiency," *Cancer Research*, 59:758-765 (1999).
Fu et al., "Inflence of Tyrosine and Phenylalanine Limitation on Cytoxicity of Chimeric TGF-α Toxins on B16BL6 Murine Melanoma in Vitro," *Nutrition and Cancer*, 31(1):1-7 (1998).
Fu et al., "Selective Amino Acid Restriction Targets Mitochondria to Induce Apoptosis of Androgen-Independent Prostate Cancer Cell," *Journal of Cellular Physiology*, 208:522-534 (2006).
Fu et al., "Specific Amino Acid Dependency Regulates Invasiveness and Viability of Androgen-Independent Prostate Cancer Cells," *Nutrition and Cancer*, 45(1):60-73 (2003).
Gamez et al., "Development of Pegylated Forms of Recombinant Rhodosporidium Toruloides Phenylalanine Ammonia-Lyase for the Treatment of Classical Phenylketonuria," *Molecular Theory*, 11(6):986-989 (2005).
Ghindilis, "Direct Electron Transfer Catalysed by Enzymes: Application for Biosensor Development," *Biochemical Society Transactions*, 28(2):84-89 (2000).
Gilbert et al., "Protection of Phenylalanine Ammonia-Lyase from Proteolytic Attack," *Biochemical and Biophysical Research Communications*, 131(2)557-563 (1985).
Gilbert et al., "The Effect of Proteinases on Phenylalanine Ammonia-Lyase from the Yeast Rhodotorula Glutinis," *Biochem. J.*, 199:715-723 (1981).
Goodson et al., "Site-Directed Pegylation of Recombinant Interleukin-2 at its Glycosylation Site," *Biotechnology*, 8:343-346 (1990).
Graham, "Pegaspargase: A Review of Clinical Studies," *Advanced Drug Delivery Reviews*, 55:1293-1302 (2003).
Greenwald et al., "Effective Drug Delivery by PEGylated Drug Conjugates," *Advanced Drug Delivery Reviews*, 55:217-250 (2003).
Gura "Systems for identifying new drugs are often faulty," *Science* 278:1041-1042 (1997).
Harris et al., "Effect of Pegylation on Pharmaceuticals," *Nature Reviews, Drug Discovery*, 2:214-221 (2003).
Hedstrom et al., "Converting Trypsin to Chymotrypsin: The Role of Surface Loops," *Science*, 255(5049):1249-1253 (1992).
Hennig et al., "The influence of naturally occurring heterophilic direct measurement of serum proteins using sandwich ELISAs," *J. Immunol. Methods*. 235(1-2):71-80 (2000).
Hermeling et al., "Structure-Immunogenicity Relationships of Therapeutic Proteins," *Pharmaceutical Research*, 21(6):897-903 (2004).
Hershfield et al., "Use of Site-Directed Mutagenesis to Enhance the Epitope-Shielding Effect of Covalent Modification of Proteins with Polyethylene Glycol," *Proc. Natl. Acad. Sci. USA*, 88:7185-7189 (1991).
Hershfield, Enzyme Replacement Therapy of Adenosine Deaminase Deficiency with Polyethylene Glycol-Modified Adenosine Deaminase (PEG-ADA), *Immunodeficiency*, 4:93-97 (1993).
Hill et al., "Investigation of the Early Steps in Soraphen A Biosynthesis," *Chemical Communications*, 12:1358-1359 (2003).
Hoffmann et al., "Sequence Analysis and Biochemical Characterization of the Nostopeptolide A Biosynthetic Gene Cluster from Nostoc sp. GSV224," *Gene*, 311:171-180 (2003).
Hofmann et al., "Recent Advances in the Application of Expressed Protein Ligation to Protein Engineering," *Current Opinion in Biotechnology*, 13(4):297-303 (2002).
Holden et al., "Chorismate Lyase: Kinetics and Engineering for Stability," *Biochim. Biphys. Acta*, 1594:160-167 (2002).
Hopfner et al., "New Enzyme Lineages by Subdomain Shuffling," *Proc. Natl. Acad. Sci., USA*, 95:9813-9818 (1998).
Hoskins et al., "Enzymatic Control of Phenylalanine Intake in Phenylketonuria," *The Lancet*, 392-394 (Feb. 23, 1980).
Hoskins et al., "Phenylalanine Ammonia Lyase in the Management of Phenylketonuria: The Relationship Between Ingested Cinnamate and Urinary Hippurate in Humans," *Research Communications in Chemical Pathology and Pharmacology*, 35(5):275-282 (1982).
Hoskins et al., "The Metabolism of Cinnamic Acid by Healthy and Phenylketonuric Adults: a Kinetic Study," *Biomedical Mass Spectrometry*, 11(6):296-300 (1984).
Ikeda et al., "Phenylalanine Ammmonia-Lyase Modified with Polyethylene Glycol: Potential Therapeutic Agent for Phenylketonuria," *Amino Acids*, 29(3):283-287 (2005).
International Search Report and Written Opinion for PCT/US2005/033895 (WO2006/034373), Sep. 5, 2006.
International Search Report and Written Opinion for PCT/US2008/006661 (WO2008/153776) dated Nov. 12, 2008.
International Search Report and Written Opinion for PCT/US2009/004386 (WO2010/014225) dated May 3, 2010.
International Search Report and Written Opinion for PCT/US2011/023534 (WO2011/097335) dated Aug. 10, 2011.
Kalaitzis et al., "Mutasynthesis of Enterocin and Wailupemycin Analogues," *Journal of the American Chemical Society*, 125:9290-9291 (2003).
Kalghatgi et al., "Multitubular Reactors with Immobilized L-Phenylalanine Ammonia-Lyase for Use in Extracorporeal Shunts," *Research Communications in Chemical Pathology and Pharmacology*, 27(3):551-561 (1980).
Kaufman, "A Model of Human Phenylalanine Metabolism in Normal Subjects and in Phenylalanine Patients," *Proc. Natl. Acad. Sci. USA*, 96:3160-3164 (1999).
Kerbel, "Human Tumor Xenografts as Predictive Clinical Models of Anticancer Drug Activity in Humans," *Cancer Biology & Therapy*, 2:(4)S134-S139 (2003).
Kim et al., "Trends in Enzyme Therapy for Phenylketonuria," *Molecular Therapy*, 10(2):220-224 (2004).
Kinstler et al., "Characterization and Stability of N-Terminally PEGylated rhG-CSF," *Pharmaceutical Research*, 13(7):996-1002 (1996).
Koch et al., "Large Neutral Amino Acid Therapy and Phenylketonuria: a Promising Approach to Treatment," *Molecular Genetics and Metabolism*, 79:110-113 (2003).
Koukol et al., "The Metabolism of Aromatic Compounds in Higher Plants," *The Journal of Biological Chemistry*, 236(10):2692-2698 (1961).
Kreitman, "Immunotoxins for Targeted Cancer Therapy," *The AAPS Journal*, 8(3):E532-551 (2006).
Kriwacki et al., "Combined Use of Proteases and Mass Spectrometry in Structural Biology," *Journal of Biomolecular Techniques*, 9(3):5-15 (1998).
Kropf et al., "Immunological Measurements of Transforming Growth Factor-Beta I (TGF-βI) in Blood; Assay Development and Comparison," *Clinical Chemistry*, 43(10):1965-1974 (1997).
Kyndt et al., "Characterization of a Bacterial Tyrosine Ammonia Lyase, a Biosynthetic Enzyme for the Photoactive Yellow Protein," *Federation of European Biochemical Societies Letters*, 512:240-244 (2002).
Langer et al., "Identification of Essential Amino Acids in Phenylalanine Ammonia-Lyase by Site-Directed Mutageneisis," *Biochemistry*, 36:10867-10871 (1997).
Langer et al., "Methylidene-Imidazole (MIO) from Histidine and Phenylalanine Ammonia-Lyase," *Advances in Protein Chemistry*, 58:175-188 (2001).
Larue et al., "An Extracorporeal Hollow-Fiber Reactor for Pheylketonuria Using Immobilized Phenylalanine Ammonia Lyase," *Dev. Pharmacol. Ther.*, pp. 9:73-81 (1986).
Lazar et al., "Designing Proteins for Therapeutic Applications," *Current Opinion in Structural Biology*, 13:513-518 (2003).
Lee et al., "N-Terminal Site-Specific Mono-PEGylation of Epidermal Growth Factor," *Pharmaceutical Research*, 20(5):818-825 (2003).
Leong et al., Adapting Pharmacokinetic Properties of a Humanized Anti-Interleukin-8 Antibody for Therapeutic Applications using Site-Directed Pegylation, *Cytokine*, 16:(3):106-119 (2001).
Levy, "Phenylketonuria: Old Disease, New Approach to Treatment," *Proc. Natl. Acad. Sci. USA*, 96:1811-1813 (1999).
Liu et al., "Solid-Substrate Room-Temperature Phosphorescence Immunoassay Based on an Antibody Labeled with Nanopartiles

(56) References Cited

OTHER PUBLICATIONS

Containing Dibromofluorescein Luminescent Molecules and Analytical Application," *Journal of Immunological Methods*, 307:34-40 (2005).
Liu et al., "Study on a Novel Strategy to Treatment of Phenylketonuria," *Art. Cells Blood Subs. Immob. Biotech.*, 30(4):243-257 (2002).
Lu et al., "Pegylation: a Method for Assessing Topological Accessibilities in Kv1.3," *Biochemistry*, 40:13288-13301 (2001).
Lucke et al., "BH4-Sensitive Hypelphenylalaninemia: New Case and Review of Literature," *Pediatric Neurology*, 28(3):228-230 (2003).
Marconi et al., "Phenylalanine Ammonia-Lyase Entrapped in Fibers," *Biochimie*, 62:575-580 (1980).
Marshall et al., "Rational Design and Engineering of Therapeutic Proteins," *Drug Discovery Today*, 8(5):212-221 (2003).
Matalon et al., "Biopterin Responsive Phenylalanine Hydroxylase Deficiency," *Genetics in Medicine*, 6(1):27-32 (2004).
Maverakis et al., Autoreactive T Cells can be Protected from Tolerance Induction Through Competition by Flanking Determinants for Access to Class II MHC, *Proceedings of the National Academy of Sciences USA*, 100(9):5342-5347 (2003).
Meadows et al., "Dietary Influence of Tyrosine and Phenylalanine on the Response of B16 Melanoma to Carbidopa-Levodopa Methyl Ester Chemotherapy," *Cancer Res.*, 42:3056-3063 (1982).
Mehvar, "Modulation of the Pharmacokinetics and Pharmacodynamics of Proteins by Polyethylene Glycol Conjugation," *J. Pharm. Pharmaceut. Sci.*, 3(1):125-136 (2000).
Meyer et al., "Reduced Antibody Response to Streptavidin Through Site-Directed Mutagenesis," *Protein Science*, 10:491-503 (2001).
Mire-Sluis et al., "Recommendations for the Design and Optimization of Immunoassays Used in the Detection of Host Antibodies Against Biotechnology Products," *Journal of Immunological Methods*, 289:1-6 (2004).
Moffitt et al., "Discovery of Two Cyanobacterial Phenylalanine Ammonia Lyases: Kinetic and Structural Characterization," *Biochemistry*, 46:1004-1012 (2007).
Molineux, "Pegylation: Engineering Improved Pharmaceuticals for Enhanced Therapy," *Cancer Treatment Reviews*, 28(Suppl. A):13-16 (2002).
Moola et al.,"*Erwinia Chrysanthemi* L-Aspariginase: Epitope Mapping and Production of Antigenically Modified Enzymes," *Biochemical Journal*, 302:921-927 (1994).
Moore, "Biosynthesis of Marine Natural Products: Microorganisms (Part A)," *Natural Products Reports*, 22:580-593 (2005).
National Institutes of Health, "Phenylketonuria (PKU): Screening and Management," *NIH Consensus Statement*, 17(3):1-33 (2000).
Notice of Allowance for U.S. Appl. No. 11/230,374 (U.S. Pub. No. 2007-0048855) dated Nov. 30, 2007.
Notice of Allowance for U.S. Appl. No. 11/230,374 (U.S. Pub. No. 2007-0048855) dated Jan. 10, 2008.
Notice of Allowance for U.S. Appl. No. 11/451,999 dated Aug. 22, 2008.
Notice of Allowance for U.S. Appl. No. 11/451,999 dated Mar. 10, 2009.
Notice of Allowance for U.S. Appl. No. 11/807,227 (U.S. Pub. No. 2008-0008695) dated Mar. 30, 2009.
Notice of Allowance for U.S. Appl. No. 12/107,731 (U.S. Pub. No. 2009-0047268) dated May 26, 2009.
Notice of Allowance for U.S. Appl. No. 12/107,736 (U.S. Pub. No. 2009-0047265) dated Apr. 1, 2009.
Notice of Allowance for U.S. Appl. No. 12/421,557 (U.S. Pub. No. 2009-0263369) dated Apr. 12, 2010.
Nunez et al., "PPAR-γ Ligands and Amino Acid Deprivation Promote Apoptosis of Melanoma, Prostate, and Breast Cancer Cells," *Cancer Letters*, 236:133-141 (2006).
Office Action (updated) for U.S. Appl. No. 12/107,731 (U.S. Pub. No. 2009-0047268) dated Dec. 22, 2008.
Office Action (updated) for U.S. Appl. No. 12/107,736 (U.S. Pub. No. 2009-0047265) dated Jan. 8, 2009.
Office Action for U.S. Appl. No. 11/230,374 (U.S. Pub. No. 2007-0048855) dated Jun. 15, 2007.
Office Action for U.S. Appl. No. 11/451,999 dated Jun. 4, 2008.
Office Action for U.S. Appl. No. 11/451,999 dated Nov. 30, 2007.
Office Action for U.S. Appl. No. 11/807,227 (U.S. Pub. No. 2008-0008695) dated Jan. 16, 2009.
Owens et al., "The Genetic Engineering of Monoclonal Antibodies," *J. Immunol. Methods* 168:149-165 (1994).
Parkinson et al., "Pegvisomant in the Treatment of Acromegaly," *Advanced Drug Delivery Reviews*, 55:1303-1314 (2003).
Pedersen et al., "Preparation of Immobilized L-Phenylalanine Ammonia-Lyase in Tubular Form for Depletion of L-Phenylalanine," *Research Communications in Chemical Pathology and Pharmacology*, 20(3):559-569 (1978).
Pettit et al., "Structure-Function Studies of Interleukin 15 Using Site-Specific Multigenesis, Polyethylene Glycol Conjugation, and Homology Modeling," *The Journal of Biological Chemistry*, 272(4):2312-2318 (1997).
Pilbak et al., "The Essential Tyrosine-Containing Loop Conformation and the Role of the C-Terminal Multi-Helix Region in Eukaryotic Phenylalanine Ammonia-Lyases," *FEBS Journal*, 273:1004-1019 (2006).
Poppe et al., "Friedel-Crafts-Type Mechanism for the Enzymatic Elimination of Ammonia from Histidine and Phenylalanine," *Angewandte Chemie Int. Ed.*, 44:3668-3688 (2005).
Poppe et al., "Methylidene-Imidazolone: a Novel Electrophile for Substrate Activation," *Current Opinion in Chemical Biology*, 5:512-524 (2001).
Poppe et al., "Properties and Synthetic Applications of Ammonia-Lyases," *Current Organic Chemistry*, 7:1297-1315 (2003).
Rånby et al., "Immunoreactivity of Tissue Plasminogen Activator and of its Inhibitor Complexes," *Thrombosis and Haemostasis*, 61(3):409-414 (1989).
Rao et al., "Degradation of Aromatic Amino Acids by Fungi," *Canadian Journal of Biochemistry*, 45:1863-1872 (1967).
Reddy et al., "Use of Peginterferon alfa-2a (40 KD) (Pegasys®) for the Treatment of Hepatitis C," *Advanced Drug Delivery Reviews*, 54:571-586 (2002).
Roberts et al., "In Vivo Effects of Phenylalanine Ammonia-Lyase," *Cancer Treatment Reports*, 60(3):261-263 (1976).
Rother et al., "An Active Site Homology Model of Phenylalanine Ammonia-Lyase from *Petroselinum crispum,*" *European Journal of Biochemistry*, 269:3065-3075 (2002).
Rother et al., "Characterization of the Active Site of Histidine Ammonia-Lyase from *Pseudomonas putida,*" *European Journal of Biochemistry*, 268:6011-6019 (2001).
Russell et al., "Recombinant Proteins for Genetic Disease," *Clin. Genet.*, 55:389-394 (1999).
Sarkissian et al., "A Different Approach to Treatment of Phenylketonuria: Phenylalanine Degradation with Recombinant Phenylalanine Ammonia Lyase," *Proceedings of the National Academy of Sciences USA*, 96:2339-2344 (1999).
Sarkissian et al., "A Heteroallelic Mutant Mouse Model: A New Orthologue for Human Hyperphenylalaninemia," *Molecular Genetics and Metabolism*, 69:188-194 (2000).
Schellekens, "Factors Influencing the Immunogenicity of Therapeutic Proteins," *Nephrology Dialysis Transplantation*, 20( Suppl. 6):vi3-vi9 (2005).
Schultz et al., "Single-Target Molecule Detection with Nonbleaching Multicolor Optical Immunolabels," *Proceedings of the National Academy of Sciences USA*, 97(3):996-1001 (2000).
Schupbach et al., "Heat-Mediated Immune Complex Dissociation and Enzyme-Linked Immunosorbent Assay Signal Amplification Render P24 Antigen Detection in Plasma as Sensitive as HIV-1 RNA Detection by Polymerase Chain Reaction," *AIDS*, 10(10):1085-1090 (1996).
Schuster et al., "Serine-202 is the Putative Precursor of the Active Site Dehydroalanine of Phenylalanine Ammonia Lyase. Site-directed Mutagenesis Studies on the Enzyme from Parsley (*Petroselinum crispum* L.)," *Federation of European Biochemical Societies Letters*, 349:252-254 (1994).

(56) References Cited

OTHER PUBLICATIONS

Schuster et al., "The Mechanism of Action of Phenylalanine Ammonia-Lyase: The Role of Prosthetic Dehydroalanine," *Proceedings of the National Academy of Sciences USA*, 92:8433-8437 (1995).
Schwede et al., "Crystal Structure of Histidine Ammonia-Lyase Revealing a Novel Polypeptide Modification as the Catalytic Electrophile," *Biochemistry*, 38:5355-5361 (1999).
Shen et al., "Biochemical Properties and Immunogenicity of L-Phenylalanine Ammonia-Lyase: Effects on Tumor-Bearing Mice," *Cancer Treatment Reports*, 63(6):1063-1068 (1979).
Shen et al., "Clearance of Phenylalanine Ammonia-Lyase from Normal and Tumor-Bearing Mice," *Cancer Research*, 37:1051-1056 (1977).
Shen et al., "Total-Body Radiation Suppression of the Clearance of Phenylalanine Ammonia-Lyase from Mouse Plasma," *Journal of the Reticuloendothelial Society*, 23(3):167-175 (1978).
Sorlie et al. "Mechanistic Features and Structure of the Nitrogenase alpha-Gin-195 MoFe Protein," *Biochemistry*, 40:1540-1549 (2001).
Spaapen et al., Tetrahydrobiopterin-Responsive Phenylalanine Hydroxylase Deficiency, State of the Art, *Molecular Genetics and Metabolism*, 78:93-99 (2003).
Spencer et al., "A Strategy for Mapping and Neutralizing Conformational Immunogenic Sites on Protein Therapeutics," *Proteomics*, 2(3):271-279 (2002).
Stith et al., "Effects of Phenylalanine Ammonia-Lyase and Phenylalanine Deprivation on Murine Leukemic Lymphoblasts in Vitro," *Cancer Research*, 33:966-971 (1973).
Suchi et al., "Molecular Cloning of a cDNA Encoding Human Histidase," *Biochimica et Biophysica Acta*, 1216:293-295 (1993).
Sun et al., "Solid Substrate Phosphorescent Immunoassay Based on Bioconjugated Nanoparticles," *Analytical Letters*, 34(10):1627-1637 (2001).
Tang et al., "New Amperometric and Potentiometric Immunosensors Based on Gold Nanoparticles/Tris (2,2'-Bipyridyl)Cobalt(III) Multilayer Films for Hepatitis B Surface Antigen Determinations," *Biosensors and Bioelectronics*, 21:539-548 (2005).
Tangri et al., "Rationally Engineered Proteins or Antibodies with Absent or Reduced Immunogenicity," *Current Medical Chemistry*, 9:2191-2199 (2002).
Taylor et al., "Cloning and Expression of Rat Histidase," *The Journal of Biological Chemistry*, 265(30):18192-18199 (1990).
Taylor et al., "Site-Directed Mutagenesis of Conserved Serines in Rat Histidase," *Journal of Biological Chemistry*, 269(44):27473-27477 (1994).
Tosoh Bioscience LLC. Process Media Products Toyopearl GigaCap Q-650. Nov. 20, 2008 [Retrieved from the Internet on Aug. 2, 2011:<URL: http://web.archive.org/web/20081120025210/http://www.separations.us.tosohbioscience.com/Products/ProcessMedia/ByMode/IEC/ToyopearlGigaCapQ-650.htm>].
Tsai et al., "Sensitive measurement of polyethylene glycol-modified proteins," *Biotechniques*, 30(2):396-402 (2001).
Vellard, "The Enzyme as Drug: Application of Enzymes as Pharmaceuticals," *Current Opinion in Biotechnology*, 14:1-7 (2003).
Veronese et al., "Branched and Linear Poly(Ethylene Glycol): Influence of the Polymer Structure on Enzymological, Pharmacokinetic, and Immunological Properties of Protein Conjugates," *Journal of Bioactive and Compatible Polymers*, 12:196-207 (1997).
Veronese et al., "Introduction and Overview of Peptide and Protein Pegylation," *Advanced Drug Delivery Reviews*, 54(4):453-456 (2002).

Wang et al. Structural and biochemical characterization of the therapeutic *Anabaena variabilis* phenylalanine ammonia lyase,: *J. Mol. Biol.* 380:623-635 (2008).
Wang et al., "New Carbohydrate-Based Materials for the Stabilization of Proteins," *Journal of the American Chemical Society*, 1992, 114:378-380 (1992).
Wang et al., "New Preparation for Oral Administration of Digestive Enzyme. Lactase Complex Microcapsules," *Biomat. Art. Cells Immob. Biotech.*, 21(5):637-646 (1993).
Wang et al., "Structural and Biological Characterization of Pegylated Recombinant Interferon alpha-2b and its Therapeutic Implications," *Advanced Drug Delivery Reviews*, 54:547-570 (2002).
Wang et al., "Structure-Based Chemical Modification Strategy for Enzyme Replacement Treatment of Phenylketonuria," *Molecular Genetics and Metabolism*, 86(1-2):134-140 (2005) Academic Press, San Diego, CA.
Watts et al. "Discovery of Substrate Selectivity Switch in Tyrosine Ammonia-Lyase, a Member of the Aromatic Amino Acid Lyase Family," *Chemistry and Biology, Current Biology* (London, GB) vol. 13, No. 12, pp. 1317-1326 (Dec. 26, 2006).
Whittle et al., "Protein Structure-Based Drug Design," *Annual review of Biophysics and Biomolecular Structure*, 23:349-375 (1994).
Wieder et al., "Some Properties of Polyethylene Glycol: Phenylalanine Ammonia-Lyase Adducts," *The Journal of Biological Chemistry*, 254(24):12579-12587 (1979).
Wilks et al., "Design of a Specific Phenyllactate Dehydrogenase by Peptide Loop Exchange on the Bacillus *Stearothermophilus* Lactate Dehydrogenase Framework," *Biochemistry*, 31:7802-7806 (1992).
Williams et al., "The Gene sltA Encodes a Phenylalanine Ammonia-Lyase that is Involved in the Production of a Stilbene Antibiotic in *Photorhabdus Luminescens* TT01," *Microbiology*, 151:2543-2550 (2005).
Woolf et al., "The Dietary Treatment of Phenylketonuria," *Archives of Disease in Childhood*, 33:31-45, vol. 33 (1958).
Xiang et al., "Biochemical Characterization of a Prokaryotic Phenylalanine Ammonia Lyase," *Journal of Bacteriology*, 187(12):4286-4289 (2005) [also includes Author's correction 188(14):5331 2006].
Xiang et al., "Inactivation, Complementation, and Heterologous Expression of encP, a Novel Bacterial Phenylalanine Ammonia-Lyase Gene," *Journal of Biological Chemistry*, 277(36):32505-32509 (2002).
Yeung et al., "Elimination of an Immunodominant CD4+ T Cell Epitope in Human IFN-β Does Not Result in an In Vivo Response Directed at the Subdominant Epitope," *Journal of Immunology*, 172:6658-6665 (2004).
Yoshioka et al., "Optimal Site-Specific PEGylation of Mutant TNF-α Improves Its Antitumor Potency," *Biochemical and Biophysical Research Communications*, 315:808-814 (2004).
Zhao et al., "Development of an Assay to Determine the Plasma Concentration of a PEGylated Phenylalanine Ammonia Lyase (rAvPAL-PEG), an Enzyme Substitution Therapy for the Treatment of Phenylketonuria (PKU)," *2009 AAPS National Biotechnology Conference*. Available at http://abstracts.aapspharmaceutica.com/ExpoNBC09/CC/forms/attendee/index.aspx?content=sessionInfo&sessionId=289 (last visited Jun. 27, 2011).
Zon et al., "Inhibitors of Phenylalanine Ammonia-Lyase: 1-Aminobenzylphosphonic Acids Substituted in the Benzene Ring," *Phytochemistry*, 59:9-21 (2002).

* cited by examiner

Gene Sequence of Nostoc punctiforme PAL

```
  1  atgaatataa catctctaca acagaacata acgcgttctt ggcaaatacc tttcactaat
 61  agttcagatt caatcgtaac tgtaggcgat cgcaatctga caatcgacga ggttgtaaat
121  gttgctcgtc atggaacaca ggtgcgctta actgataatg cagatgtcat tcggggtgtt
181  caagcatctt gtgattacat taacaatgca gtcgaaacag cacagccaat ttacggggtg
241  acatctggct ttgcggtat ggcagatgtt gtcatctctc gcgaacaagc agcggaactt
301  cagactaatt taatttggtt tctgaaatcc ggcgcaggaa acaaattatc gttagcagac
361  gtgcgtgcag ctatgctctt acgtgcaaat tcacatttgt atggtgcgtc tggtatacga
421  ctcgaactta ttcagcggat tgaaactttc ctcaacgctg gcgtgacacc ccatgtctat
481  gagtttggct ctatcggtgc tagcggcgat ttggtgccat tatcctacat tactgggca
541  ctaatcggtc tagatcctag ctttacagtt gacttcgacg gtaaagaaat ggatgccgtt
601  acagccttgt ctcgtttggg tttgccaaag ttgcaattgc aaccgaaaga aggtttagca
661  atgatgaatg gcacctcagt catgacaggt attgcagcta actgtgtgta cgatgcgaaa
721  gtttgctcg ctctgacaat gggtgtacac gccttagcca tccaaggttt atacgaaacg
781  aatcaatctt tccaccgtt tattcatcag tgcaagccac atccggtca actatggaca
841  gcagatcaaa tgttttctct gctgaaagat tcatctttag ttcgtgaaga gttggatggt
901  aaacacgaat accgtggtaa agatctgata caggatcgtt attctctccg ctgtctgca
961  cagttcatag ggccaatcgt tgatggggta tcagagatta ccaagcaaat cgaggtagaa
```

FIG. 1A

Gene Sequence of Nostoc punctiforme PAL

```
1021 atgaactcag tcaccgataa cccattgatt gatgtcgaga accaagttag ttatcacggc
1081 ggcaattttc tcggacagta tgtgggtgtg acaatggatc gcctacgtta ttacataggg
1141 ctattggcca aacacatcga tgtgcagatt gcacttcttg tctcgccaga gtttagcaac
1201 ggcttaccac cctctttagt tggtaatagc gatcgcaaag ttaatatggg actcaaaggt
1261 ttgcaaatca gtggaaactc gattatgcca ctgttgagct tctatggaaa ttccctagcc
1321 gatcgctttc ctacccacgc cgagcaattt aatcaaaata ttaacagcca aggctatatt
1381 tccgcaaatt tgacacgtcg ttccgtagac atatttcaga attatatggc gatcgcgttg
1441 atgtttggag ttcaagctgt tgacctccgc acatataaga tgaaaggtca ttatgatgca
1501 cgtacatgcc tctcacccaa tactgtgcag ttatacacag cagtctgcga ggtagttgga
1561 aagccactaa cgtctgtgcg tccatacatt tggaacgaca acgagcaatg tttagatgag
1621 catattgccc ggatttcagc tgatatcgct ggtggtggtt taattgtgca agcagttgag
1681 catattttt cgagcttaaa gtcaacgtaa
```

FIG. 1A
*(Continued)*

Protein Sequence of Nostoc punctiforme PAL

MNITSLQQNITRSWQIPFTNSSDSIVTVGDRNLTIDEVVNVARH

GTQVRLTDNADVIRGVQASCDYINNAVETAQPIYGVTSGFGGMADVVISREQAAELQT

NLIWFLKSGAGNKLSLADVRAAMLLRANSHLYGASGIRLELIQRIETFLNAGVTPHVY

EFGSIGASGDLVPLSYITGALIGLDPSFTVDFDGKEMDAVTALSRLGLPKLQLQPKEG

LAMMNGTSVMTGIAANCVYDAKVLLALTMGVHALAIQGLYGTNQSFHPFIHQCKPHPG

QLWTADQMFSLLKDSSLVREELDGKHEYRGKDLIQDRYSLRCLAQFIGPIVDGVSEIT

KQIEVEMNSVTDNPLIDVENQVSYHGGNFLGQYVGVTMDRLRYYIGLLAKHIDVQIAL

LVSPEFSNGLPPSLVGNSDRKVNMGLKGLQISGNSIMPLLSFYGNSLADRFPTHAEQF

NQNINSQGYISANLTRRSVDIFQNYMAIALMFGVQAVDLRTYKMKGHYDARTCLSPNT

VQLYTAVCEVVGKPLTSVRPYIWNDNEQCLDEHIARISADIAGGGLIVQAVEHIFSSL

KST

*FIG. 1B*

Gene Sequence of Anabaena variabilis PAL

```
  1  atgaagacac tatctcaagc acaaagcaaa acctcatctc aacaattttc ttttactgga
 61  aattcttctg ccaatgtaat tattggtaat cagaaactca caatcaatga tgttgcaagg
121  gtagcgcgta atggcacctt agtgtcttta accaataaca ctgatatttt gcagggtatt
181  caggcatctt gtgattacat taataatgct gttgaatctg gggaaccaat ttatggagtg
241  acatctggtt ttggcggtat ggccaatgtt gccatatccc gtgaacaagc atctgaactc
301  caaaccaact tagtttggtt cctgaaaaca ggtgcaggga acaaattacc cttggcggat
361  gtgcgcgcag ctatgctctt gcgtgcaaac tctcatatgc gcggtgcatc tggcatcaga
421  ttagaactta tcaagcgtat ggagattttc cttaacgctg tgtcacacc atatgtgtat
481  gagtttggtt caattggtgc aagtggtgat ttagtgccac tatcctacat tactggttca
541  ctgataggct tagatccag ttttaaggtt gacttcaccg gacttgacattgt ggatgcgcca
601  acagctctac gtcaactgaa tttgtcaccc ttgacattgt gccgaagga aggcttggcg
661  atgatgaacg gcacttcagt catgacaggt attgcagcaa actgcgtcta cgatactcaa
721  attttaactg cgatcgctat gggcgttcac gctctagata tccaagcttt aaacggaacc
781  aatcaatcat tccatccatt tatccataat tccaaaccac atcctggtca attatgggca
841  gcagatcaga tgatttcttt gttagccaat cgagttgatt tccagtaag ttcgtgatga gttagatggt
901  aaacacgatt atcgtgatca cgagttgatc caagatcgtt actcactccg atgccttccc
961  cagtatttgg ggccaatcgt tgatggaatt tcccagattg ccaaacaaat tgaaatcgaa
```

FIG. 2A

Gene Sequence of Anabaena variabilis PAL

```
1021 atcaactcag tcaccgataa cccactaatt gatgttgata accaagctag ctatcatgga
1081 ggaaatttcc tcggacagta cgtgggtatg ggaatggatc acctgcgtta ctatattggg
1141 ttattggcta aacacctaga tgtgcagatt gccctcctcg cctcaccaga gtttagcaat
1201 ggactaccac catctttatt aggcaaccga gaacgtaaag tcaatatggg actcaaaggt
1261 ctgcaaatat gcggtaactc aattatgcca ctgttgacct tctatggaaa ttccatcgcc
1321 gatcgctttc ctacccatgc agaacaattt aatcagaaca tcaacagtca aggatacact
1381 tcagcgactc tagcccgccg ttctgtggat atcttccaga attatgtggc gatcgctctg
1441 atgtttggag tccaagctgt tgacctcccgc acatataaaa agactggtca ttacgatgca
1501 cgcgcctgtc tatcacctgc aactgagcgc ttatattcag cagtccgcca cgtagttgga
1561 caaaaccaa cttcagatcg cccatatatt tggaatgata cagtccgcca atgagcaagg actgatgag
1621 catattgccc ggatttctgc tgatatcgct gctggtggtg tgattgtgca agcagttcaa
1681 gatatcttac cctgcttgca ttaa
```

FIG. 2A
*(Continued)*

Protein Sequence of Anabaena variabilis PAL

```
  1  mktlsqaqsk tssqqfsftg nssanviign qkltindvar varngtlvsl tnntdilqgi
 61  qascdyinna vesgepiygv tsgfggmanv aisregasel lnagvtpyvy efgsigasgd
121  vraamllran shmrgasgir lelikrmeif lnagvtpyvy efgsigasgd lvplsyitgs
181  ligldpsfkv dfngkemdap talrqlnlsp ltllpkegla mmngtsvmtg iaancvydtq
241  iltaiamgvh aldiqalngt nqsfhpfihn skphpgqlwa adqmisllan sqlvrdeldg
301  khdyrdheli qdryslrclp qylgpivdgi sqiakqieie insvtdnpli dvdnqasyhg
361  gnflgqyvgm gmdhlryyig llakhldvqi allaspefsn glppslignr erkvnmglkg
421  lqicgnsimp lltfygnsia drfpthaegf ngninsggyt satlarrsvd ifqnyvaial
481  mfgvqavdlr tykktghyda raclspater lysavrhvvg qkptsdrpyi wndneqglde
541  hiarisadia aggvivqavq dilpclh
```

*FIG. 2B*

Protein Sequence of AvPAL Variants (Cysteine Mutants)

A. AvPAL_C64S (SEQ ID NO:7)

MKTLSQAQSKTSSQQFSFTGNSSANVIIGNQKLTINDVARVARNGTLVSLTNNTDILQGIQASSDYINNA
VESGEPIYGVTSGFGGMANVAISREQASELQTNLVWFLKTGAGNKLPLADVRAAMLLRANSHMRGASGIR
LELIKRMEIFLNAGVTPYVYEFGSIGASGDLVPLSYITGSLIGLDPSFKVDFNGKEMDAPTALRQLNLSP
LTLLPKEGLAMMNGTSVMTGIAANCVDTQILTAIAMGVHALDIQALNGTNQSFHPFIHNSKPHPGQLWA
ADQMISLLANSQLVRDELDGKHDYRDHELIQDRYSLRCLPQYLGPIVDGISQIAKQIEIEINSVTDNPLI
DVDNQASYHGGNFLGQYVGMGMDHLRYYIGLLAKHLDVQIALLASPEFSNGLPPSLLGNRERKVNMGLKG
LQICGNSIMPLLTFYGNSIADREPTHAEQFNQNINSQGYTSATLARRSVDIFQNYVAIALMFGVQAVDLR
TYKKTGHYDARACLSPATERLYSAVRHVVGQKPTSDRPYIWNDNEQGLDEHIARISADIAAGGVIVQAVQ
DILPCLH

*FIG. 3A*

Protein Sequence of AvPAL Variants (Cysteine Mutants)

B. AvPAL_C318S (SEQ ID NO:8)

MKTLSQAQSKTSSQQFSFTGNSSANVIIGNQKLTINDVARVARNGTLVSLTNNTDILQGIQASCDYINNA
VESGEPIYGVTSGFGGMANVAISREQASELQTNLVWFLKTGAGNKLPLADVRAAMLLRANSHMRGASGIR
LELIKRMEIFLNAGVTPYVYEFGSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLWA
ADQMISLLANSQLVRDELDGKHDYRDHELIQDRYSLRSLPQYLGPIVDGISQIAKQIEIEINSVTDNPLI
DVDNQASYHGGNFLGQYVGMGMDHLRYYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARACLSPATERLYSAVRHVVGQKPTSDRPYIWNDNEQLDEHIARISADIAAGGVIVQAVQ
DILPCLH

FIG. 3B

Protein Sequence of AvPAL Variants (Cysteine Mutants)

C. AvPAL_C503S (SEQ ID NO:9)

MKTLSQAQSKTSSQQFSFTGNSSANVIIGNQKLTINDVARVARNGTLVSLTNNTDILQGIQASCDYINNA
VESGEPIYGVTSGFGGMANVAISREQASELQTNLVWFLKTGAGNKLPLADVRAAMLLRANSHMRGASGIR
LELIKRMEIFLNAGVTPYVYEFGSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLWA
ADQMISLLANSQLVRDELDGKHDYRDHELIQDRYSLRCLPQYLGPIVDGISQIAKQIEIEINSVTDNPLI
DVDNQASYHGGNFLGQYVGMGMDHLRYYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARASLSPATERLYSAVRHVVGQKPTSDRPYIWNDNEQGLDEHIARISADIAAGGVIVQAVQ
DILPCLH

*FIG. 3C*

Protein Sequence of AvPAL Variants (Cysteine Mutants)

D. AvPAL_C565S (SEQ ID NO:10)

MKTLSQAQSKTSSQQFSFTGNSSANVIIGNQKLTINDVARVARNGTLVSLTNNTDILQGIQASCDYINNA
VESGEPIYGVTSGFGGMANVAISREQASELQTNLVWFLKTGAGNKLPLADVRAAMLLRANSHMRGASGIR
LELIKRMEIFLNAGVTPYVYEFGSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLWA
ADQMISLLANSQLVRDELDGKHDYRDHELIQDRYSLRCLPQYLGPIVDGISQIAKQIEIEINSVTDNPLI
DVDNQASYHGGNFLGQYVGMGMDHLRYYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARACLSPATERLYSAVRHVVGQKPTSDRPYIWNDNEQGLDEHIARISADIAAGGVIVQAVQ
DILP<u>S</u>LH

FIG. 3D

Protein Sequence of AvPAL Variants (Cysteine Mutants)

E. AvPAL_C565SC503S (SEQ ID NO:11)

MKTLSQAQSKTSSQQFSFTGNSSANVIIGNQKLTINDVARVARNGTLVSLTNNTDILQGIQASCDYINNA
VESGEPIYGVTSGFGGMANVAISREQASELQTNLVWFLKTGAGNKLPLADVRAAMLLRANSHMRGASGIR
LELIKRMEIFLNAGVTPYVYEFGSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLWA
ADQMISLLANSQLVRDELDGKHDYRDHELIQDRYSLRCLPQYLGPIVDGISQIAKQIEIEINSVTDNPLI
DVDNQASYHGGNFLGQYVGMGMDHLRYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARASLSPATERLYSAVRHVVGQKPTSDRPYIWNDNEQGLDEHIARISADIAAGGVIVQAVQ
DILPSLH

ASSAYS FOR DETECTION OF PHENYLALANINE AMMONIA-LYASE AND ANTIBODIES TO PHENYLALANINE AMMONIA-LYASE

CROSS-REFERENCE TO RELATED APPLICATIONS

This application is a continuation application of U.S. application Ser. No. 13/056,606 filed Apr. 21, 2011, which is a U.S. national phase application of the international application No. PCT/US2009/004386 filed Jul. 30, 2009, which claims priority to U.S. provisional application No. 61/084,961 filed Jan. 30, 2008, each of which is incorporated herein by reference in its entirety.

FIELD

Provided herein are methods of detecting the presence of a pegylated enzyme, an enzyme-specific antibody (e.g., a neutralizing antibody or of a particular isotype), or a polyethylene glycol (PEG)-specific antibody in a sample, such as a bodily fluid or tissue of a patient.

BACKGROUND

Phenylalanine ammonia-lyase (PAL) is a non-mammalian enzyme widely distributed in plants (Koukol et al., *J Biol Chem* 236:2692-2698, 1961; Hanson et al., *The Enzymes* 7:75-166, 1972; Poppe et al., *Curr Org Chem* 7:1297-1315, 2003), some fungi (Rao et al., *Can J Biochem* 45(12):1863-1872, 1967; Abell et al., *Methods Enzymol* 142:242-253, 1987), and bacteria (Bezanson et al., *Can J Microbiol* 16:147-151, 1970; Xiang et al., *J Biol Chem* 277:32505-32509, 2002; Hill et al., *Chem Commun* 1358-1359, 2003) and can be recombinantly produced in *Escherichia coli*.

PAL from two cyanobacteria strains, *Anabaena variabilis* (Av) and *Nostoc punctiforme* (Np), has been cloned and expressed in bacteria (e.g., *Escherichia coli* (*E. coli*), and was shown to display PAL enzyme activity in vitro and in vivo (see, e.g., U.S. Pat. Nos. 7,531,341; 7,534,595; 7,537,923 and 7,560,263). A pegylated recombinant *Anabaena variabilis* PAL (rAvPAL-PEG) has also been produced, wherein the rAvPAL protein was derivatized by covalent attachment of polyethylene glycol (PEG) to increase its half-life and optimize its pharmacokinetic profile and/or reduce its immunogenicity (Id.). rAvPAL-PEG has been shown to metabolize phenylalanine and is being developed as an enzyme substitution therapy (EST) for patients disorders or diseases associated with elevated levels of phenylalanine, such as PKU, as well as in cancer therapy (Id.).

A concern of administration of enzymes to patients, for example, for PKU EST or cancer therapy, is whether sufficient amounts of the enzyme are available in the body to exert a therapeutic effect in the patient. Moreover, in the case of pegylated enzymes, current methods used to determine the concentration of PEG are relatively insensitive (see, e.g., U.S. Pat. No. 6,596,849), and methods to detect the enzyme itself are complicated by the presence of the PEG. To date, such methods have not determined an effective way to expose the immunogenic epitopes of the therapeutic enzyme (e.g., rAvPAL-PEG) for capture by an immobilized antibody specific for the target therapeutic enzyme, and maximize the number of epitopes recognized by the antibodies, while at the same time minimizing the number of epitopes masked by the PEG molecules.

A further concern of administration of enzymes to a patient, e.g., for PKU EST or cancer therapy, is the possible development of enzyme-specific antibodies in patients, for example, those receiving multiple rounds of therapy. These enzyme-specific antibodies may precipitate potential adverse events and lead to changes in clinical efficacy, including, for example, anaphylactoid-type reactions associated with antibodies of the IgE isotype, changes in pharmacokinetic profile, neutralization of the enzymatic activity, interference with receptor-mediated enzyme uptake, and breaking of tolerance toward self proteins. Current assays to measure the amount of anti-enzyme antibodies in body fluids also suffer from a variety of technical issues, thereby making their interpretation difficult (see Mire-Sluis et al., *J. Immunological Methods* 289:1-16, 2004).

Given these concerns, as well as the shortcomings of currently available assays, there remains a need for a reliable, sensitive and specific assays to accurately detect or otherwise measure (i) an enzyme (e.g., a rAvPAL) in body fluids, tissues or other samples of a patient receiving the enzyme, e.g., for EST or cancer therapy; (ii) a pegylated enzyme, such as extensively pegylated enzyme (i.e., an enzyme having a sufficient number of PEG molecules attached such that at least some of the immunogenic epitopes of the enzyme are masked by the PEG molecules), (e.g., a rAvPAL-PEG) in bodily fluids, tissues or other samples of patient receiving the enzyme, e.g., for EST or cancer therapy; and/or (iii) enzyme- or PEG-specific antibodies (e.g., anti-rAvPAL, anti-rAvPAL-PEG antibodies, or anti-PEG antibodies) in body fluids, tissues or other samples of patient receiving the enzyme, e.g., for EST or cancer therapy. Such assays could enable assessment of the treatment regimen in a patient receiving the enzyme, e.g., for EST or cancer therapy and facilitate more efficient design of patient therapy.

SUMMARY

Provided herein are methods of detecting the presence of a pegylated enzyme, an enzyme-specific antibody (e.g., a neutralizing antibody or of a particular isotype), or a PEG-specific antibody in a sample, such as a bodily fluid or tissue of a patient. In certain embodiments, the methods are for the detection and/or measurement of therapeutic enzymes and antibodies associated with administration of such therapeutic enzymes, including the use of a PAL or a variant thereof, for example, in a patient receiving PAL or a variant thereof (e.g., an AvPAL or rAvPAL-PEG) during the course of EST for elevated phenylalanine levels (e.g., phenylketonuria) or cancer therapy. Also provided are kits for carrying out said methods.

In a first aspect, provided herein is a method of detecting the presence of a pegylated enzyme, e.g., rAvPAL-PEG or variant thereof, in a sample (e.g., a body fluid, such as plasma, or a tissue sample), said method comprising: (a) acidifying the pegylated enzyme in the sample by adding an acidification reagent; (b) neutralizing the acidified pegylated enzyme in the sample by adding a neutralization buffer; (c) contacting the sample with an immobilized first antibody that immunospecifically binds with the pegylated enzyme; (d) optionally removing unbound sample; (e) contacting the sample bound to the immobilized first antibody with a detectable second antibody, wherein the second antibody immunospecifically binds to PEG; (f) optionally removing unbound second antibody; and (g) detecting the presence of the second antibody bound to the sample; wherein detection above background of an amount of the second antibody bound to the sample, e.g., an increase in the amount of second antibody bound to the sample as compared to a control sample having no pegylated enzyme, indicates the presence of pegylated enzyme in the sample. In some embodiments, the neutralized pegylated enzyme described in (b) is introduced into a different assay buffer before contacting the immobilized first antibody described in (c). In some embodiments, the acidification reagent is 0.1 M glycine, pH 2.7 and/or the neutralization buffer is 0.5 M Tris-HCl, pH 8.5.

In certain embodiments, the sample is a body fluid, such as blood or plasma, or a tissue sample from a patient (e.g., a mammal, such as a human). In an embodiment, the concentration of pegylated enzyme in the sample is determined. In one embodiment, the limit of detection is less than 5 ng/mL, or less than 3 ng/mL. In another embodiment, the limit of detection is between 5 ng/mL and 2 ng/mL, such as between 3 ng/mL and 2 ng/mL. In an embodiment, the sample is plasma, which is equal to or less than 5% or equal to or less than 2% of the volume as described in (a). In some embodiments, the patient has elevated phenylalanine levels. In specific embodiments, the patient has been (or will be) administered the pegylated enzyme, for example, for EST (e.g., for PKU) or cancer therapy. In an embodiment, the pegylated enzyme is rAvPAL-PEG or a variant thereof. In one embodiment, the pegylated enzyme is rAvPAL-PEG having its cysteine residue at position 503 substituted with serine residues (rAvPAL-PEG_C503S). In another embodiment, the pegylated enzyme is rAvPAL-PEG having its cysteine residues at position 565 substituted with serine residues (rAvPAL-PEG_C565S). In yet another embodiment, the pegylated enzyme is rAvPAL-PEG having its cysteine residues at positions 503 and 565 substituted with serine residues (rAvPAL-PEG_C565SC503S). In other embodiments, the pegylated enzyme is rAvPAL-PEG_C503S, rAvPAL-PEG_C565S, rAvPAL-PEG_C565SC503S, or any combination thereof.

In a second aspect, provided herein is a method of detecting the presence of an enzyme-specific antibody (e.g., an anti-AvPAL-specific antibody) in a sample (e.g., a body fluid, such as plasma, or a tissue sample), said method comprising: (a) contacting the sample with an immobilized enzyme (e.g., AvPAL); (b) optionally removing unbound sample; (c) contacting the sample bound to the immobilized enzyme with a detectable antibody, wherein the detectable antibody immunospecifically binds to Ig; (d) optionally removing unbound detectable antibody; and (e) detecting the presence of the detectable antibody bound to the sample; wherein detection above background of an amount of the detectable antibody bound to the sample, e.g., an increase in the amount of detectable antibody bound to the sample as compared to a control sample having no enzyme-specific antibody, indicates the presence of enzyme specific antibody in the sample.

In certain embodiments, the sample is a body fluid, such as blood or plasma, or a tissue sample from a patient (e.g., a mammal, such as a human). In an embodiment, the concentration of enzyme-specific antibody in the sample is determined. In the methods provided herein, any isotype of enzyme-specific antibody can be detected. In an embodiment, an enzyme-specific antibody of IgG isotype can be detected, and, in certain embodiments, the limit of detection is between 1.6 ng/mL and 8.6 ng/mL. In some embodiments, the limit of detection is less than 8.6 ng/mL or less than 4.2 ng/mL, such as between 2.1 ng/mL and 1.6 ng/mL. In other embodiments, an enzyme-specific antibody of IgM isotype can be detected, and, in certain embodiments, the limit of detection is less than 5.9 ng/mL, such as between 5.9 ng/ml and 2.8 n/ml. In an embodiment, an enzyme-specific antibody of IgE isotype can be detected. In other embodiments, an enzyme-specific antibody of IgA can be detected. In an embodiment, the sample is serum or plasma, which is equal to or less than 5% or equal to or less than 2% of the volume as described in (a).

In some embodiments, the patient has elevated phenylalanine levels. In specific embodiments, the patient has been or will be administered the enzyme or pegylated enzyme, for example, for EST (e.g., for PKU) or cancer therapy.

In an embodiment, the enzyme is rAvPAL or a variant thereof. In one embodiment, the enzyme is rAvPAL_C503S, rAvPAL_C565S, rAvPAL_C565SC503S, or any combination thereof. In some embodiments, the enzyme is a pegylated enzyme. In an embodiment, the pegylated enzyme is rAvPAL-PEG. In other embodiments, the pegylated enzyme is rAvPAL-PEG_C503S, rAvPAL-PEG_C565S, rAvPAL-PEG_C565SC503S, or any combination thereof.

In a third aspect, provided herein is a method for detecting the presence of neutralizing enzyme-specific antibodies (e.g., a neutralizing anti-AvPAL-specific antibody) in a sample (e.g., a body fluid, such as plasma, or a tissue sample), said method comprising: (a) contacting the sample with the enzyme (e.g., AvPAL or variant thereof) that is optionally immobilized on a solid support; (b) optionally removing unbound sample; (c) adding a substrate for the enzyme; (d) optionally removing unbound substrate; and (e) detecting the presence of enzymatic reactivity between the enzyme and substrate; wherein a reduction of enzymatic activity, e.g., as compared to a sample having no neutralizing anti-enzyme antibodies, indicates the presence of neutralizing anti-enzyme antibodies in the sample. In certain embodiments, the sample is a body fluid, such as blood or plasma, or a tissue sample from a patient (e.g., a mammal, such as a human). In an embodiment, the concentration of neutralizing enzyme-specific antibody in the sample is determined. In certain embodiments, the limit of detection is less than or equal to 10 μg/mL. In an embodiment, the sample is serum or plasma, which is equal to or less than 5% or equal to or less than 2% of the volume as described in (a).

In some embodiments, the patient has elevated phenylalanine levels. In specific embodiments, the patient has been (or will be) administered the pegylated enzyme, for example, for EST (e.g., for PKU) or cancer therapy.

In an embodiment, the enzyme is rAvPAL or a variant thereof. In one embodiment, the enzyme is rAvPAL_C503S, rAvPAL_C565S, rAvPAL_C565SC503S or any combination thereof. In some embodiments, the enzyme is pegylated. In an embodiment, the pegylated enzyme is rAvPAL-PEG. In other embodiments, the pegylated enzyme is rAvPAL-PEG_C503S, rAvPAL-PEG_C565S, rAvPAL-PEG_C565SC503S, or any combination thereof.

In a fourth aspect, provided herein is a method for detecting or otherwise measuring the amount of polyethylene glycol (PEG)-specific antibodies (e.g., anti-PEG-specific antibodies) in a sample (e.g., a body fluid, such as plasma, or a tissue sample), said method comprising: (a) contacting the sample with an immobilized PEG; (b) optionally removing unbound sample; (c) contacting the sample bound to the immobilized PEG with a detectable antibody, wherein the detectable antibody immunospecifically binds to Ig; (d) optionally removing unbound detectable antibody; and (e) detecting the presence of the detectable antibody bound to the sample; wherein detection above background of an amount of the detectable antibody bound to the sample, e.g., an increase in the amount of detectable antibody bound to the sample as compared to a control sample having no enzyme-specific antibody, indicates the presence of PEG-specific antibody in the sample.

In certain embodiments, the sample is a body fluid, such as blood or plasma, or a tissue sample from a patient (e.g., a mammal, such as a human). In an embodiment, the concentration of PEG-specific antibody in the sample is determined. In the methods provided herein, any isotype of PEG-specific antibody can be detected (e.g., IgG, IgE, IgM or IgA). In an embodiment, the sample is serum or plasma, which is equal to or less than 5% or equal to or less than 2% of the volume as described in (a). In some embodiments, the patient has elevated phenylalanine levels. In specific embodiments, the patient has been (or will be) administered the pegylated enzyme, for example, for EST (e.g., for PKU) or cancer therapy.

In an embodiment, the PEG-specific antibodies are specific for a pegylated enzyme. In some embodiments, the pegylated enzyme is rAvPAL-PEG. In other embodiments, the pegylated enzyme is rAvPAL-PEG_C503S, rAvPAL-PEG_C565S, rAvPAL-PEG_C565SC503S, or any combination thereof.

DESCRIPTION OF THE FIGURES

FIGS. 1A-1B depict the (A) gene sequence (SEQ ID NO:1) and (B) protein sequence of NpPAL (SEQ ID NO:2) of *Nostoc punctiforme* PAL (NpPAL).

FIGS. 2A-2B depict the (A) gene sequence (SEQ ID NO:3) and (B) protein sequence of AvPAL (SEQ ID NO:4) of *Anabaena variabilis* PAL (AvPAL).

FIGS. 3A-3E depicts the protein sequences of AvPAL having a cysteine to serine substitution at (A) position 64 (AvPAL_C64S, SEQ ID NO:7); (B) position 318 (AvPAL_C318S, SEQ ID NO:8); (C) position 503 (AvPAL_C503S, SEQ ID NO:9); (D) position 565 (AvPAL_C565S, SEQ ID NO:10); or (E) at positions 503 and 565 (AvPAL_C565SC503S, SEQ ID NO:11). Cysteine to serine substitutions are underlined in bold.

FIG. 7A depicts the effect of a single subcutaneous injection of a pegylated AvPAL with cysteine to serine substitutions at positions 565 and 503 (AvPAL_C565SC503S) at 4 mg/kg (diamonds) and at 12 mg/kg (squares) into Cynomolgus monkeys on the plasma AvPAL_C565SC503S levels over time (hours). FIG. 7B depicts the effect of a single subcutaneous injection of AvPAL_C565SC503S at 4 mg/kg into Cynomolgus monkeys on the plasma AvPAL_C565SC503S (diamonds) and phenylalanine (squares) levels over time (hours).

FIG. 8A depicts the effect of a single intravenous injection of a pegylated AvPAL with cysteine to serine substitutions at positions 565 and 503 (AvPAL_C565SC503S) at 1 mg/kg (diamonds), at 5 mg/kg (squares) and at 25 mg/kg (triangles) into rats on the plasma AvPAL_C565SC503S levels over time (hours). FIG. 8B depicts the effect of a single subcutaneous injection of AvPAL_C565SC503S at 10 mg/kg (diamonds), at 25 mg/kg (squares) and at 250 mg/kg (triangles) into rats on the plasma AvPAL_C565SC503S levels over time (hours)

FIG. 9A depicts the effect of a pegylated AvPAL with cysteine to serine substitutions at positions 565 and 503 (AvPAL_C565SC503S) at 0.01, 0.1, 1, 10 and 100 μg/mL as indicated on proliferation (as measured by propidium iodide staining) of NOMO1 acute myeloid leukemia (AML) cells in vitro. FIG. 9B depicts the effect of AvPAL_C565SC503S at 0.1, 1, 10 and 100 μg/mL as indicated on proliferation of IM9 myeloma cells in vitro.

FIG. 10A depicts the effect of a pegylated AvPAL with cysteine to serine substitutions at positions 565 and 503 (AvPAL_C565SC503S) at 0.01, 0.1, 1, 10 and 100 μg/mL as indicated on proliferation (as measured by propidium iodide staining) of SF268 (top) and 498L (bottom) brain/CNS tumor cells in vitro. FIG. 10B depicts the effect of AvPAL_C565SC503S at 0.01, 0.1, 1, 10 and 100 μg/mL as indicated on proliferation of HT29 (top) and HCT116 (bottom) colon tumor cells in vitro. FIG. 10C depicts the effect of AvPAL_C565SC503S at 0.01, 0.1, 1, 10 and 100 μg/mL as indicated on proliferation of H460 (top), 529L (middle) and 629L (bottom) lung tumor cells in vitro. FIG. 10D depicts the effect of AvPAL_C565SC503S at 0.01, 0.1, 1, 10 and 100 μg/mL as indicated on proliferation of LNCAP (top), PC3M (middle) and DU145 (bottom) prostate tumor cells in vitro.

TERMINOLOGY

Figure 4A:
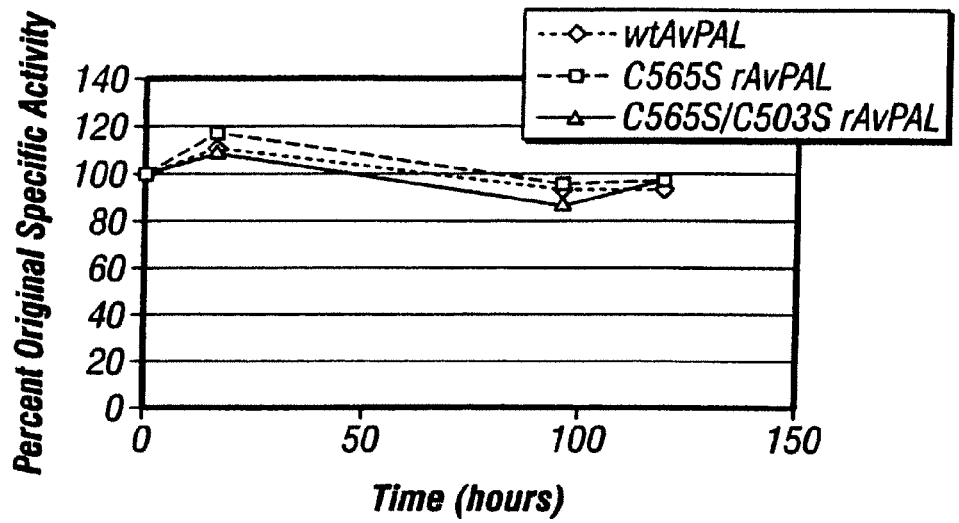
FIGS. 4A-4B depict the effect of cysteine to serine substitutions at position 565 or both positions 565 and 503 of (A) unpegylated AvPAL or (B) pegylated AvPAL on in vitro PAL specific enzyme activity after incubation for various lengths of time at 37° C.

Unless otherwise defined, all technical and scientific terms used herein have the same meaning as commonly understood by one of ordinary skill in the art. The following exemplary references can provide one of skill with a general definition of many of the terms provided herein: Singleton et al., *Dictionary of Microbiology and Molecular Biology* (2d ed. 1994); *The Cambridge Dictionary of Science and Technology* (Walker ed., 1988); *The Glossary of Genetics,* 5th Ed., Rieger et al. (eds.), Springer Verlag (1991); and Hale & Marham, *The Harper Collins Dictionary of Biology* (1991).

Each publication, patent application, patent, and other reference cited herein is incorporated by reference in its entirety to the extent that it is not inconsistent with the present disclosure and to the same extent as if each individual publication, patent application, patent, or other reference was specifically and individually indicated to be incorporated by reference.

It is noted here that as used in this specification and the appended claims, the singular forms "a," "an," and "the" include plural reference unless the context clearly dictates otherwise.

In the event there is a plurality of definitions for a term herein, those in this section prevail unless stated otherwise.

The term "about" or "approximately" means an acceptable error for a particular value as determined by one of ordinary skill in the art, which depends in part on how the value is measured or determined. In certain aspects, the term "about" or "approximately" means within 1, 2, 3, or 4 standard deviations. In certain aspects, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, "administer" or "administration" refers to the act of injecting or otherwise physically delivering a substance as it exists outside the body into a patient, such as by oral, mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or a symptom thereof, is being prevented, administration of the substance typically occurs before the onset of the disease or symptoms thereof.

The term "antibody" and "immunoglobulin" or "Ig" may be used interchangeably herein. The term "antibody" refers to all types of immunoglobulins and can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule, or any antigen-recognition (or antigen-binding) fragments thereof. The antibodies may be monoclonal or polyclonal and may be of any species of origin, including, but not limited to, mouse, rat, rabbit, horse, or human, or may be chimeric antibodies. See, e.g., Walker et al., Molec. Immunol. 1989; 26: 403-411; Morrision et al., Proc. Nat'l. Acad. Sci. 1984; 81: 6851; Neuberger et al., Nature 1984; 312: 604. The antibodies may be recombinant monoclonal antibodies produced according to the methods disclosed in U.S. Pat. No. 4,474,893 (Reading) or U.S. Pat. No. 4,816,567 (Cabilly et al.). The antibodies may also be chemically constructed by specific antibodies made according to the method disclosed in U.S. Pat. No. 4,676,980 (Segel et al.). Antibodies for use in the methods and kits provided herein can include, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab')$_2$ fragments, disulfide-linked Fvs (sdFv), anti-idiotypic (anti-Id) antibodies, and epitope-binding fragments of any of the above. In particular, for use in the methods and kits provided herein can include immunoglobulin molecules and immunologically active portions of immunoglobulin molecules, i.e., antigen binding domains or molecules that contain an antigen-binding site that immunospecifically binds to AvPAL or rAvPAL, or variants thereof (e.g., rAvPAL_C503S, rAvPAL_C565S, rAvPAL_C565SC503S) and/or derivatives thereof (e.g., rAvPAL-PEG, rAvPAL-PEG_C503S, rAvPAL-PEG_C565SC or rAvPAL-PEG_C565SC503S).

The term "body fluid" or "bodily fluid" as used herein refers to a fluid that is obtained from a patient, such as a mammal (e.g., human) patient. For example, a body fluid may be blood, cerebral spinal fluid (CSF), breast milk or urine. The body fluid can also be blood fractionated to remove cells (i.e., plasma) or cells and clotting factors (i.e., serum).

The term "capture moiety" or "first antibody" as used herein refers to a composition that is capable of being specifically bound by another composition that is immobilized, e.g., attached or otherwise linked, to a solid support. Many of the detection moieties provided herein can also be used as capture moieties so long as a binding event is involved. For example, useful capture moieties include affinity labels for which specific and selective ligands are available (e.g., biotin with avidin, glutathione with GST), haptens and proteins for which antisera or monoclonal antibodies are available (e.g., c-Myc), nucleic acid molecules with a sequence complementary to a target, and peptides for which specific and selective ligands are available (e.g., histidine tag with Ni). Molecules that affect the binding characteristics to a chromatographic resin are also envisioned. The solid support can be, for example, a filter, a plate, a membrane, a chromatographic resin, or a bead.

The term "cutpoint factor" or "threshold" as used herein generally refers to a value that is used to mathematically manipulate the signal from the naïve pooled matrix (e.g., serum or plasma) to set the minimum signal required from a sample to be considered positive. In some embodiments, the cutpoint factor is determined based on a confidence interval from a set of samples from individuals that have not been previously exposed to the therapeutic AvPAL enzyme. For example, the 95% confidence interval, calculated as 1.645 multiplied by the standard deviation across the individual samples, will lead to approximately a 5% false positive rate.

The term "derivative" when used in connection with antibody substances and polypeptides used in the methods provided herein refers to polypeptides chemically modified by techniques including, but not limited to, ubiquitination, conjugation to therapeutic or diagnostic agents, labeling (e.g., with radionuclides or various enzymes), covalent polymer attachment such as pegylation (i.e., derivatization with polyethylene glycol) and insertion or substitution by chemical synthesis of amino acids such as ornithine, which do not normally occur in human proteins. Derivatives can retain the binding properties of underivatized molecules. In certain embodiments, e.g., an AvPAL "derivative" refers to an rAvPAL-PEG. In other embodiments, e.g., an AvPAL variant "derivative" refers to an AvPAL-PEG_C503S, AvPAL-PEG_C565SC or rAvPAL-PEG_C565SC503S.

The terms "detectable moiety," "detection moiety" or a "label" as used herein refers to a composition (e.g., polypeptide or antibody) detectable by means including, but not limited to, spectroscopic, photochemical, biochemical, immunochemical, chemical, or other physical means. For example, useful detectable moieties or labels include Ruthenium (Ru)-based catalyst, Europium, $^{32}$P, $^{35}$S, fluorescent dyes, electron-dense reagents, enzymes (e.g., as commonly used in an ELISA), biotin-Streptavidin, digoxigenin, haptens and proteins for which antisera or monoclonal antibodies are available, and nucleic acid molecules with a sequence complementary to a target. The detectable moiety or label often generates a measurable signal, such as a radioactive, chromogenic, luminescent, or fluorescent signal, which can be used to quantitate the amount of bound detectable moiety or label in a sample.

The term "detectable antibody" as used herein refers to any antibody that can be detected. In some embodiments, the antibody is directly labeled with a detectable moiety. In certain embodiments, the antibody is a detectable anti-Ig antibody. The term "detectable anti-Ig antibody" as used herein refers to an anti-Ig antibody that can be detected. In some embodiments, the anti-Ig antibody is directly labeled with a detectable moiety in addition to its inherent binding to an Ig molecule. The Ig antibody can be of, for example, the IgG, IgE, IgM, IgD, IgA or IgY isotype. In other embodiments, the detectable antibody is a detectable anti-PEG antibody. The term "detectable anti-PEG antibody" as used herein refers to an anti-PEG antibody that can be detected. In certain embodiments, the anti-PEG antibody is directly labeled with a detectable moiety in addition to its inherent binding to a pegylated molecule.

The term "detectable PAL" and similar terms used herein refers to a PAL enzyme, e.g., AvPAL or a derivative or variant thereof, that can be detected. In certain embodiments, the PAL is directly labeled with a detectable moiety in addition to its inherent binding to a PAL-specific antibody.

The term "detectable PAL-PEG" as used herein refers to a pegylated (i.e., derivatized with polyethylene glycol) PAL enzyme (e.g., rAvPAL-PEG) or variant thereof that can be detected. In certain embodiments, the PAL-PEG reagent is directly labeled with a detectable moiety in addition to its inherent binding to a PAL-specific antibody or to a PEG-specific antibody.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of an antibody that immunospecifically binds to, e.g., an AvPAL or a variant or derivative thereof. In a specific embodiment, the antibody fragment that immunospecifically binds to, e.g., an AvPAL or a variant or derivative thereof, retains at least 1, at least 2, or at least 3 functions of the antibody.

The terms "identical" or percent "identity," in the context of two or more polynucleotide or polypeptide sequences, refer to two or more sequences or subsequences that are the same or have a specified percentage of nucleotides or amino acid residues that are the same, when compared and aligned for maximum correspondence, as measured using a sequence comparison algorithms or by visual inspection.

The term "antibody that immunospecifically binds" with a pegylated enzyme (e.g., rAvPAL-PEG) or "anti-pegylated enzyme antibodies" (e.g., anti-AvPAL-PEG antibodies) and analogous terms are used interchangeably herein and refer to antibodies and fragments thereof, that specifically bind to only, e.g., the pegylated enzyme, such as a rAvPAL-PEG antigen or epitope. For example, an antibody or a fragment thereof that "immunospecifically binds to" a rAvPAL-PEG antigen may be cross-reactive with related antigens. In one embodiment, an antibody or a fragment thereof that immunospecifically binds to a rAvPAL-PEG antigen does not cross-react with other antigens. An antibody or a fragment thereof that immunospecifically binds to a rAvPAL-PEG can be identified, for example, by immunoassays, BIAcore, or other techniques known to those of skill in the art. An antibody or a fragment thereof binds specifically to a rAvPAL-PEG when it binds to a rAvPAL-PEG antigen with higher affinity than to any cross-reactive antigen as determined using experimental techniques, such as RIAs and ELISAs. Typically, a specific or selective reaction will be at least twice background signal or noise and more typically more than 10 times background. Along the same lines, and in certain embodiments, antibodies provided herein immunospecifically bind to AvPAL, a variant thereof (e.g., rAvPAL_C503S, rAvPAL_C565S, rAvPAL_C565SC503S) and/or a derivative thereof (e.g., rAvPAL-PEG, rAvPAL-PEG_C503S, rAvPAL-PEG_C565SC or rAvPAL-PEG_C565SC503S). In other embodiments, antibodies provided herein immunospecifically bind to PEG. In yet other embodiments, antibodies provided herein immunospecifically bind to an Ig, such as an IgG, IgE, IgM, IgD, IgA isotype.

The term "interference" as used herein generally refers to the presence of substances in body fluid (e.g., serum or plasma) samples that prevent the target analyte from accurate detection and measurement. As used herein, interference generally refers to the effect of free drug or the effect of the matrix (e.g., serum or plasma) on the concentration-response relationship. For example, interference from matrix may be evaluated as the relative accuracy to samples without the potential interference to target a range of 75-125% relative accuracy.

The term "in vivo," in the context of samples, refers to samples obtained from a subject, e.g., a patient, such as a human patient, including biological samples such as biological or body fluids, e.g., blood, plasma, serum, bone marrow, spinal fluid, brain fluid, or tissues, such as lymph tissue, a thin layer cytological sample, a fresh frozen tissue sample or a tumor tissue. The term "in vivo" is to be distinguished from the term "in vitro," which encompasses cells or cell lines or biomolecular components of cells that have been cultured or propagated outside of a living organism.

The term "limit of detection," "LOD" or "sensitivity" as used herein generally refers to the lowest analyte concentration in a body fluid (e.g., serum or plasma) sample that can be detected but not necessarily quantitated as an exact value. For example, LOD may be defined as the analyte concentration that consistently generates a signal greater than the measured mean response of the pooled naïve matrix plus a cutpoint factor.

The term "matrix" or "matrices" as used herein generally refers to the biological background in which the antibodies are measured. Examples of matrices include, for example, body fluid and tissue.

The term "monoclonal antibody" refers to an antibody obtained from a population of homogenous or substantially homogeneous antibodies, and each monoclonal antibody will typically recognize a single epitope on the antigen. In certain embodiments, a "monoclonal antibody," as used herein, is an antibody produced by a single hybridoma or other cell, wherein the antibody immunospecifically binds to only a enzyme, e.g., AvPAL or rAvPAL-PEG as determined, e.g., by ELISA or other antigen-binding or competitive binding assay known in the art. The term "monoclonal" is not limited to any particular method for making the antibody. For example, monoclonal antibodies used in the methods provided herein may be made by the hybridoma method as described in Kohler et al.; Nature, 256:495 (1975) or may be isolated from phage libraries using the techniques known in the art. Other methods for the preparation of clonal cell lines and of monoclonal antibodies expressed thereby are well known in the art (see, for example, Chapter 11 in: *Short Protocols in Molecular Biology*, (2002) 5th Ed., Ausubel et al., eds., John Wiley and Sons, New York).

The term "naïve" as used herein refers to individuals, e.g., humans, which have not been previously exposed to a PAL, e.g., AvPAL, enzyme.

"Polyclonal antibodies" as used herein refers to an antibody population generated in an immunogenic response to a protein having many epitopes and thus includes a variety of different antibodies directed to the same and to different epitopes within the protein. Methods for producing polyclonal antibodies are known in the art (See, e.g., see, for example, Chapter 11 in: *Short Protocols in Molecular Biology*, (2002) 5th Ed., Ausubel et al., eds., John Wiley and Sons, New York).

The term "precision" as used herein generally refers to the variability in signal between the analysts and days. For example, precision may be evaluated as coefficient of variation, ranges of values, or using ANOVA statistics.

As used herein, the terms "prevent," "preventing," and "prevention" refer to the total or partial inhibition of the development, recurrence, onset or spread of a disease and/or symptom related thereto (e.g., a disease or symptom related thereto that is associated with elevated phenylalanine levels, such as PKU or cancer, in a patient), resulting from the administration of a therapy or combination of therapies provided herein, e.g., AvPAL, AvPAL variant, or any derivative thereof.

The term "reagent stability" as used herein generally refers to the robustness of preparation and storage stability of the reagents. For example, reagent stability may be established by the conditions that still permit values to be measured within 75-125% accuracy relative to freshly prepared reagents.

The term "robustness" as used herein generally refers to the capacity of the assay to remain unaffected by small variations in method parameters and indicates reliability of the assay during normal run conditions. For example, robustness can be evaluated as the percent change of reagent concentration, reagent volume, or incubation time that still generates signal within 75-125% accuracy relative to the nominal conditions.

The term "sample" as used herein generally refers to a test fluid or tissue, e.g., taken from a patient, that can be used in the methods provided herein. In some embodiments, the sample is an in vivo sample, for example, bodily (or biological) fluid from a subject, e.g., a patient, such as a human patient. Non-limiting examples of such bodily fluids include blood (e.g., human peripheral blood (HPB)), blood lysate, serum, blood plasma, fine needle aspirate, ductal lavage, spinal fluid, brain fluid, bone marrow, ascites fluid or any combination thereof. In other embodiments, the sample is taken from a biopsy tissue such as a tumor tissue from a subject or a thin layer cytological sample of other body tissue or organ. In certain embodiments, the sample comprises a peripheral blood sample, tumor tissue or suspected tumor tissue, a thin layer cytological sample, a fine needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample, a paraffin embedded tissue sample. In other embodiments, the sample is an extract or processed sample produced from any of a peripheral blood sample, a tumor tissue or a suspected tumor tissue, a thin layer cytological sample, a fine needle aspirate sample, a bone marrow sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample or a paraffin embedded tissue sample.

The term "sample stability" as used herein generally refers to the stability of the analyte in the biological fluid or tissue sample to handling conditions that the collected samples are anticipated to experience. Sample stability may be measured as the conditions that still permit values to be measured within 75-125% accuracy relative to freshly collected samples. For example, sample stability may be evaluated at −20° C. and −80° C. over time periods equal to a typical storage period, at RT or 4° C. over a time period equal to the typical sample preparation and analytical run times, at −20° C., 4° C. and RT over a time period equal to the typical shipping period, or through freeze-thaw cycles that may be experienced.

The term "specificity" as used herein generally refers to the ability of the assay to detect antibodies that react with a specific protein. For example, specificity may refer to a proportional detection response with the specific analyte (e.g., AvPAL or variant thereof), while response to a non-specific protein (e.g., not AvPAL or variant thereof) should be below the LOD. The proportional response may be evaluated against a correlation coefficient R value greater than or equal to 0.98. When used in connection with an enzyme-linked immunosorbant assay (ELISA) method to, e.g., detect anti-AvPAL antibodies, specificity refers to the ability to detect antibodies that react with a specific protein (e.g., rAvPAL-PEG or AvPAL, or variants thereof), and when used in connection with an ELISA method to detect rAvPAL-PEG or variants thereof, specificity refers to the ability to detect specific analyte (e.g., rAvPAL-PEG or AvPAL, or variants thereof).

As used herein, the terms "subject" and "patient" are used interchangeably. As used herein, a subject is preferably a mammal such as a non-primate (e.g., cows, pigs, horses, cats, dogs, rats, etc.) or a primate (e.g., monkey and human), most preferably a human. In one embodiment, the subject is a mammal, preferably a human, having been administered a PAL enzyme, such as AvPAL or rAvPAL, or variants thereof (e.g., rAvPAL_C503S, rAvPAL_C565S, rAvPAL_C565SC503S) and/or any derivatives thereof (e.g., rAvPAL-PEG, rAvPAL-PEG_C503S, rAvPAL-PEG_C565SC or rAvPAL-PEG_C565SC503S). In some embodiments of the methods and kits provided herein, the patient has a disease or symptom related thereto that is associated with elevated phenylalanine levels, such as HPA or PKU (e.g., classic PKU, severe PKU, moderate PKU or any subpopulation thereof), or cancer. In some embodiments, the patient is a patient receiving EST (e.g., rAvPAL or rAvPAL-PEG) for elevated phenylalanine levels (e.g., a patient with PKU). In other embodiments of the methods and kits provided herein, the patient is a patient undergoing cancer therapy (e.g., using rAvPAL or rAvPAL-PEG). In yet other embodiments of the methods and kits provided herein, the patient is a pregnant female or an infant (e.g., age 0 to about 36 months). In another embodiment of the methods and kits provided herein, the patient is administered a low or modified protein diet, or a low or modified phenylalanine diet in combination with an AvPAL or rAvPAL variant thereof, such that plasma phenylalanine are decreased, e.g., by at least about 25%. See, e.g., U.S. Pat. Nos. 7,531,341 and 7,534,595 for further information on the management of patient populations with elevated phenylalanine levels (e.g., HPA and PKU) with a PAL or PAL-PEG (e.g., AvPAL or rAvPAL-PEG, or any variant thereof), which, in certain embodiments, can be used in conjunction with the methods and kits provided herein. See also U.S. Pat. Nos. 7,560,263 and 7,537,923 for further information on the management of patient populations with cancer (e.g., HPA and PKU) with a PAL or PAL-PEG (e.g., AvPAL or rAvPAL-PEG, or any variant thereof), which, in certain embodiments, can be used in conjunction with the methods and kits provided herein.

As used herein, the term "tag" and "label" are used interchangeably and refer to any type of moiety that is attached to an antibody or antigen binding fragment thereof, or other polypeptide used in the methods provided herein. The term "detectable" or "detection" with reference to an antibody or tag refers to any antibody or tag that is capable of being visualized or wherein the presence of the antibody or tag is otherwise able to be determined and/or measured (e.g., by quantitation). Non-limiting examples of a detectable tag include fluorescent or other chemiluminescent tags, and tags that can be amplified and quantitated using PCR. In certain embodiments, the secondary antibody used in the methods provided herein is a biotinylated secondary antibody that is used in combination with a labeled streptavidin.

As used herein, the term "therapy" refers to any protocol, method and/or agent that can be used in the prevention, management, treatment and/or amelioration of disease (or symptom related thereto) associated with elevated phenylalanine levels (e.g., PKU) or cancer. In certain embodiments, the terms "therapies" and "therapy" refer to a biological therapy, supportive therapy, and/or other therapies useful in the prevention, management, treatment and/or amelioration of a disease associated with elevated phenylalanine levels (e.g., PKU) or cancer known to one of skill in the art such as medical personnel.

The term "tissue" as used herein refers to tissues that are obtained from a mammal, e.g., human. For example, a tissue may be from a biopsy sample, surgically removed tissue, or postmortem collection. Furthermore, the tissue may be homogenized and extracted to isolate the enzyme or antibodies from the tissue.

As used herein, the terms "treat," "treatment" and "treating" refer to the reduction or amelioration of the progression, severity, and/or duration of a disease (or symptom related thereto) associated with elevated phenylalanine levels (e.g., PKU) or cancer resulting from the administration of one or more therapies, including, but not limited to, the administration of a PAL, such as an AvPAL (or variant thereof) and derivatives thereof (e.g., a pegylated AvPAL or a pegylated AvPAL variant thereof).

The term "variant" as used herein refers to a polypeptide sequence that contains at least one amino acid substitution, deletion, or insertion in the coding region relative to the original polypeptide coding domains. Variants retain the biological activity of the naturally occurring polypeptide. For example, it is contemplated that an AvPAL enzyme used in the methods provided herein may be the naturally occurring enzyme or may comprise one or more amino acid changes from the naturally occurring enzyme, but retains the biological activity of the enzyme (i.e., conversion of phenylalanine to ammonia and trans-cinnamic acid). In certain embodiments, the enzyme comprises ten or less, five or less, four or less, three or less, two or less or one amino acid change(s) from the naturally occurring enzyme. Specific AvPAL variants that can be used in the methods and kits provided herein, include rAvPAL_C503S, rAvPAL_C565S, rAvPAL_C565SC503S (or derivatives, such as pegylated forms, thereof), and are described elsewhere herein, as well as in U.S. Pat. Nos. 7,531,341; 7,534,595; 7,537,923 and 7,560,263.

DETAILED DESCRIPTION

Provided herein are methods of detecting the presence of a pegylated enzyme, an enzyme-specific antibody (e.g., a neutralizing antibody or of a particular isotype), or a polyethylene glycol (PEG)-specific antibody in a sample, such as a bodily fluid or tissue of a patient. In certain embodiments, the methods provided herein are useful for the detection and/or measurement of therapeutic enzymes and antibodies associated with administration of such therapeutic enzymes, including the use of a PAL (or any variant or derivative thereof), for example, in a patient receiving the PAL (e.g., an AvPAL or rAvPAL-PEG) during the course of EST for elevated phenylalanine levels (e.g., phenylketonuria) or cancer therapy. Also provided are kits for carrying our said methods. In some embodiments, the assays and methods provided herein are used to detect or otherwise measure the amount of a rAvPAL-PEG and AvPAL-specific antibodies in a body fluid from a mammal, such as a human. In some embodiments of the methods and kits provided herein, the terms AvPAL and rAvPAL can be used interchangeably.

Production and Purification of Prokaryotic PAL

In certain embodiments, prokaryotic PAL or biologically active fragment, mutant variant or analog thereof are used in the methods described herein. Such prokaryotic PALs can be expressed using any method known in the art.

For example, in certain embodiments, recombinant prokaryotic PAL or a biologically active fragment, mutant, variant or analog thereof is over-expressed, with or without an N-terminal tag (e.g., octahistidyl-tag), in a vector, such as pIBX1 (Su, et al., *Appl. Environ. Microbiol.* 62:2723-2734 (1996)) or pET28a (Invitrogen) with an inducible promoter such as with IPTG (isopropyl-beta-D-thiogalactopyranoside), in *E. coli* BLR(DE3)/pLysS (Novagen) or *E. coli* BL21(DE3)/pLysS (Invitrogen) cells. Seed culture for a bioreactor/fermenter is grown from a glycerol stock in shake flasks. Such seed culture is then used to spike into a controlled bioreactor in fed-batch mode. Glucose is supplemented and pH is controlled with base (NH4OH) and agitation is up to 1200 rpm. $O_2$ feed keeps dissolved oxygen to greater than 20%. The cells are grown at a temperature of 37° C. until reaching an $OD_{600}$ of 70-100 (~22-25 hrs) and then induced with 0.4 mM IPTG. The temperature is reduced to 30° C. and grown until activity change is <0.1 IU/mL (approximately 40-48 hrs and an $OD_{600}$ typically of 200). Cell culture media is typically defined and composed of yeast extract protein, peptone-tryptone, glucose, glycerol, casamino acids, trace salts and phosphate buffering salts. The recombinant prokaryotic PAL product or biologically active fragment, mutant, variant or analog thereof is produced intracellularly and not secreted. The bacteria are harvested by continuous centrifugation (Alfa-Laval, Can, Ceba, or equivalent).

Purification of prokaryotic PAL or a biologically active fragment, mutant, variant or analog thereof may also be accomplished using any method known in the art. In one embodiment, a transformed cell mass is grown and ruptured leaving crude recombinant enzyme. Exogenous materials are normally separated from the crude bulk to prevent fouling of the columns. Chromatographic purification is conducted using one or several chromatographic resins. Subsequently, the purified protein is formulated into a buffer designed to provide stable activity over an extended period of time. In another embodiment, the method to purify the prokaryotic PAL or biologically active fragment, mutant, variant or analog thereof comprises: (a) lysis of the bacteria containing recombinant prokaryotic PAL or biologically active fragment, mutant, variant or analog thereof using a pressure homogenizer (but potentially by other physical means such as glass bead lysis); (b) heat treatment; (c) clarification of this lysate using a second continuous centrifugation step and/or depth filtration (as with Cuono Zeta Plus or Maximizer, Pall Filtron, or Millipore Millistak or Opticao filters); (d) passage through a charcoal filtration step (as with Millipore Millistak 40AC); (e) passage through a final filtration step (as with a Sartorious Sartopore 0.2 µm filter); (f) passage over a butyl hydrophobic interaction chromatography (as in Toyopearl Butyl 650M from Tosoh Biosciences); (g) passage over a Q ion exchange column (as in a Macroprep High Q from BioRad); and (h) recovery of final product by buffer exchange with tangential flow filtration (as with a Sartorious Hydrosart or PES 100 kDa membrane). Those skilled in the art readily appreciate that one or more of the chromatography steps may be omitted or substituted, or that the order of the chromatography steps may be changed within the scope of methods provided herein. Finally, appropriate sterilizing steps may be performed as desired.

Variants

In certain embodiments, the prokaryotic PAL is AvPAL (or a biologically active fragment, mutant, variant or analog thereof, including derivatives thereof). The AvPAL may be prepared for use in a variety of applications, including EST for elevated phenylalanine levels (e.g., PKU) or for cancer therapy. AvPAL or AvPAL fragments include the full-length enzyme, or any variant, fragment or modification thereof that retains phenylalanine convertase activity (i.e., conversion of phenylalanine to ammonia and trans-cinnamic acid). Pegylated derivatives thereof may also be used (e.g., a pegylated AvPAL or a biologically active fragment, mutant, variant or analog thereof).

Full-length AvPAL can be isolated from natural sources (e.g., purified from *Anabaena variabilis* infected cells) or prepared using recombinant techniques, such as those described elsewhere herein. For example, a general strategy to generate recombinant full-length AvPAL or variants, fragments or modifications thereof that retain phenylalanine convertase activity is to amplify the coding region of interest from the AvPAL genomic DNA or cDNA by PCR, clone the PCR product into a prokaryotic expression vector, transfect the prokaryotic expression vector into bacterial cells, e.g., *E. coli* cells, and purify the AvPAL proteins using standard procedures (see, e.g., Examples 1 and 2 herein, as well as U.S. Pat. Nos. 7,531,341; 7,534,595; 7,537,923 and 7,560,263). In certain embodiments, the AvPAL has the amino acid sequence SEQ ID NO:4 (FIG. 2B).

Amino acid sequence variants of the AvPAL polypeptide can be, for example, substitutional, insertional or deletion variants. Deletion variants lack one or more residues of the native AvPAL, which are not essential for function and/or immunogenic activity. Insertional mutants typically involve the addition of material at a non-terminal point in the polypeptide. This may include the insertion of an immunoreactive epitope or simply a single residue. Terminal additions are additions of amino acid sequences at either the N- or C-terminus of the AvPAL. Terminal additions can be used to improve the biophysical characteristics of AvPAL and/or simplify its purification. Peptide additions include, for example and not for limitation, HIS (e.g., 6 or 12), TAT, FLAG™, HA, c-Myc, VSV-G, V5, S-peptide, and HSV. Protein additions include, for example, GFP, MBP, and GST.

Substitutional variants typically exchange one amino acid of the naturally occurring AvPAL for another at one or more sites, and may be designed to modulate one or more properties of the AvPAL, such as stability against proteolytic cleavage, without the loss of other functions or properties. Substitutions of this kind preferably are conservative, i.e., one amino acid is replaced with one of similar shape and charge. In certain embodiments, the enzyme comprises ten or less, five or less, four or less, three or less, two or less or one amino acid change(s) from the naturally occurring enzyme.

Variants may be substantially homologous or substantially identical to the naturally occurring AvPAL. In the context of two nucleic acids or polypeptides, substantially homologous generally refers to two or more sequences or subsequences that have at least 40%, 60%, 80%, 90%, 95%, 96%, 97%, 98% or 99% nucleotide or amino acid residue identity, when compared and aligned for maximum correspondence, as measured using sequence comparison algorithms well known in the art or by visual inspection.

Preferred variants are those variants of AvPAL that retain at least some of the biological activity of the full-length enzyme, i.e., phenylalanine convertase activity. Skilled artisans may easily design polypeptides comprising biologically active variants, fragments, or modifications of the naturally occurring AvPAL, which possess the same or similar biological activity to the naturally occurring full-length enzyme.

Particularly preferred variants are those variants of AvPAL in which one or more cysteine residues, e.g., at positions 64, 235, 318, 424, 503 and 565 of AvPAL, are replaced by serine residues, as described elsewhere herein (see, e.g., U.S. Pat. Nos. 7,531,341; 7,534,595; 7,537,923 and 7,560,263). In certain embodiments, the AvPAL variant has the amino acid sequence SEQ ID NO:7 (FIG. 3A), SEQ ID NO:8 (FIG. 3B), SEQ ID NO:9 (FIG. 3C) or SEQ ID NO:10 (FIG. 3D). In specific embodiments, the variant is the AvPAL double cysteine mutant, AvPAL_S565SC503S, in which the cysteine residues at positions 503 and 565 of AvPAL are replaced by serine residues (SEQ ID NO:11; FIG. 3E).

In any of the methods and kits provided herein, an AvPAL or an AvPAL variant thereof (including pegylated forms) can be used.

Pegylated Prokaryotic PAL Variants

Macromolecule chemical modification can be performed in a non-specific fashion (leading to mixtures of derivatized species) or in a site-specific fashion (based on wild-type macromolecule reactivity-directed derivatization and/or site-selective modification using a combination of site-directed mutagenesis and chemical modification) or, alternatively, using expressed protein ligation methods (Hofmann, et al., *Curr. Opin. Biotechnol.* 13(4):297-303 (2002)). In certain embodiments, chemical modification is used to reduce immunogenicity. In certain embodiments, the prokaryotic PAL variant comprises a water-soluble polymer (i.e., polyethylene glycol (PEG)). Pegylation is a demonstrated method to reduce immunogenicity of proteins (Bhadra, et al., *Pharmazie* 57(1):5-29 (2002)), but glycosylation and other chemical derivatization procedures, using modification with phosphorylation, amidation, carboxylation, acetylation, methylation, creation of acid-addition salts, amides, esters, and N-acyl derivatives are also possible (Davis, *Science* 303:480-482 (2004)). Methods for pegylating PAL proteins and for determining the optimal degree of pegylation are described in U.S. Pat. No. 7,553,653).

A series of different pegylation reactions on PAL, using a range of PEG chemical reagent to PAL protein ratios, can provide PEG-PAL derivatives for each modification method. The optimal degree of pegylation can be determined based upon the residual activity obtained for each derivatized PAL species using the absorbance assay in combination with PAGE and native gel analysis to determine the extent of PEG derivatization. After initial ranges of optimal modification are determined, comparative kinetic analysis (including Vmax and Km determinations, binding constants of substrates, proteolytic stability, pH dependence of activity, temperature-dependence of activity) and immunoreactivity of optimal PEG-PAL species can be determined by ELISA, immunoprecipitation, and Western blot. Protein engineering can also be used to generate the most favorable PAL mutant for pegylation using the optimal derivatization conditions; by minimizing the size of the PAL protein and only modifying the most antigenic regions of the PAL surface, cost of PEG modification will be reduced while at the same time retaining the maximum amount of enzymatic activity and minimum amount of immunogenicity. Similarly, site-specific pegylation can be used to provide enzyme derivatives.

Other chemical modifications such as phosphorylation or other chemical modification of lysine, arginine, and/or cysteine residues can be used to mask immunogenic regions and/or proteolytic sensitive regions. Such chemical modifications include the polymer addition method of Bednarsaki and the Altus Corporation cross-linking method for improving PAL stability, reducing immunogenicity, and improving protease resistance are representative examples. Bednarsaki demonstrated that polymer addition improves protein temperature stability (Wang, et al., *J. Am. Chem. Soc.* 114(1): 378-380 (1992)), and Altus Corporation has found that glutaraldehyde cross-linking improves enzyme stability.

To discover if the in vivo therapeutic half-life of a protein such as PAL would benefit from pegylation, a variety of different PEG:PAL conjugates are synthesized, characterized in vitro and tested in vivo for phenylalanine reduction. In order to both optimize the potential effects of pegylation and to identify the preferred sites of PEG attachment, a design strategy is employed wherein polymer length, conformation, and the degree of PEG attachment is varied.

Methods for preparing the pegylated PAL for use in the therapies or other methods provided herein generally comprise the steps of (a) reacting PAL with PEG under conditions whereby PAL becomes attached to one or more PEG groups, and (b) obtaining the reaction product(s). Because the specific sites of PAL modification might significantly alter the intrinsic activity of the conjugate, different types and amounts of PEG were explored. The chemistry used for pegylation of PAL was the acylation of the primary amines of PAL using the NHS-ester of methoxy-PEG (O—[(N-Succinimidyloxycarbonyl)-methyl]-O'-methylpolyethylene glycol). Acylation with methoxy-PEG-NHS or methoxy-PEG-SPA results in an amide linkage that eliminates the charge from the original primary amine.

The present methods provide for a substantially homogenous mixture of polymer:protein conjugate. "Substantially homogenous" as used herein means that only polymer: protein conjugate molecules are observed. The polymer: protein conjugate has biological activity and the present "substantially homogenous" pegylated PAL preparations provided herein are those which are homogenous enough to display the advantages of a homogenous preparation, e.g., ease in clinical application in predictability of lot to lot pharmacokinetics.

The polymer molecules contemplated for use in the pegylation approaches described herein may be selected from among water-soluble polymers or a mixture thereof. The water-soluble polymer may be selected from the group consisting of, for example, polyethylene glycol, monomethoxy-polyethylene glycol, dextran, poly-(N-vinyl pyrrolidone), propylene glycol homopolymers, a polypropylene oxide/ethylene oxide co-polymer, polyoxyethylated polyols (e.g., glycerol), HPMA, Fleximer™, and polyvinyl alcohol, mono-(C1-C10)alkoxy-PEG, aryloxy-PEG, tresyl monomethoxy PEG, PEG propionaldehyde, bis-succinimidyl carbonate PEG, cellulose, or other carbohydrate-based polymers. The polymer selected should be water-soluble so that the protein to which it is attached does not precipitate in an aqueous environment, such as a physiological environment. The polymer may be branched or unbranched. Preferably, for therapeutic use of the end-product preparation, the polymer will be pharmaceutically acceptable.

In specific embodiments, the water-soluble polymer is PEG. As used herein, PEG is meant to encompass any of the forms of PEG that have been used to derivatize other proteins, such as mono-(C1-C10)alkoxy- or aryloxy-polyethylene glycol.

The proportion of PEG molecules to protein molecules will vary, as will their concentrations in the reaction mixture. In general, the optimum ratio (in terms of efficiency of reaction in that there is no excess unreacted protein or polymer) will be determined by the molecular weight of the PEG selected and on the number of available reactive groups (typically ε amino groups) present. As relates to molecular weight, in general, the higher the molecular weight of the polymer used, the fewer number of polymer molecules which may be attached to the protein. Similarly, branching of the polymer should be taken into account when optimizing these parameters. Generally, the higher the molecular weight (or the more branches) the higher the polymer: protein ratio. Several different linear PEG polymer lengths including, but not limited to, 5 kDa and 20 kDa, conjugates of two-armed branched PEG polymers, including, but not limited to, 10 kDa and 40 kDa. In general, for the pegylation reactions contemplated herein, the preferred average molecular weight is about 2 kDa to about 100 kDa (the term "about" indicating +/−1 kDa). More preferably, the average molecular weight is about 5 kDa to about 40 kDa. The ratio of water-soluble polymer to PAL will generally range from 1:1 for monoPEG, 2:1 for diPEG, etc.

One or more lysine residues at or near the active site of a prokaryotic PAL variant can be introduced to enhance catalytic activity, reduce immunogenicity and/or improve biochemical stability, in part by blocking potential pegylation of other amino acid residues (e.g., tyrosine) at/near the active site of the enzyme or by blocking potential pegylation of a lysine residue important for enzyme activity. Without being bound to a particular theory, it is hypothesized that a tyrosine residue at/near the active site of a prokaryotic PAL (i.e., position 78 or 314 in AvPAL) can be a site for pegylation, which reduces enzyme activity. In some embodiments, one or more amino acid residues at/near the active site of the prokaryotic PAL, which are not required for enzyme activity, are substituted by a lysine residue.

In one embodiment, the prokaryotic PAL is AvPAL. In some embodiments, the AvPAL tyrosine residue at position 78, 314 or 419 is not accessible for pegylation. Again without being bound to a particular theory, it is hypothesized that a lysine residue of a prokaryotic PAL (i.e., position 419 in AvPAL), which is normally blocked from pegylation due to pegylation of a neighboring lysine residue PAL (i.e., position 413 in AvPAL), can be a site for pegylation, which reduces substrate binding and/or catalytic activity. In some embodiments, one or more amino acid residues of the prokaryotic PAL are substituted by a lysine residue, such that a lysine residue important for the substrate binding and/or catalytic activity of the enzyme is not accessible for pegylation.

Pegylated PAL enzymes are effective for decreasing in vivo phenylalanine concentrations in subjects. For instance, Examples 7-9 of U.S. Pat. No. 7,531,341, describe the effects of pegylated and nonpegylated forms of lysine mutant R91K PAL from *Rhodosporidium toruloides* (RtPAL), PAL produced by the cyanobacterium *Nostoc punctiforme* (NpPAL), and PAL produced by the cyanobacterium *Anabaena variabilis* (AvPAL) on phenylalanine levels in the ENU2 or BTBR$^{enu2}$ mouse. This animal model is a homozygous mutant at the phenylalanine hydroxylase gene (PAH) locus resulting in an animal with severe hyperphenylalanemia. The high plasma phenylalanine levels make this animal the appropriate model for evaluating the ability of PAL to reduce plasma phenylalanine Administration of pegylated forms of NpPAL and AvPAL resulted in greater reduction in phenylalanine in the ENU2 mice as compared to unpegylated NpPAL and AvPAL, respectively. Such effects were maintained for NpPAL upon weekly injections over a ten-week period. These results show that pegylation of PAL from the cyanobacteria, *Nostoc punctiforme* and *Anabaena variabilis*, is essential in reducing phenylalanine levels in PKU affected mice.

Similarly, certain pegylated AvPAL variants also effective for decreasing in vivo phenylalanine concentrations in subjects and also results in lower concentrations of anti-AvPAL antibodies. For instance, Example 14 of U.S. Pat. No. 7,534,595 describes the effect of serine substitution of the cysteine residues (e.g., at positions 503 and 565) in the AvPAL polypeptide on phenylalanine levels in ENU2 mice. The administration of the pegylated AvPAL double cysteine mutant AvPAL_C565SC503S resulted in a reduction in plasma phenylalanine that was comparable to that achieved with pegylated wild-type AvPAL. In addition, the anti-PAL antibody titers were lower in animals injected with pegylated AvPAL variant as compared to pegylated wild-type AvPAL. These results show that a pegylated AvPAL variant has (1) in vivo PAL enzyme activity that is comparable to the pegylated wild-type AvPAL, and (2) has reduced immunogenicity compared to the pegylated wild-type AvPAL.

In certain embodiments of the methods provided herein, the AvPAL is an AvPAL variant, wherein the cysteine residue at position 503 of AvPAL has been substituted with a serine residue (rAvPAL-PEG_C503S; SEQ ID NO:9). In some embodiments of the methods provided herein, the AvPAL is an AvPAL variant, wherein the cysteine residue at position 565 of AvPAL has been substituted with a serine residue (rAvPAL-PEG_C565S; SEQ ID NO:10). In yet other embodiments of the methods provided herein, the AvPAL is an AvPAL variant, wherein the cysteine residue at positions 503 and 565 of AvPAL have been substituted with serine residues (rAvPAL_C565SC503S; SEQ ID NO:11)).

In some embodiments, the rAvPAL_C503S, rAvPALC565S or rAvPAL_C565SC503S is pegylated (rAvPAL-PEG_C503S, rAvPAL-PEG_C565S, or rAvPAL-PEG_C565SC503S, respectively).

In one embodiment, the rAvPAL-PEG_C565SC503S pegylation is achieved by reacting the AvPAL variant with NHS-activated polyethylene glycol at a ratio of at least 1.6 polyethylene glycol per lysine residue of AvPAL variant. In one embodiment, at least 28 percent of lysine residues at positions 2, 10, 32, 145, 195, 301, 413, 493, and 522 of the rAvPAL-PEG_C565SC503S are pegylated. In another embodiment, the rAvPAL-PEG_C565SC503S pegylation is achieved by reacting the AvPAL variant with NHS-activated polyethylene glycol at a ratio of at least 2.4 polyethylene glycol per lysine residue of AvPAL variant. In some embodiments, at least 51 percent of lysine residues at positions 2, 10, 195, 413, 493, and 522 of the rAvPAL-PEG_C565SC503S are pegylated. In other embodiments, the rAvPAL-PEG_C565SC503S pegylation is achieved by reacting the AvPAL variant with NHS-activated polyethylene glycol at a ratio of 3 polyethylene glycol per lysine residue of AvPAL variant. In certain embodiments, at least 75 percent of lysine residues at positions 2, 10, 195, 493, and 522 of the rAvPAL-PEG_C565SC503S are pegylated.

Labels

In some embodiments, an assay reagent is labeled to facilitate its detection. Labels can be a substance used to directly or indirectly detect the antibody or other protein (e.g., streptavidin) that the label is attached to. In certain embodiments, the label is the antibody or other protein itself or, alternatively, the label may be covalently or non-covalently linked to the antibody or other protein. In certain embodiments, labels are used in order to follow or track the given antibody or other protein, for example, to determine its presence or amount.

A label or a detectable moiety is a composition detectable by spectroscopic, photochemical, biochemical, immunochemical, chemical, or other physical means. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), or luminescent or bioluminescent labels (such as Europium, Vanadium, etc.), paramagnetic atoms, electrochemiluminescent labels (such as Ru-based labels in conjunction with substrates, etc.), and the like.

In some embodiments, an assay reagent is labeled to facilitate its capture. A capture moiety is a composition that is capable of being specifically bound by another composition that is attached or linked to a solid support. An assay reagent can be labeled through the use of affinity labels (such as biotin, avidin, etc.) for which specific and selective ligands are available, haptens and proteins for which antisera or monoclonal antibodies are available, and nucleic acid molecules with a sequence complementary to a target. Procedures for accomplishing such labeling are described in Sternberger et al., *J. Histochem. Cytochem.* 18:315 (1970); Bayer et al., *Meth. Enzym.* 62:308 (1979); Engval et al., *Immunol.* 109:129 (1972); Goding, *J. Immunol. Meth.* 13:215 (1976)). The solid support can be a filter, plate, membrane or bead, and the like.

In some embodiments of the methods and kits provided herein, labels are used which may be detected directly, e.g., on the basis of a physical or chemical property of the label (e.g., optical absorbance, fluorescence, phosphorescence, chemiluminescence, electrochemiluminescence, refractive index, light scattering, radioactivity, magnetism, catalytic activity, or chemical reactivity). Examples of directly detectable labels include, but are not limited to, radioactive labels, fluorescent labels, luminescent labels, enzyme labels, chemiluminescent labels, electrochemiluminescent labels, phosphorescent labels, light scattering or adsorbing particles (e.g., metal particles, gold colloids, silver colloids), magnetic labels and the like.

Examples of labels suitable for use in the methods provided herein include, but are not limited to, radioactive labels (e.g., $^{32}$P), fluorophores (e.g., fluorescein), electron-dense reagents, enzymes (e.g., as commonly used in an ELISA), biotin, digoxigenin, or haptens as well as proteins which can be made detectable, e.g., by incorporating a radiolabel into the hapten or peptide, or used to detect antibodies specifically reactive with the hapten or peptide. Also contemplated are a nanotag, a molecular mass bead, a magnetic agent, a nano- or micro-bead containing a fluorescent dye, a quantum dot, a quantum bead, a fluorescent protein, dendrimers with a fluorescent label, a micro-transponder, an electron donor molecule or molecular structure, or a light reflecting particle.

For example, labels contemplated for use in the methods provided herein include, but are not limited to, fluorescent dyes (e.g., fluorescein isothiocyanate, Texas red, rhodamine, and the like), radiolabels (e.g., $^3$H, $^{125}$I, $^{35}$S, $^{14}$C or $^{32}$P), enzymes (e.g., horse radish peroxidase, alkaline phosphatase and others commonly used in an ELISA), biotin, and colorimetric labels such as colloidal gold, colored glass or plastic beads (e.g., polystyrene, polypropylene, latex, etc.), and luminescent or chemiluminescent labels.

The label may be coupled directly or indirectly to the desired component of the assay. In specific embodiments, the label is covalently bound to the biopolymer (e.g., antibody or protein) using an isocyanate or N-hydroxysuccinimide ester reagent for conjugation of an active agent. In some embodiments, the bifunctional isocyanate reagents provided herein can be used to conjugate a label to a biopolymer to form a label biopolymer conjugate without an active agent attached thereto. The label biopolymer conjugate may be used as an intermediate for the synthesis of a labeled conjugate or can be used to detect the biopolymer conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand then binds to another molecule (e.g., Streptavidin) molecule, which is either inherently detectable or covalently bound to a signal system, such as a detectable enzyme, a fluorescent compound, or a chemiluminescent compound, or to a solid support, such as a filter, a plate, a membrane or a bead, and the like.

The compounds useful in the method provided herein can also be conjugated directly to signal-generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, i.e., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), europium, Texas Red, nicotinamide adenine dinucleotide, flavin adenine dinucleotide, etc. Chemiluminescent compounds suitable for use as labels include, but are not limited to, Europium (Eu), Samarium (Sm), luciferin and 2,3-dihydrophthalazinediones, e.g., luminol. Electrochemiluminescent compounds suitable for use as labels include, but are not limited to, MSD TAG, MSD Sulfo-TAG, BV-TAG, and BV-TAG Plus. For a review of various labeling or signal producing systems that can be used in the methods provided herein, see U.S. Pat. No. 4,391,904.

Detection Methods and Kits

Where the label is radioactive, means for detection include a scintillation counter or photographic film, as in autoradiography. Where the label is a fluorescent label, exciting the fluorochrome with the appropriate wavelength of light and detecting the resulting fluorescence may detect it. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric labels may be detected simply by observing the color associated with the label. Other labeling and detection systems suitable for use in the methods provided herein will be readily apparent to those of skill in the art. Such labeled modulators and ligands can be used in the diagnosis of a disease or health condition.

Chemiluminescent labels may be detected by observing the light emitted upon reaction of the label with substrate. Electrochemiluminescent labels may be detected by observing the light emitted upon reaction of the label with substrate in an electrical field.

In some embodiments, the labeled compositions that can be used in the methods provided herein are linked to a solid support, including, but not limited to, filters, plates or membranes. It is further contemplated that the labeled compounds may be labeled and interact in solution. For example, the capture antibody may be labeled with a fluorescent resonance energy transfer (FRET) donor molecule and the target molecule is labeled with a FRET acceptor molecule such that the molecules are in proximity when binding occurs. Alternatively, the target molecule may be labeled with the FRET donor and the antibody molecule the FRET acceptor. Another possibility is to separate quenching and fluorescent molecule both present on the antibody or target when target and antibody hybridize. The target molecule is only close enough for its label to emit if it is interacting with the reagent. This produces a system where the molecule only emits when it interacts with the reagent (direct monitoring). A narrow band pass filter can be used to block all wavelengths except that of the molecule's label. FRET molecule pairs are commercially available in the art (e.g., from Invitrogen), and may be used according to the manufacturer's protocol. FRET emissions are detected using optical imaging techniques, such as a CCD camera.

Another method of detecting the antibody-antigen interactions is to label it with an electron donor. This donor label would give electrons to an electrical contact to which the reagent is bound. See, for example, Ghindilis, *Biochem Soc Trans.* 28:84-9, (2000) and Dai et al., *Cancer Detect Prev.* 29:233-40 (2005), which describe enzymes useful in and methods for electro immunoassays. The electron contact would then be read by an A to D (analog to digital) converter and quantified. The higher the electron count the more interactions took place.

One embodiment of a label capable of single molecule detection is the use of plasmon-resonant particles (PRPs) as optical reporters, as described in Schultz et al., *Proc. Natl. Acad. Sci. USA* 97:996-1001 (2000), incorporated herein by reference. PRPs are metallic nanoparticles, typically 40-100 nm in diameter, which scatter light elastically with remarkable efficiency because of a collective resonance of the conduction electrons in the metal (i.e., the surface plasmon resonance). The magnitude, peak wavelength, and spectral bandwidth of the plasmon resonance associated with a nanoparticle are dependent on the particle's size, shape, and material composition, as well as the local environment. By influencing these parameters during preparation, PRPs can be formed that have scattering peak anywhere in the visible range of the spectrum. For spherical PRPs, both the peak scattering wavelength and scattering efficiency increase with larger radius, providing a means for producing differently colored labels. Populations of silver spheres, for example, can be reproducibly prepared for which the peak scattering wavelength is within a few nanometers of the targeted wavelength, by adjusting the final radius of the spheres during preparation. Because PRPs are bright, yet nanosized, they are used as indicators for single-molecule detection; that is, the presence of a bound PRP in a field of view can indicate a single binding event.

In one exemplary embodiment, the assay device is a lateral flow test strip, optionally encased in a housing. A first labeled antibody to an AvPAL is in solution, while a second antibody to the AvPAL is immobilized on the test strip. When a patient sample containing an AvPAL is contacted with both antibodies, an antibody-target-antibody sandwich complex is formed, and the resulting complex, which is immobilized on the solid support, is detectable by virtue of the label. The test strip is then inserted into a reader, where the signal from the label in the complex is measured. The outcome may be either a positive or negative result, or a quantitative determination of the concentration of an AvPAL in the sample, which is correlated with a result indicative of a risk or presence of a disease or disorder. The entire procedure may be automated and/or computer-controlled. Alternatively, the test strip may be read visually by comparison to a visual standard of the appropriate color. This test provides similar clinically relevant information as an AvPAL ELISA, but in significantly less time and at the point of care.

Antigen-antibody complexes may also be detected using nanoparticle-derived techniques. See, for example, Ao et al., *Anal Chem.* 78:1104-6 (2006), which describes gold nanoparticle quenching, Tang et al., *Biosens Bioelectron.* 2005 Nov. 30, which describes SiO(2)/Au nanoparticle surfaces in antibody detection, and Lieu et al., *J Immunol Methods.* 307:34-40 (2005), which describes silicon dioxide nanoparticles containing dibromofluorescein for use in solid substrate-room temperature phosphorescence immunoassay (SS-RTP-IA).

Kits are also provided herein. The kit can contain one or more reagents identified in the various methods provided herein. For example, in one embodiment, the kit comprises an AvPAL, optionally linked to a detectable label or a capture moiety, and/or an antibody standard that specifically binds to the AvPAL, and/or an AvPAL standard containing a known quantity of an AvPAL. In another embodiment, the kit comprises an AvPAL substrate, and/or an AvPAL standard containing a known quantity of an AvPAL, and/or an antibody standard that specifically binds to, and neutralizes the enzymatic activity of, the AvPAL. In another embodiment, the kit comprises an AvPAL, optionally linked to a detectable label, and/or an antibody that specifically binds to antibodies of IgG, IgA, IgE, IgM or IgD isotype, and/or an IgG, IgA, IgE, IgM or IgD antibody standard that specifically binds to the AvPAL, and/or an AvPAL standard containing a known quantity of an AvPAL. Other components of the kits may optionally include reagents and/or instructions for carrying out the any of the methods provided herein, e.g., reagents used to acidify or to neutralize rAvPAL-PEG or variants thereof, as described elsewhere herein.

Spectral absorption labels may also be used. A possible methodology for detection would be to mix into the bead polymer different materials that absorb and pass different spectra of light. Each different type of bead could be detected by passing a multi-spectral light though the bead and detecting which spectra are absorbed.

Antibody Production

Antibodies for use in the methods and kits provided herein include, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab')$_2$ fragments, disulfide-linked Fvs (sdFv), anti-idiotypic (anti-Id) antibodies, and epitope-binding fragments of any of the above. In specific embodiments, the first and/or second antibody of the methods provided herein is a monoclonal antibody.

In particular, antibodies for use in the methods and kits provided herein include immunoglobulin molecules and immunologically active portions of immunoglobulin molecules, i.e., molecules that contain an antigen binding site that immunospecifically binds to a target (such as AvPAL or rAvPAL-PEG or a variant thereof). The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule. In specific embodiments, the first and/or second antibody of the methods provided herein is an IgG antibody.

Variants and derivatives of antibodies include antibody fragments that retain the ability to specifically bind to an epitope. Preferred fragments include Fab fragments (an antibody fragment that contains the antigen-binding domain and comprises a light chain and part of a heavy chain bridged by a disulfide bond); Fab' (an antibody fragment containing a single anti-binding domain comprising an Fab and an additional portion of the heavy chain through the hinge region); F(ab')$_2$ (two Fab' molecules joined by interchain disulfide bonds in the hinge regions of the heavy chains; the Fab' molecules may be directed toward the same or different epitopes); a bispecific Fab (a Fab molecule having two antigen binding domains, each of which may be directed to a different epitope); a single chain Fab chain comprising a variable region, also known as, a sFv (the variable, antigen-binding determinative region of a single light and heavy chain of an antibody linked together by a chain of 10-25 amino acids); a disulfide-linked Fv, or dsFv (the variable, antigen-binding determinative region of a single light and heavy chain of an antibody linked together by a disulfide bond); a camelized VH (the variable, antigen-binding determinative region of a single heavy chain of an antibody in which some amino acids at the VH interface are those found in the heavy chain of naturally occurring camel antibodies); a bispecific sFv (a sFv or a dsFv molecule having two antigen-binding domains, each of which may be directed to a different epitope); a diabody (a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes). Derivatives of antibodies also include one or more CDR sequences of an antibody combining site. The CDR sequences may be linked together on a scaffold when two or more CDR sequences are present. In certain embodiments, the antibody used in the methods and kits provided herein comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs see Pluckthun in *The*

*Pharmacology of Monoclonal Antibodies*, vol. 113, Rosenburg and Moore eds. Springer-Verlag, New York, pp. 269-315 (1994).

The antibodies may be from any animal origin including birds and mammals (e.g., human, murine, donkey, sheep, rabbit, goat, guinea pig, camel, horse, or chicken). In certain embodiments, the antibodies are human or humanized monoclonal antibodies. As used herein, "human" antibodies include antibodies having the amino acid sequence of a human immunoglobulin and include antibodies isolated from human immunoglobulin libraries or from mice that express antibodies from human genes.

In some embodiments of the methods provided herein, the first antibody and/or the second antibody is a monoclonal antibody.

Monoclonal or polyclonal antibodies for a given PAL (e.g., AvPAL), PAL variant thereof, or any pegylated PAL or PAL variant, that can be used in the methods and kits provided herein can be prepared using standard techniques known in the art, such as those described below. The term "monoclonal antibody" refers to an antibody obtained from a population of homogenous or substantially homogeneous antibodies, wherein each monoclonal antibody will typically recognize a single epitope on the antigen. In certain embodiments, a "monoclonal antibody," as used herein, is an antibody produced by a single hybridoma or other cell, wherein the antibody immunospecifically binds to only a given epitope of a PAL (e.g., AvPAL) or variant thereof as determined, e.g., by ELISA or other antigen-binding or competitive binding assay known in the art. The term "monoclonal" is not limited to any particular method for making the antibody. For example, monoclonal antibodies may be made by the hybridoma method as described in Kohler et al.; Nature, 256:495 (1975) or may be isolated from phage libraries using techniques known in the art, for example. Other methods for the preparation of clonal cell lines and of monoclonal antibodies expressed thereby are well known in the art (see, for example, Chapter 11 in: *Short Protocols in Molecular Biology*, (2002) 5th Ed., Ausubel et al., eds., John Wiley and Sons, New York). "Polyclonal antibodies" as used herein refers to an antibody population generated in an immunogenic response to a protein having many epitopes and thus includes a variety of different antibodies directed to the same and to different epitopes within the protein. Methods for producing polyclonal antibodies are known in the art (See, e.g., see, for example, Chapter 11 in: *Short Protocols in Molecular Biology*, (2002) 5th Ed., Ausubel et al., eds., John Wiley and Sons, New York).

Antibodies that immunospecifically bind to, e.g., a PAL, such as AvPAL, or variant thereof, can be produced by any method known in the art for the synthesis of antibodies. The practice of the methods provided herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, N.Y.; Ausubel et al., *Current Protocols in Molecular Biology*, John Wiley & Sons (1987 and annual updates); *Current Protocols in Immunology*, John Wiley & Sons (1987 and annual updates); Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

Polyclonal antibodies that immunospecifically bind to an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N.Y., 1981).

Methods for producing and screening for specific antibodies using hybridoma technology are routine and well known in the art. Briefly, mice can be immunized with a given PAL (e.g., AvPAL) or variant thereof antigen and once an immune response is detected, e.g., antibodies specific for the PAL (e.g., AvPAL) antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution.

Additionally, a RIMMS (repetitive immunization multiple sites) technique can be used to immunize an animal (Kilptrack et al., 1997 *Hybridoma* 16:381-9). The hybridoma clones are then assayed by methods known in the art for cells that secrete antibodies capable of binding a polypeptide. Ascites fluid, which generally contains high levels of antibodies, can be generated by immunizing mice with positive hybridoma clones.

Antibody fragments which recognize a PAL (e.g., AvPAL) antigen may be generated by any technique known to those of skill in the art. For example, Fab and $F(ab')_2$ fragments may be produced by proteolytic cleavage of immunoglobulin molecules, using enzymes such as papain (to produce Fab fragments) or pepsin (to produce $F(ab')_2$ fragments). $F(ab')_2$ fragments contain the variable region, the light chain constant region and the CH1 domain of the heavy chain.

For example, antibodies which recognize a PAL (e.g., AvPAL) antigen can also be generated using various phage display methods. In phage display methods, functional antibody domains are displayed on the surface of phage particles which carry the polynucleotide sequences encoding them. In particular, DNA sequences encoding variable heavy (VH) and variable light (VL) domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies useful in the methods provided herein include those disclosed in Brinkman et al., 1995, *J. Immunol. Methods* 182:41-50; Ames et al., 1995, *J. Immunol. Methods* 184: 177-186; Kettleborough et al., 1994, *Eur. J. Immunol.* 24:952-958; Persic et al., 1997, *Gene* 187:9-18; Burton et al., 1994, *Advances in Immunology* 57:191-280; PCT Application No. PCT/GB91/01 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')$_2$ fragments can also be employed using methods known in the art such as those disclosed in PCT publication No. WO 92/22324; Mullinax et al., 1992, *BioTechniques* 12(6):864-869; Sawai et al., 1995, *AJRI* 34:26-34; and Better et al., 1988, *Science* 240:1041-1043.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lambda constant regions. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

Antibody Purification

Antibodies may be purified using techniques standard in the art, including, but not limited to, protein A-Sepharose, hydroxylapatite chromatography, gel electrophoresis, dialysis, or affinity chromatography. The antibody composition prepared from microbial or mammalian cells or serum can be purified using, for example, hydroxylapatite chromatography cation or anion exchange chromatography, and affinity chromatography, with affinity chromatography being the preferred purification technique. For affinity chromatography, the affinity ligand is typically the antigen, e.g., rAvPAL-PEG or AvPAL, or variant thereof, which is specifically recognized by the antibody to be purified. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62: 1-13 (1983)). Protein G is recommended for all mouse isotypes and for human γ3 (Guss et al., *EMBO J.* 5:1567-75 (1986)). The matrix to which the affinity ligand is attached is most often agarose or acrylamide, but other matrices are available. A suitable matrix to which the affinity ligand is attached is Sepharose beads. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Solid Support Materials

For the methods provided herein, the antibody, enzyme (e.g., AvPAL, rAvPAL-PEG, or any variant thereof) or PEG can be immobilized or otherwise bound to a variety of solid supports, including but not limited to filters, PVC membranes, PDVF membranes, PVC plates and other plates which bind protein, microcarriers, macro solid phase beads, magnetic beads, made out of, for example, polystyrene, nanoparticles, such as bimetallic silver-gold nanoparticles (Yan Cui et al., *J. Phys. Chem. B* 110 (9):4002-06 (2006), and polyamide membrane (PAM) sheets (Sun et al., *Analytical Letters* 34:1627-37 (2001)).

For example, microspheres with multiple fluorescent molecular fillings, different materials, surface texture, surface patterns, etc., can be utilized as identification tags. It is contemplated that either the capture antibody or the AvPAL is covalently bound to the bead and reacted against the opposite binding partner to assay the amount of AvPAL-specific antibody in serum. See, for example, Current Protocols in Immunology, Unit 6.11, 2006). Fluorescently filled microspheres are currently available from Molecular Probes, Inc. and other companies. Microspheres as small as 20 nm diameter polystyrene beads are currently available.

The antibody, enzyme (e.g., AvPAL, rAvPAL-PEG, or any variant thereof) or PEG can attached to the solid support using standard protocols in the art, e.g., as described by the manufacturer of the support, or using standard chemical crosslinking techniques known in the art. See e.g., Pierce Biotechnology, Inc. (Rockford, Ill.) crosslinking kits.

In one embodiment, antibody, enzyme (e.g., AvPAL, rAvPAL-PEG, or any variant thereof) or PEG are attached to Sepharose beads and used to purify anti-PAL enzyme antibodies, e.g., anti-AvPAL antibodies.

In other embodiments of the methods and kits provided herein, the antibody, PEG or rAvPAL-PEG or AvPAL, or variant thereof is immobilized on a solid surface. In certain embodiments, the antibody, enzyme (e.g., AvPAL, rAvPAL-PEG, or any variant thereof) or PEG is immobilized in a well of a plate with a plurality of wells, such as a multi-well plate or a multi-domain multi-well plate. The use of multi-well assay plates allows for the parallel processing and analysis of multiple samples distributed in multiple wells of a plate. Multi-well assay plates (also known as microplates or microtiter plates) can take a variety of forms, sizes and shapes (e.g., 96-, 384-, 1536-, or 9600-well plates; round- or flat-bottom multi-well plates). The methods provided herein, when carried out in standardized plate formats can take advantage of readily available equipment for storing and moving these plates as well as readily available equipment for rapidly dispensing liquids in and out of the plates (e.g., multi-well pipettes, plate washers and the like). Exemplary multi-well plate formats that can be used in the methods provided herein include those found on 96-well plates (12×8 array of wells), 384-well plates (24×16 array of wells) and 1536-well plate (48×32 array of well). Other formats that may be used in the methods provided herein include, but are not limited to, single or multi-well plates comprising a plurality of domains.

In specific embodiments of the methods and kits provided herein, solid phase supports are used for purifying, immobilizing, or otherwise carrying out assays provided herein. Examples of solid phases suitable for carrying out the methods and kits provided herein include beads, particles, colloids, single surfaces, tubes, multiwell plates, microtitre plates, slides, membranes, gels and electrodes. When the solid phase is a particulate material (e.g., beads) it is, preferably, distributed in the wells of multi-well plates to allow for parallel processing of the solid phase supports. In specific embodiments of the methods and kits provided herein, the primary capture reagents are immobilized on the solid phase supports, e.g., by non-specific adsorption, covalent attachment, or specific capture using an immobilized capture reagent that binds the primary antibody or other protein of interest. Immobilization may be accomplished by using proteins or assay reagents that are labeled with binding species that form binding pairs with immobilized capture reagents. Optionally, the antibody is immobilized on a solid phase, and contacted with a sample, and the solid phase is washed. The wash step allows for the rapid purification of the antibody (e.g., an anti-AvPAL antibody) or protein (e.g., rAvPAL-PEG} being identified from other, potentially interfering, components of the sample. Optionally, the sample is treated, for example with a lysis buffer, prior to analysis.

Assays

Sandwich-based immunoassay methods are well established in the art. See, e.g., U.S. Pat. No. 4,376,110 (David et al.); U.S. Pat. No. 4,016,043 (Schuurs et al.). Other related immunoassay formats and variations thereof which may be useful for carrying out the methods provided herein are well known in this field. See generally, E. Maggio (1980) *Enzyme-Immunoassay* (CRC Press, Inc., Boca Raton, Fla.); see also, e.g., U.S. Pat. No. 4,727,022 (Skold et al.); U.S. Pat. No. 4,659,678 (Forrest et al.); U.S. Pat. No. 4,376,110 (David et al.).

In the various methods provided herein, removing unbound sample or other reagent is optional. In other words, the unbound sample and/or other reagent may, in some embodiments, or may not, in other embodiments, be removed when performing the methods provided herein.

In certain embodiments of the various methods provided herein, the two or more of the steps are performed sequentially. In other embodiments of the methods provided herein, two or more of steps are performed in parallel (e.g., at the same time).

It is noted that any combination of the embodiments provided herein, for example, with respect to sample, patient populations, solid phase immobilization, first antibody (or other reagent), second antibody (or other reagent), labels and the like, are also contemplated in relation to any of the various methods and/or kits provided herein.

Methods and Kits to Detect a Pegylated Enzyme in a Sample

Pharmacokinetic (PK) studies are performed in mammalian species, including humans, to evaluate exposure to drug or therapeutic enzyme. As part of the evaluation of PK and toxicology studies, the exposure to drug or therapeutic enzyme (i.e., rAvPAL-PEG or variant thereof) must be evaluated.

In a first aspect, provided herein is a method of detecting the presence of a pegylated enzyme, e.g., rAvPAL-PEG or variant thereof, in a sample (e.g., a body fluid, such as plasma, or a tissue sample), said method comprising: (a) acidifying the pegylated enzyme in the sample by adding an acidification reagent; (b) neutralizing the acidified pegylated enzyme in the sample by adding a neutralization buffer; (c) contacting the sample with an immobilized first antibody that immunospecifically binds with the pegylated enzyme; (d) optionally removing unbound sample; (e) contacting the sample bound to the immobilized first antibody with a detectable second antibody, wherein the second antibody immunospecifically binds to PEG; (f) optionally removing unbound second antibody; and (g) detecting the presence of the second antibody bound to the sample; wherein detection above background of an amount of the second antibody bound to the sample, e.g., an increase in the amount of second antibody bound to the sample as compared to a control sample having no pegylated enzyme, indicates the presence of pegylated enzyme in the sample. In some embodiments, the neutralized pegylated enzyme described in (b) is introduced into a different assay buffer before contacting the immobilized first antibody described in (c).

In certain embodiments, the sample is a body fluid (e.g., blood, serum, plasma, CSF, urine or breast milk) or a tissue sample from a patient. In some embodiments, the patient is a mammal, such as a human, monkey, dog, rabbit, rat or mouse.

In an embodiment, the concentration of pegylated enzyme in the sample is determined. In one embodiment, the limit of detection is less than 5 ng/mL, or less than 3 ng/mL. In another embodiment, the limit of detection is between 5 ng/mL and 2 ng/mL, such as between 3 ng/mL and 2 ng/mL. In an embodiment, the sample is plasma, which is equal to or less than 5% or equal to or less than 2% of the volume as described in (a).

In some embodiments, the patient has elevated phenylalanine levels. In specific embodiments, the patient has been or will be administered the pegylated enzyme, for example, for EST (e.g., for PKU) or cancer therapy. In an embodiment, the pegylated enzyme is rAvPAL-PEG or a variant thereof. In one embodiment, the pegylated enzyme is rAvPAL-PEG having its cysteine residue at position 503 substituted with serine residues (rAvPAL-PEG_C503S). In another embodiment, the pegylated enzyme is rAvPAL-PEG having its cysteine residues at position 565 substituted with serine residues (rAvPAL-PEG_C565S). In yet another embodiment, the pegylated enzyme is rAvPAL-PEG having its cysteine residues at positions 503 and 565 substituted with serine residues (rAvPAL-PEG_C565SC503S). In other embodiments, the pegylated enzyme is rAvPAL-PEG_C503S, rAvPAL-PEG_C565S, rAvPAL-PEG_C565SC503S, or any combination thereof.

In one embodiment, the immunogenic epitopes of the pegylated therapeutic enzyme are exposed by acidifying the pegylated enzyme in the sample by adding an acidification reagent, and subsequently neutralizing the pegylated enzyme in the sample by adding a neutralization buffer. In one embodiment, the acidification reagent is HCl. In one embodiment, the neutralization reagent is NaOH. In another embodiment, the acidification reagent is 0.1 M glycine, pH 2.7. In some embodiments, the neutralization buffer is 0.5 M Tris-HCl, pH 8.5. In one embodiment, the acidification reagent is 0.1 M glycine, pH 2.7 and the neutralization buffer is 0.5 M Tris-HCl, pH 8.5. In another embodiment, the acidification and subsequent neutralization of the pegylated enzyme in the sample is performed before contacting the sample with the immobilized first antibody.

In another embodiment, the immunogenic epitopes of the pegylated therapeutic enzyme are exposed by denaturing the enzyme in the sample by exposure to heat, and subsequently renaturing the enzyme by cooling the sample.

In a specific embodiment, provided herein is a method to measure the amount of a pegylated therapeutic enzyme (i.e., rAvPAL-PEG or variant thereof) in a mammal (e.g., human) comprising: (a) binding an AvPAL-specific antibody to a solid support, (b) acidifying a pegylated (i.e., derivatized by polyethylene glycol) AvPAL (rAvPAL-PEG) enzyme in a body fluid (e.g., plasma) sample from the mammal by adding an acidification reagent, (c) neutralizing the acidified rAvPAL-PEG enzyme in the body fluid sample by adding a neutralization buffer, (d) capturing the acidified and neutralized rAvPAL-PEG enzyme in the body fluid sample from the mammal by contacting the body fluid sample with AvPAL-specific antibodies bound to the solid support in (a), (e) contacting the captured rAvPAL-PEG enzyme from (d) with an anti-PEG specific antibody labeled with a detectable moiety, and (f) determining the amount of rAvPAL-PEG enzyme in the body fluid sample by detecting the presence of anti-PEG specific antibody labeled with the detectable moiety. In a another embodiment, (a) the enzyme-specific antibody is bound to a solid support, (b) the pegylated enzyme is acidified in the body fluid sample by adding an acidification reagent, (c) the acidified pegylated enzyme is neutralized in the body fluid sample by adding a neutralization buffer, (d) the neutralized pegylated enzyme in the body fluid sample is captured with the enzyme-specific antibody bound to the solid support in (a), (e) the captured pegylated enzyme is contacted with an anti-PEG specific antibody labeled with a detectable moiety, and (f) the amount of captured pegylated enzyme from the body fluid sample is determined by detecting the presence of anti-PEG specific antibody labeled with the detectable moiety. In some embodiments, (b), (c) and (d) are performed in the order (b), (c), (d). In some embodiments, the neutralized pegylated enzyme in (c) is introduced into a different assay buffer performing the enzyme capture in (d).

In some embodiments, a method is provided of classifying a patient for eligibility for a pegylated enzyme therapy (e.g., initial or continued pegylated enzyme therapy) with, e.g., a rAvPAL-PEG or variant thereof, comprising: (a) providing a sample (e.g., a body fluid or tissue) from the patient; (b) detecting or otherwise determining the amount of pegylated enzyme in the sample using an assay method provided herein; and (c) classifying the patient as eligible to receive the one or more pegylated enzyme therapies based on the detection or amount of pegylated enzyme in the sample. In some embodiments, the patient has previously been administered a pegylated enzyme, such as a rAvPAL-PEG or variant thereof, e.g., for EST for elevated phenylalanine levels, or cancer therapy.

In other embodiments, methods provided herein may be used to observe or otherwise monitor how a patient is responding to a therapy with a pegylated enzyme. Such information can be used, for example, to make better decisions about the optimal methods, doses, or treatments for the patient. For example, these methods are applicable where a subject has been previously diagnosed as having elevated phenylalanine levels (e.g., PKU) or cancer and possibly has undergone treatment for the disease (e.g., pegylated enzyme therapy, such as rAv-PAL-PEG), and the methods provided herein are employed to monitor the progression of the disease or the treatment thereof. In addition, the information obtained by said methods may be used for selecting a patient suitable for pegylated enzyme therapy, or determining if a patient is suitable for continued pegylated enzyme therapy. In certain embodiments, the methods herein are used in conjunction with treatment of a patient with pegylated enzyme having or suspected of having elevated phenylalanine levels (e.g., a patient having one or more PAH mutations) and/or a disease associated with elevated phenylalanine levels (e.g., PKU) or cancer, or symptom thereof. That is, in certain embodiments, the assay methods provided herein are used to monitor or otherwise track pegylated enzyme levels in a patient that has been or will be administered the pegylated enzyme, such as a rAvPAL-PEG or a pegylated variant thereof.

In other embodiments, provided herein are methods of preventing, treating, or otherwise managing a disease or symptom thereof associated with elevated phenylalanine levels (e.g., PKU) or cancer in a patient, said method comprising: (a) administering a pegylated enzyme, e.g., rAvPAL-PEG or a pegylated variant thereof, to the patient; (b) obtaining a sample, such as a bodily fluid or tissue, from the patient, (c) acidifying the pegylated enzyme in the sample by adding an acidification reagent, (d) neutralizing the acidified pegylated enzyme in the sample by adding a neutralization buffer, (e) contacting the sample with an immobilized first antibody that immunospecifically binds with the pegylated enzyme; (f) optionally removing unbound sample; (g) contacting the sample bound to the immobilized first antibody with a detectable second antibody, wherein the second antibody immunospecifically binds to PEG; (h) optionally removing unbound second antibody; and (i) detecting the presence of the second antibody bound to the sample; wherein detection above background of an amount of the second antibody bound to the sample, e.g., an increase in the amount of second antibody bound to the sample as compared to a control sample having no pegylated enzyme, indicates the presence of pegylated enzyme in the sample.

In certain embodiments of any of the methods provided herein, the method further comprise providing results from the assay to personnel, e.g., at a medical facility, such as a doctor, nurse or other medical professional. In other embodiments, the method further comprises providing therapeutic options to personnel, e.g., at a medical facility, such as a doctor, nurse or other medical professional. In one embodiment, the patient has elevated phenylalanine concentrations (e.g., in blood, plasma or serum) and/or cancer. In other embodiments, the patient has a disease or disorder resulting from elevated phenylalanine levels, such as PKU, or cancer. In certain embodiments, the patient has been, is or will be treated with a pegylated enzyme, such as rAvPAL-PEG. In some embodiments, the methods provided herein are used to monitor or otherwise track pegylated enzyme, e.g., rAvPAL-PEG, therapy by detecting or otherwise measuring pegylated enzyme levels in a sample (such as blood, blood lysate, plasma, spinal fluid, cerebral fluid or bone marrow aspirate) from the patient over a period of time, such as before, during and/or after the treatment with the therapy over the course of a 1 hour, 2 hour, 3 hour, 4 hour, 6 hour, 8 hour, 10 hour, 12 hour, 18 hour, 24 hour, 2 day, 3 day, 4 day, 5 day, 6 day, 7 day, 2 week, 3 week, 4 week, 2 month, 3 month, 4 month, 5 month, 6 month, 7 month, 8 month, 9 month, 10, month 11 month, 1 year or more period of time.

In embodiments of the various methods provided herein, two or more of the steps are performed sequentially. In other embodiments of the methods provided herein, two or more of steps are performed in parallel (e.g., at the same time).

Also provided herein is a kit comprising: (a) an acidification reagent for acidifying a pegylated enzyme, (b) a neutralization buffer for neutralizing the acidified pegylated enzyme, (c) a first antibody that immunospecifically binds with the pegylated enzyme that is optionally immobilized on a solid support, and (d) a detectable second antibody that immunospecifically binds to PEG.

Any combination of the above-listed embodiments, for example, with respect to sample, pegylated enzymes, capture and detectable antibodies, patient populations, solid phase immobilization, labels and the like, are also contemplated embodiments in connection with the kits provided herein.

The kits provided herein can be used to perform methods provided herein for detecting the presence of a pegylated enzyme, e.g., rAvPAL-PEG or variant thereof, in a sample (e.g., a body fluid, such as plasma, or a tissue sample). The kits provided herein can also be used to perform the methods provided herein for classifying a patient for eligibility for a pegylated enzyme therapy (e.g., initial or continued pegylated enzyme therapy) with, e.g., a rAvPAL-PEG or variant thereof. The kits provided herein can further be used in the methods provided herein to monitor or otherwise track pegylated enzyme levels in a patient that has been or will be administered the pegylated enzyme, such as a rAvPAL-PEG or a pegylated variant thereof. The kits provided herein can also be used in the methods provided herein to prevent, treat, or otherwise manage a disease or symptom thereof associated with elevated phenylalanine levels (e.g., PKU) or cancer in a patient.

The kits can be packaged in any suitable manner, typically with the various parts, in a suitable container along with instructions for use. In certain embodiments, the kits may further comprise, where necessary, other agents for reducing the background interference in a test, control reagents, apparatus for conducting a test, and the like.

Methods and Kits to Detect Enzyme-Specific Antibodies

Most protein or enzyme therapeutics elicit some level of antibody response. In some cases this antibody response may lead to serious side effects or loss of efficacy of the therapeutic enzyme.

In a second aspect, provided herein is a method of detecting the presence of an enzyme-specific antibody (e.g., an anti-AvPAL-specific antibody or an anti-AvPAL-PEG-specific antibody), in a sample (e.g., a body fluid, such as blood, serum or plasma, or a tissue sample), said method comprising: (a) contacting the sample with an immobilized enzyme (e.g., AvPAL or rAvPAL-PEG); (b) optionally removing unbound sample; (c) contacting the sample bound to the immobilized enzyme with a detectable antibody, wherein the detectable antibody immunospecifically binds to Ig; (d) optionally removing unbound detectable antibody; and (e) detecting the presence of the detectable antibody bound to the sample; wherein detection above background of an amount of the detectable antibody bound to the sample, e.g., an increase in the amount of detectable antibody bound to the sample as compared to a control sample having no enzyme-specific antibody, indicates the presence of enzyme specific antibody in the sample.

In certain embodiments, provided is a method of detecting the presence of an enzyme-specific antibody (e.g., an anti-AvPAL-specific antibody or an anti-AvPAL-PEG-specific antibody), in a sample (e.g., a body fluid, such as blood, serum or plasma, or a tissue sample), said method comprising: (a) contacting the sample with an immobilized antibody that immunospecifically binds to an Ig (e.g., an anti-Ig, anti-IgG, anti-IgA, anti-IgM, anti-IgD or anti-IgE antibody); (b) optionally removing unbound sample; (c) contacting the sample bound to the immobilized antibody with a detectable enzyme (e.g., AvPAL or rAvPAL-PEG labeled with a detection moiety); (d) optionally removing unbound detectable enzyme; and (e) detecting the presence of the detectable enzyme bound to the sample; wherein detection above background of an amount of the detectable enzyme bound to the sample, e.g., an increase in the amount of detectable enzyme bound to the sample as compared to a control sample having no enzyme-specific antibody, indicates the presence of enzyme specific antibody in the sample.

In yet another embodiment, provided herein is a method of detecting the presence of an enzyme-specific antibody (e.g., an anti-AvPAL-specific antibody or an anti-AvPAL-PEG-specific antibody), in a sample (e.g., a body fluid, such as blood, serum or plasma, or a tissue sample), said method comprising: (a) contacting the sample with an immobilized enzyme (e.g., AvPAL or rAvPAL-PEG); (b) optionally removing unbound sample; (c) contacting the sample bound to the immobilized antibody with a detectable enzyme (e.g., AvPAL or rAvPAL-PEG labeled with a detection moiety); (d) optionally removing unbound detectable enzyme; and (e) detecting the presence of the detectable enzyme bound to the sample; wherein detection above background of an amount of the detectable enzyme bound to the sample, e.g., an increase in the amount of detectable enzyme bound to the sample as compared to a control sample having no enzyme-specific antibody, indicates the presence of enzyme specific antibody in the sample.

In certain embodiments, the sample is a body fluid (e.g., blood, serum, plasma, CSF, urine or breast milk) or a tissue sample from a patient. In some embodiments, the patient is a mammal, such as a human, monkey, dog, rabbit, rat or mouse. In an embodiment, the concentration of enzyme-specific antibody in the sample is determined.

In the methods provided herein, any isotype of enzyme-specific antibody can be detected. In certain embodiments, the anti-Ig antibody is an isotype-specific antibody, e.g., an anti-IgG, anti-IgA, anti-IgM, anti-IgD or anti-IgE antibody. In an embodiment, an enzyme-specific antibody of IgG isotype can be detected, and, in certain embodiments, the limit of detection is between 1.6 ng/mL and 8.6 ng/mL. In some embodiments, the limit of detection is less than 8.6 ng/mL or less than 4.2 ng/mL, such as between 2.1 ng/mL and 1.6 ng/mL. In other embodiments, an enzyme-specific antibody of IgM isotype can be detected, and, in certain embodiments, the limit of detection is less than 5.9 ng/mL, such as between 5.9 ng/ml and 2.8 n/ml. In an embodiment, an enzyme-specific antibody of IgE isotype can be detected. In other embodiments, an enzyme-specific antibody of IgA can be detected. In an embodiment, the sample is serum or plasma, which is equal to or less than 5% or equal to or less than 2% of the volume as described in (a).

In some embodiments, the patient has elevated phenylalanine levels. In specific embodiments, the patient has been or will be administered the enzyme, for example, for EST (e.g., for PKU) or cancer therapy.

In an embodiment, the enzyme is rAvPAL or a variant thereof. In one embodiment, the enzyme is rAvPAL_C503S, rAvPAL_C565S, rAvPAL_C565SC503S, or any combination thereof. In some embodiments, the enzyme is a pegylated enzyme. In an embodiment, the pegylated enzyme is rAvPAL-PEG. In other embodiments, the pegylated enzyme is rAvPAL-PEG_C503S, rAvPAL-PEG_C565S, rAvPAL-PEG_C565SC503S, or any combination thereof.

In specific embodiments, a method is provided to measure the amount of antibodies specific for a therapeutic enzyme (i.e., AvPAL or variant thereof) in a mammal (e.g., human) comprising: (a) binding the AvPAL to a solid support, (b) capturing AvPAL-specific antibodies in a body fluid (e.g., serum) sample from the mammal by contacting the body fluid with the AvPAL bound to the solid support, (c) contacting the captured AvPAL-specific antibodies in step (b) with an anti-Ig antibody labeled with a detectable moiety, and (d) determining the amount of the captured AvPAL-specific antibodies from the body fluid sample by detecting the presence of anti-Ig antibody labeled with the detectable moiety. In some embodiments, (c) and (d) are performed simultaneously.

In one embodiment, (a) the enzyme is bound to a solid support, (b) the enzyme-specific antibody in a body fluid sample from the mammal is captured by contacting the body fluid sample with the enzyme bound to the solid support, (c) the captured enzyme-specific antibody from (b) is contacted with an anti-Ig specific antibody (e.g., anti-IgG, anti-IgM, anti-IgA, anti-IgD or anti-IgE) labeled with a detection moiety, and (d) the amount of captured enzyme-specific antibody from the body fluid sample is determined by detecting the presence of anti-Ig specific antibody (e.g., anti-IgG, anti-IgM, anti-IgA, anti-IgD or anti-IgE) labeled with the detection moiety. In an alternative embodiment, the anti-Ig specific antibody is bound to the solid support, the enzyme-specific antibody in the body fluid sample from the mammal is captured by contacting the body fluid sample with the anti-Ig specific antibody bound to the solid support, the captured enzyme-specific antibody is contacted with the enzyme labeled with a detection moiety, and the amount of captured enzyme-specific antibody is determined by detecting the presence of enzyme labeled with the detection moiety. In another alternative embodiment, a total antibody assay is employed that takes advantage of the binary character of antibodies. In this assay, AvPAL is bound to a solid support, and the body fluid sample, which contains the enzyme-specific antibodies, is incubated with AvPAL labeled with a detection moiety. The enzyme-specific antibody in the body fluid sample is captured by contacting the body fluid sample with AvPAL bound to the solid support, and the amount of captured enzyme-specific antibody is determined by detecting the presence of AvPAL labeled with the detection moiety.

In some embodiments, a method is provided of classifying a patient for eligibility for an enzyme therapy (e.g., initial or continued enzyme therapy) with, e.g., an AvPAL or rAvPAL-PEG, or variants thereof, comprising: (a) providing a sample (e.g., a body fluid or tissue) from the patient; (b) detecting or otherwise determining the amount of enzyme-specific antibody in the sample using an assay method provided herein; and (c) classifying the patient as eligible to receive the one or more further enzyme therapies based on the detection or amount of anti-enzyme antibody in the sample. In some embodiments, the patient has previously been administered an enzyme, such as an AvPAL or rAv-PAL-PEG, or a variant thereof, e.g., for EST for elevated phenylalanine levels, or cancer therapy.

In other embodiments, methods provided herein may be used to observe or otherwise monitor how a patient is responding to a therapy with an enzyme, e.g., an AvPAL or rAv-PAL-PEG, or a variant thereof. Such information can be used, for example, to make better decisions about the optimal methods, doses, or treatments for the patient. For example, these methods are applicable where a subject has been previously diagnosed as having elevated phenylalanine levels (e.g., PKU) or cancer and possibly has undergone treatment for the disease, and the methods provided herein are employed to monitor the progression of the disease or the treatment thereof. In addition, the information obtained by said methods may be used for selecting a patient suitable for enzyme therapy, or determining if a patient is suitable for continued enzyme therapy. In certain embodiments, the methods herein are used in conjunction with treatment of a patient with enzyme having or suspected of having elevated phenylalanine levels (e.g., a patient having one or more PAH mutations) and/or a disease associated with elevated phenylalanine levels (e.g., PKU) or cancer, or symptom thereof. That is, in certain embodiments, the assay methods provided herein are used to monitor or otherwise track anti-enzyme antibody levels in a patient that has been or will be administered the enzyme, such as a AvPAL, rAvPAL-PEG, or a variant thereof.

In other embodiments, provided herein are methods of preventing, treating, or otherwise managing a disease or symptom thereof associated with elevated phenylalanine levels (e.g., PKU) or cancer in a patient, said method comprising: (a) administering an enzyme (e.g., AvPAL or rAvPAL-PEG, or a variant thereof), to the patient; (b) obtaining a sample, such as a bodily fluid or tissue, from the patient, (c) contacting the sample with an immobilized enzyme (e.g., AvPAL or rAvPAL-PEG); (d) optionally removing unbound sample; (e) contacting the sample bound to the immobilized enzyme with a detectable antibody, wherein the detectable antibody immunospecifically binds to Ig; (f) optionally removing unbound detectable antibody; and (g) detecting the presence of the detectable antibody bound to the sample; wherein detection above background of an amount of the detectable antibody bound to the sample, e.g., an increase in the amount of detectable antibody bound to the sample as compared to a control sample having no enzyme-specific antibody, indicates the presence of enzyme specific antibody in the sample.

In another embodiment, provided herein are methods of preventing, treating, or otherwise managing a disease or symptom thereof associated with elevated phenylalanine levels (e.g., PKU) or cancer in a patient, said method comprising: (a) administering an enzyme (e.g., AvPAL or rAvPAL-PEG, or a variant thereof), to the patient; (b) obtaining a sample, such as a bodily fluid or tissue, from the patient, (c) contacting the sample with an immobilized antibody that immunospecifically binds to an Ig (e.g., an anti-Ig, anti-IgG, anti-IgA, anti-IgM, anti-IgD or anti-IgE antibody); (d) optionally removing unbound sample; (e) contacting the sample bound to the immobilized antibody with a detectable enzyme (e.g., AvPAL or rAvPAL-PEG labeled with a detection moiety); (f) optionally removing unbound detectable enzyme; and (g) detecting the presence of the detectable enzyme bound to the sample; wherein detection above background of an amount of the detectable enzyme bound to the sample, e.g., an increase in the amount of detectable enzyme bound to the sample as compared to a control sample having no enzyme-specific antibody, indicates the presence of enzyme specific antibody in the sample.

In another embodiment, provided herein are methods of preventing, treating, or otherwise managing a disease or symptom thereof associated with elevated phenylalanine levels (e.g., PKU) or cancer in a patient, said method comprising: (a) administering an enzyme (e.g., AvPAL or rAvPAL-PEG, or a variant thereof), to the patient; (b) obtaining a sample, such as a bodily fluid or tissue, from the patient, (c) contacting the sample with an immobilized enzyme (e.g., AvPAL or rAvPAL-PEG); (d) optionally removing unbound sample; (e) contacting the sample bound to the immobilized antibody with a detectable enzyme (e.g., AvPAL or rAvPAL-PEG labeled with a detection moiety); (f) optionally removing unbound detectable enzyme; and (e) detecting the presence of the detectable enzyme bound to the sample; wherein detection above background of an amount of the detectable enzyme bound to the sample, e.g., an increase in the amount of detectable enzyme bound to the sample as compared to a control sample having no enzyme-specific antibody, indicates the presence of enzyme specific antibody in the sample.

In certain embodiments of any of the methods provided herein, the method further comprise providing results from the assay to personnel, e.g., at a medical facility, such as a doctor, nurse or other medical professional. In other embodiments, the method further comprises providing therapeutic options to personnel, e.g., at a medical facility, such as a doctor, nurse or other medical professional. In one embodiment, the patient has elevated phenylalanine concentrations (e.g., in blood, plasma or serum) and/or cancer. In other embodiments, the patient has a disease or disorder resulting from elevated phenylalanine levels, such as PKU, or cancer. In certain embodiments, the patient has been, is or will be treated with an enzyme, such as AvPAL or rAvPAL-PEG, or any variant thereof. In some embodiments, the methods provided herein are used to monitor or otherwise track enzyme-specific antibodies during the course of enzyme (e.g., AvPAL, AvPAL-PEG, or any variant thereof) therapy by detecting or otherwise measuring enzyme-specific antibody levels in a sample (such as blood, blood lysate, plasma, spinal fluid, cerebral fluid or bone marrow aspirate) from the patient over a period of time, such as before, during and/or after the treatment with the therapy over the course of a 1 hour, 2 hour, 3 hour, 4 hour, 6 hour, 8 hour, 10 hour, 12 hour, 18 hour, 24 hour, 2 day, 3 day, 4 day, 5 day, 6 day, 7 day, 2 week, 3 week, 4 week, 2 month, 3 month, 4 month, 5 month, 6 month, 7 month, 8 month, 9 month, 10, month 11 month, 1 year or more period of time.

In embodiments of the various methods provided herein, two or more of the steps are performed sequentially. In other embodiments of the methods provided herein, two or more of steps are performed in parallel (e.g., at the same time).

Also provided herein is a kit comprising: (a) an enzyme (e.g., AvPAL or rAvPAL-PEG), which is optionally immobilized on a solid support, and (b) a detectable antibody, wherein the detectable antibody immunospecifically binds to Ig. In certain embodiments, the kit further comprises one or more components in one or more containers and/or instructions for use.

Also provided herein is a kit comprising: (a) an antibody that immunospecifically binds to an Ig (e.g., an anti-Ig, anti-IgG, anti-IgA, anti-IgM, anti-IgD or anti-IgE antibody), wherein the anti-Ig antibody is optionally immobilized to a solid support; and (b) a detectable enzyme (e.g., AvPAL or rAvPAL-PEG labeled with a detection moiety). In certain embodiments, the kit further comprises one or more components of the kit in one or more containers and/or instructions for use.

Further provided herein is a kit comprising: (a) an enzyme (e.g., AvPAL or rAvPAL-PEG), which is optionally immobilized on a solid support; and (b) a detectable enzyme (e.g., AvPAL or rAvPAL-PEG labeled with a detection moiety). In certain embodiments, the kit further comprises one or more components of the kit in one or more containers and/or instructions for use.

Any combination of the above-listed embodiments, for example, with respect to sample, enzymes, enzyme-specific antibodies, detectable enzymes, detectable enzymes, detectable antibodies, patient populations, solid phase immobilization, labels and the like, are also contemplated embodiments in connection with the kits provided herein.

The kits provided herein can be used to perform methods provided herein for detecting the presence of an enzyme-specific antibody (e.g., an anti-AvPAL-specific antibody or an anti-AvPAL-PEG-specific antibody), in a sample (e.g., a body fluid, such as blood, serum or plasma, or a tissue sample). The kits provided herein can also be used to perform the methods provided herein for classifying a patient for eligibility for an enzyme therapy (e.g., initial or continued enzyme therapy) with, e.g., an AvPAL or rAvPAL-PEG, or variants thereof. The kits provided herein can further be used in the methods provided herein to monitor or otherwise track anti-enzyme antibody levels in a patient that has been or will be administered the enzyme, such as a AvPAL, rAvPAL-PEG, or a variant thereof. The kits provided herein can also be used in the methods provided herein to prevent, treat, or otherwise manage a disease or symptom thereof associated with elevated phenylalanine levels (e.g., PKU) or cancer in a patient.

The kits can be packaged in any suitable manner, typically with the various parts, in a suitable container along with instructions for use. In certain embodiments, the kits may further comprise, where necessary, other agents for reducing the background interference in a test, control reagents, apparatus for conducting a test, and the like.

Methods and Kits to Detect Neutralizing Enzyme-Specific Antibodies

Most protein or enzyme therapeutics elicit some level of antibody response. In some cases this antibody response may lead to serious side effects or loss of efficacy.

In a third aspect, provided herein is a method for detecting the presence of neutralizing enzyme-specific antibodies (e.g., a neutralizing antibody that immunospecifically binds to an enzyme, such as AvPAL, rAvPAL-PEG and/or any derivative thereof) in a sample (e.g., a body fluid, such as plasma, or a tissue sample), said method comprising: (a) contacting the sample with the enzyme (e.g., AvPAL, rAvPAL-PEG, and/or any variant thereof), which is optionally immobilized on a solid support; (b) optionally removing unbound sample; (c) adding a substrate for the enzyme; (d) optionally removing unbound substrate; and (e) detecting the presence of enzymatic activity between the enzyme and substrate; wherein a reduction of enzymatic activity, e.g., as compared to a sample having no neutralizing anti-enzyme antibodies, indicates the presence of neutralizing enzyme-specific antibodies in the sample.

In certain embodiments, the neutralizing antibodies that immunospecifically bind to an enzyme, such as AvPAL, rAvPAL-PEG, or any derivative thereof, are contacted with a pegylated form of the enzyme, such as rAvPAL-PEG or variant thereof, wherein the antibodies neutralize the pegylated enzyme activity by interacting with either the enzyme (e.g., AvPAL or derivative thereof) and/or the PEG moiety. In other embodiments, the neutralizing antibodies that immunospecifically bind to an enzyme, such as AvPAL, rAvPAL-PEG, or any derivative thereof, are contacted with an enzyme that is not pegylated, such as AvPAL or variant thereof, wherein the antibodies neutralize the enzyme activity by interacting with the enzyme (e.g., AvPAL or derivative thereof).

In certain embodiments, the sample is a body fluid (e.g., blood, serum, plasma, CSF, urine or breast milk) or a tissue sample from a patient. In some embodiments, the patient is a mammal, such as a human, monkey, dog, rabbit, rat or mouse. In an embodiment, the concentration of enzyme-specific antibody in the sample is determined.

In an embodiment, the concentration of neutralizing enzyme-specific antibody in the sample is determined. In certain embodiments, the limit of detection is less than or equal to 10 µg/mL. In an embodiment, the sample is serum or plasma, which is equal to or less than 5% or equal to or less than 2% of the volume as described in (a). In one embodiment, the neutralizing enzyme-specific antibodies in a sample are detected in an assay using 96-well plates. In other embodiments, the neutralizing enzyme-specific antibodies in a sample are detected in an assay using cuvettes.

In some embodiments, the patient has elevated phenylalanine levels. In specific embodiments, the patient has been or will be administered the enzyme, for example, for EST (e.g., for PKU) or cancer therapy.

In an embodiment, the enzyme is rAvPAL or a variant thereof. In one embodiment, the enzyme is rAvPAL_C503S, rAvPAL_C565S, rAvPAL_C565SC503S, or any combination thereof. In some embodiments, the enzyme is a pegylated enzyme. In an embodiment, the pegylated enzyme is rAvPAL-PEG. In other embodiments, the pegylated enzyme is rAvPAL-PEG_C503S, rAvPAL-PEG_C565S, rAvPAL-PEG_C565SC503S, or any combination thereof.

In a specific embodiment, provided is a method to measure the amount of neutralizing antibodies specific for a therapeutic enzyme (i.e., AvPAL or variant thereof) in a mammal (e.g., human) comprising: (a) contacting AvPAL-specific antibodies in a body fluid (e.g., serum) sample from the mammal with an AvPAL or variant thereof, (b) adding a substrate for the AvPAL or variant thereof to the mixture of AvPAL-specific antibodies and AvPAL or variant thereof in (a), and (c) determining the amount of the neutralizing AvPAL-specific antibodies from the body fluid by detecting the reduction of the enzymatic reactivity of AvPAL or variant thereof with the substrate in (b). In one embodiment, the method comprises (a) contacting AvPAL-specific antibodies in a body fluid (e.g., serum) sample from the mammal with an AvPAL or variant thereof, (b) adding a substrate for the AvPAL or variant thereof to the mixture of AvPAL-specific antibodies and AvPAL or variant thereof in (a), and (c) determining the amount of the neutralizing AvPAL-specific antibodies from the body fluid by detecting the reduction of the enzymatic reactivity of AvPAL or variant thereof with the substrate in (b). In one embodiment, the neutralizing AvPAL-specific antibodies in a body fluid sample are detected in an assay using 96-well plates. In an alternative embodiment, the neutralizing AvPAL-specific antibodies in a body fluid sample are detected in an assay similar to that described above, except that the assays are performed in cuvettes. This assay can be low throughput and require a higher volume of material, but can be suitable for performing enzyme activity assays, e.g., for product release. In yet another alternative embodiment, the neutralizing AvPAL-specific antibodies in a body fluid sample are detected in an assay similar to that described above, except that in (a) the AvPAL-specific antibodies in a body fluid (e.g., serum) sample from the mammal are contacted with rAvPAL-PEG or variant thereof. This assay can detect antibodies that neutralize rAvPAL-PEG enzyme activity by interacting with the AvPAL or PEG moiety.

In some embodiments, a method is provided of classifying a patient for eligibility for an enzyme therapy (e.g., initial or continued enzyme therapy) with, e.g., a AvPAL or rAvPAL-PEG, or variants thereof, comprising: (a) providing a sample (e.g., a body fluid or tissue) from the patient; (b) detecting or otherwise determining the amount of neutralizing enzyme-specific antibody in the sample using an assay method provided herein; and (c) classifying the patient as eligible to receive the one or more further enzyme therapies based on the detection or amount of neutralizing enzyme-specific antibody in the sample. In some embodiments, the patient has previously been administered an enzyme, such as an AvPAL or rAvPAL-PEG, or a variant thereof, e.g., for EST for elevated phenylalanine levels or cancer therapy.

In other embodiments, methods provided herein may be used to observe or otherwise monitor how a patient is responding to a therapy with an enzyme, e.g., an AvPAL or rAvPAL-PEG, or a variant thereof. Such information can be used, for example, to make better decisions about the optimal methods, doses, or treatments for the patient. For example, these methods are applicable where a subject has been previously diagnosed as having elevated phenylalanine levels (e.g., PKU) or cancer and possibly has undergone treatment for the disease, and the methods provided herein are employed to monitor the progression of the disease or the treatment thereof. In addition, the information obtained by said methods may be used for selecting a patient suitable for enzyme therapy, or determining if a patient is suitable for continued enzyme therapy. In certain embodiments, the methods herein are used in conjunction with treatment of a patient with enzyme having or suspected of having elevated phenylalanine levels (e.g., a patient having one or more PAH mutations) and/or a disease associated with elevated phenylalanine levels (e.g., PKU) or cancer, or symptom thereof. That is, in certain embodiments, the assay methods provided herein are used to monitor or otherwise track neutralizing anti-enzyme antibody levels in a patient that has been or will be administered the enzyme, such as an AvPAL, rAvPAL-PEG, or a variant thereof.

In other embodiments, provided herein are methods of preventing, treating, or otherwise managing a disease or symptom thereof associated with elevated phenylalanine levels (e.g., PKU) or cancer in a patient, said method comprising: (a) administering an enzyme (e.g., AvPAL or rAvPAL-PEG, or a variant thereof), to the patient; (b) obtaining a sample, such as a bodily fluid or tissue, from the patient, (c) contacting the sample with the enzyme (e.g., AvPAL, rAvPAL-PEG, and/or any variant thereof), which is optionally immobilized on a solid support; (d) optionally removing unbound sample; (e) adding a substrate for the enzyme; (f) optionally removing unbound substrate; and (g) detecting the presence of enzymatic activity between the enzyme and substrate; wherein a reduction of enzymatic activity, e.g., as compared to a sample having no neutralizing anti-enzyme antibodies, indicates the presence of neutralizing enzyme-specific antibodies in the sample.

In certain embodiments of any of the methods provided herein, the method further comprise providing results from the assay to personnel, e.g., at a medical facility, such as a doctor, nurse or other medical professional. In other embodiments, the method further comprises providing therapeutic options to personnel, e.g., at a medical facility, such as a doctor, nurse or other medical professional. In one embodiment, the patient has elevated phenylalanine concentrations (e.g., in blood, plasma or serum) and/or cancer. In other embodiments, the patient has a disease or disorder resulting from elevated phenylalanine levels, such as PKU, or cancer. In certain embodiments, the patient has been, is or will be treated with an enzyme, such as AvPAL, rAvPAL-PEG, or any variant thereof. In some embodiments, the methods provided herein are used to monitor or otherwise track neutralizing enzyme-specific antibodies during the course of enzyme (e.g., AvPAL, rAvPAL-PEG, or any variant thereof) therapy by detecting or otherwise measuring neutralizing enzyme-specific antibody levels in a sample (such as blood, blood lysate, plasma, spinal fluid, cerebral fluid or bone marrow aspirate) from the patient over a period of time, such as before, during and/or after the treatment with the therapy over the course of a 1 hour, 2 hour, 3 hour, 4 hour, 6 hour, 8 hour, 10 hour, 12 hour, 18 hour, 24 hour, 2 day, 3 day, 4 day, 5 day, 6 day, 7 day, 2 week, 3 week, 4 week, 2 month, 3 month, 4 month, 5 month, 6 month, 7 month, 8 month, 9 month, 10, month 11 month, 1 year or more period of time.

In embodiments of the various methods provided herein, two or more of the steps are performed sequentially. In other embodiments of the methods provided herein, two or more of steps are performed in parallel (e.g., at the same time).

Also provided herein is a kit comprising: (a) an enzyme (e.g., AvPAL, rAvPAL-PEG, and/or any variant thereof), which is optionally immobilized on a solid support; and (b) a substrate for the enzyme. In certain embodiments, the kit further comprises one or more components of the kit in one or more containers and/or instructions for use.

Any combination of the above-listed embodiments, for example, with respect to sample, enzymes, neutralizing enzyme-specific antibodies, enzymes, substrates and the like, are also contemplated embodiments in connection with the kits provided herein.

The kits provided herein can be used to perform methods provided herein for detecting the presence of neutralizing enzyme-specific antibodies (e.g., a neutralizing antibody that immunospecifically binds to an enzyme, such as AvPAL, rAvPAL-PEG and/or any derivative thereof) in a sample (e.g., a body fluid, such as plasma, or a tissue sample). The kits provided herein can also be used to perform the methods provided herein for classifying a patient for eligibility for an enzyme therapy (e.g., initial or continued enzyme therapy) with, e.g., an AvPAL or rAvPAL-PEG, or variants thereof. The kits provided herein can further be used in the methods provided herein to monitor or otherwise track neutralizing anti-enzyme antibody levels in a patient that has been or will be administered the enzyme, such as an AvPAL, rAvPAL-PEG, or a variant thereof. The kits provided herein can also be used in the methods provided herein to prevent, treat, or otherwise manage a disease or symptom thereof associated with elevated phenylalanine levels (e.g., PKU) or cancer in a patient.

The kits can be packaged in any suitable manner, typically with the various parts, in a suitable container along with instructions for use. In certain embodiments, the kits may further comprise, where necessary, other agents for reducing the background interference in a test, control reagents, apparatus for conducting a test, and the like.

Methods and Kits to Detect PEG-Specific Antibodies

PEG and derivatives thereof are typically considered non-immunogenic due to their chemical structures and are used in pharmaceutical and cosmetic products. However, protein or enzyme therapeutics that are conjugated to PEG or a derivative thereof can still elicit some level of antibody response to the PEG or derivative thereof. In some cases the antibody response to PEG or derivative thereof can lead to serious side effects or loss of efficacy.

In a fourth aspect, provided herein is a method for detecting the presence of PEG-specific antibodies (e.g., an antibody that immunospecifically binds, e.g., a PEG moiety of rAvPAL-PEG or a variant thereof) in a sample (e.g., a body fluid, such as plasma, or a tissue sample), said method comprising: (a) contacting the sample with immobilized PEG; (b) optionally removing unbound sample; (c) contacting the sample bound to the immobilized PEG with a detectable antibody, wherein the detectable antibody immunospecifically binds to Ig; (d) optionally removing unbound detectable antibody; and (e) detecting the presence of the detectable antibody bound to the sample; wherein detection above background of an amount of the detectable antibody bound to the sample, e.g., an increase in the amount of detectable antibody bound to the sample as compared to a control sample having no enzyme-specific antibody, indicates the presence of PEG-specific antibody in the sample.

In another embodiment, provided herein is a method for detecting the presence of PEG-specific antibodies (e.g., an antibody that immunospecifically binds, e.g., a PEG moiety of rAvPAL-PEG or a variant thereof) in a sample (e.g., a body fluid, such as plasma, or a tissue sample), said method comprising: (a) contacting the sample with immobilized antibody that immunospecifically binds to an Ig; (b) optionally removing unbound sample; (c) contacting the sample bound to the immobilized anti-Ig antibody with a detectable PEG (e.g., a PEG labeled with a detection moiety); (d) optionally removing unbound detectable PEG; and (e) detecting the presence of the detectable PEG bound to the sample; wherein detection above background of an amount of the detectable PEG bound to the sample, e.g., an increase in the amount of detectable PEG bound to the sample as compared to a control sample having no PEG-specific antibody, indicates the presence of PEG-specific antibody in the sample.

In yet another embodiment, provided herein is a method for detecting the presence of PEG-specific antibodies (e.g., an antibody that immunospecifically binds, e.g., a PEG moiety of rAvPAL-PEG or a variant thereof) in a sample (e.g., a body fluid, such as plasma, or a tissue sample), said method comprising: (a) contacting the sample with immobilized PEG; (b) optionally removing unbound sample; (c) contacting the sample bound to the immobilized PEG with a detectable PEG (e.g., a PEG labeled with a detection moiety); (d) optionally removing unbound detectable PEG; and (e) detecting the presence of the detectable PEG bound to the sample; wherein detection above background of an amount of the detectable PEG bound to the sample, e.g., an increase in the amount of detectable PEG bound to the sample as compared to a control sample having no PEG-specific antibody, indicates the presence of PEG-specific antibody in the sample.

In certain embodiments, the sample is a body fluid (e.g., blood, serum, plasma, CSF, urine or breast milk) or a tissue sample from a patient. In some embodiments, the patient is a mammal, such as a human, monkey, dog, rabbit, rat or mouse. In an embodiment, the concentration of PEG-specific antibody in the sample is determined.

In the methods provided herein, any isotype of PEG-specific antibody can be detected. In certain embodiments, the anti-Ig antibody is an isotype-specific antibody, e.g., an anti-IgG, anti-IgA, anti-IgM, anti-IgD or anti-IgE antibody. In an embodiment, the sample is serum or plasma, which is equal to or less than 5% or equal to or less than 2% of the volume as described in (a).

In some embodiments, the PEG is methoxy PEG, such as a 20 kDa methoxy PEG. In one embodiment, the methoxy PEG is inactivated. In an embodiment, the PEG is hydroxy PEG, such as a 6 kDa hydroxy PEG. The PEG may or may not be inactivated.

In some embodiments, the patient has elevated phenylalanine levels. In specific embodiments, the patient has been or will be administered the enzyme, for example, for EST (e.g., for PKU) or cancer therapy.

In an embodiment, the enzyme is rAvPAL or a variant thereof. In one embodiment, the enzyme is rAvPAL_C503S, rAvPAL_C565S, rAvPAL_C565SC503S, or any combination thereof. In some embodiments, the enzyme is a pegylated enzyme. In an embodiment, the pegylated enzyme is rAvPAL-PEG. In other embodiments, the pegylated enzyme is rAvPAL-PEG_C503S, rAvPAL-PEG_C565S, rAvPAL-PEG_C565SC503S, or any combination thereof.

In a specific embodiment, provided is a method to measure the amount of antibodies specific for PEG or derivative thereof in a mammal (e.g., human) comprising: (a) binding the PEG (e.g., inactivated methoxy PEG) to a solid support, (b) capturing PEG-specific antibodies in a body fluid (e.g., serum) sample from the mammal by contacting the body fluid with the PEG bound to the solid support, (c) contacting the captured PEG-specific antibodies in (b) with an anti-Ig antibody labeled with a detectable moiety, and (d) determining the amount of the captured PEG-specific antibodies from the body fluid sample by detecting the presence of anti-Ig antibody labeled with the detectable moiety. In some embodiments, (c) and (d) are performed simultaneously. In one embodiment, (a) the PEG is bound to a solid support, (b) the PEG-specific antibody in a body fluid sample from the mammal is captured by contacting the body fluid sample with the PEG bound to the solid support, (c) the captured PEG-specific antibody from (b) is contacted with an anti-Ig specific antibody (e.g., anti-IgG, anti-IgM, anti-IgA, anti-IgD or anti-IgE) labeled with a detection moiety, and (d) the amount of captured PEG-specific antibody from the body fluid sample is determined by detecting the presence of anti-Ig specific antibody (e.g., anti-IgG, anti-IgM, anti-IgA, anti-IgD or anti-IgE) labeled with the detection moiety. In an alternative embodiment, the anti-Ig specific antibody is bound to the solid support, the PEG-specific antibody in the body fluid sample from the mammal is captured by contacting the body fluid sample with the anti-Ig specific antibody bound to the solid support, the captured PEG-specific antibody is contacted with the PEG labeled with a detection moiety, and the amount of captured PEG-specific antibody is determined by detecting the presence of PEG labeled with the detection moiety. In another alternative embodiment, a total antibody assay is employed that takes advantage of the binary character of antibodies. In this assay, PEG is bound to a solid support, and the body fluid sample, which contains the PEG-specific antibodies, is incubated with PEG labeled with a detection moiety. The PEG-specific antibody in the body fluid sample is captured by contacting the body fluid sample with PEG bound to the solid support, and the amount of captured PEG-specific antibody is determined by detecting the presence of PEG labeled with the detection moiety.

In some embodiments, a method is provided of classifying a patient for eligibility for a pegylated enzyme therapy (e.g., initial or continued pegylated enzyme therapy) with, e.g., a rAvPAL-PEG or variant thereof, comprising: (a) providing a sample (e.g., a body fluid or tissue) from the patient; (b) detecting or otherwise determining the amount of PEG-specific antibody in the sample using an assay method provided herein; and (c) classifying the patient as eligible to receive the one or more further pegylated enzyme therapies based on the detection or amount of anti-pegylated enzyme antibody in the sample. In some embodiments, the patient has previously been administered a pegylated enzyme, such as a rAvPAL-PEG or variant thereof, e.g., for EST for elevated phenylalanine levels or cancer therapy.

In other embodiments, methods provided herein may be used to observe or otherwise monitor how a patient is responding to a therapy with a pegylated enzyme, e.g., a rAvPAL-PEG or a variant thereof. Such information can be used, for example, to make better decisions about the optimal methods, doses, or treatments for the patient. For example, these methods are applicable where a subject has been previously diagnosed as having elevated phenylalanine levels (e.g., PKU) or cancer and possibly has undergone treatment for the disease, and the methods provided herein are employed to monitor the progression of the disease or the treatment thereof. In addition, the information obtained by said methods may be used for selecting a patient suitable for pegylated enzyme therapy, or determining if a patient is suitable for continued pegylated enzyme therapy. In certain embodiments, the methods herein are used in conjunction with treatment of a patient with enzyme having or suspected of having elevated phenylalanine levels (e.g., a patient having one or more PAH mutations) and/or a disease associated with elevated phenylalanine levels (e.g., PKU) or cancer, or symptom thereof. That is, in certain embodiments, the assay methods provided herein are used to monitor or otherwise track anti-PEG antibody levels in a patient that has been or will be administered a pegylated enzyme, such as a rAvPAL-PEG or variant thereof.

In other embodiments, provided herein are methods of preventing, treating, or otherwise managing a disease or symptom thereof associated with elevated phenylalanine levels (e.g., PKU) or cancer in a patient, said method comprising: (a) administering a pegylated enzyme (e.g., rAvPAL-PEG or variant thereof), to the patient; (b) obtaining a sample, such as a bodily fluid or tissue, from the patient, (c) contacting the sample with immobilized PEG; (d) optionally removing unbound sample; (e) contacting the sample bound to the immobilized PEG with a detectable antibody, wherein the detectable antibody immunospecifically binds to Ig; (f) optionally removing unbound detectable antibody; and (g) detecting the presence of the detectable antibody bound to the sample; wherein detection above background of an amount of the detectable antibody bound to the sample, e.g., an increase in the amount of detectable antibody bound to the sample as compared to a control sample having no enzyme-specific antibody, indicates the presence of PEG-specific antibody in the sample.

In another embodiment, provided herein are methods of preventing, treating, or otherwise managing a disease or symptom thereof associated with elevated phenylalanine levels (e.g., PKU) or cancer in a patient, said method comprising: (a) administering an enzyme (e.g., AvPAL or rAvPAL-PEG, or a variant thereof), to the patient; (b) obtaining a sample, such as a bodily fluid or tissue, from the patient, (c) contacting the sample with immobilized antibody that immunospecifically binds to an Ig; (d) optionally removing unbound sample; (e) contacting the sample bound to the immobilized anti-Ig antibody with a detectable PEG (e.g., a PEG labeled with a detection moiety); (f) optionally removing unbound detectable PEG; and (g) detecting the presence of the detectable PEG bound to the sample; wherein detection above background of an amount of the detectable PEG bound to the sample, e.g., an increase in the amount of detectable PEG bound to the sample as compared to a control sample having no PEG-specific antibody, indicates the presence of PEG-specific antibody in the sample.

In another embodiment, provided herein are methods of preventing, treating, or otherwise managing a disease or symptom thereof associated with elevated phenylalanine levels (e.g., PKU) or cancer in a patient, said method comprising: (a) administering an enzyme (e.g., AvPAL or rAvPAL-PEG, or a variant thereof), to the patient; (b) obtaining a sample, such as a bodily fluid or tissue, from the patient, (c) contacting the sample with immobilized PEG; (d) optionally removing unbound sample; (e) contacting the sample bound to the immobilized PEG with a detectable PEG (e.g., a PEG labeled with a detection moiety); (f) optionally removing unbound detectable PEG; and (g) detecting the presence of the detectable PEG bound to the sample; wherein detection above background of an amount of the detectable PEG bound to the sample, e.g., an increase in the amount of detectable PEG bound to the sample as compared to a control sample having no PEG-specific antibody, indicates the presence of PEG-specific antibody in the sample.

In certain embodiments of any of the methods provided herein, the method further comprise providing results from the assay to personnel, e.g., at a medical facility, such as a doctor, nurse or other medical professional. In other embodiments, the method further comprises providing therapeutic options to personnel, e.g., at a medical facility, such as a doctor, nurse or other medical professional. In one embodiment, the patient has elevated phenylalanine concentrations (e.g., in blood, plasma or serum) and/or cancer. In other embodiments, the patient has a disease or disorder resulting from elevated phenylalanine levels, such as PKU, or cancer. In certain embodiments, the patient has been, is or will be treated with a pegylated enzyme, such as rAvPAL-PEG or a variant thereof. In some embodiments, the methods provided herein are used to monitor or otherwise track PEG-specific antibodies during the course of enzyme (e.g., rAvPAL-PEG or a variant thereof) therapy by detecting or otherwise measuring PEG-specific antibody levels in a sample (such as blood, blood lysate, plasma, spinal fluid, cerebral fluid or bone marrow aspirate) from the patient over a period of time, such as before, during and/or after the treatment with the therapy over the course of a 1 hour, 2 hour, 3 hour, 4 hour, 6 hour, 8 hour, 10 hour, 12 hour, 18 hour, 24 hour, 2 day, 3 day, 4 day, 5 day, 6 day, 7 day, 2 week, 3 week, 4 week, 2 month, 3 month, 4 month, 5 month, 6 month, 7 month, 8 month, 9 month, 10, month 11 month, 1 year or more period of time.

In embodiments of the various methods provided herein, two or more of the steps are performed sequentially. In other embodiments of the methods provided herein, two or more of steps are performed in parallel (e.g., at the same time).

Also provided herein is a kit comprising: (a) a PEG, which is optionally immobilized on a solid support; and (b) a detectable antibody immunospecifically binds to Ig. In certain embodiments, the kit further comprises one or more components of the kit in one or more containers and/or instructions for use.

Also provided herein is a kit comprising: (a) an antibody that immunospecifically binds to an Ig, which is optionally immobilized on a solid support; and (b) a detectable PEG (e.g., a PEG labeled with a detection moiety). In certain embodiments, the kit further comprises one or more components of the kit in one or more containers and/or instructions for use.

Further provided herein is a kit comprising: (a) a PEG, which is optionally immobilized on a solid support; and (b) a detectable PEG (e.g., a PEG labeled with a detection moiety). In certain embodiments, the kit further comprises one or more components of the kit in one or more containers and/or instructions for use.

Any combination of the above-listed embodiments, for example, with respect to sample, pegylated enzymes, PEG-specific antibodies, anti-Ig antibodies, PEGs, detectable PEGs, detectable antibodies, patient populations, solid phase immobilization, labels and the like, are also contemplated embodiments in connection with the kits provided herein.

The kits provided herein can be used to perform methods provided herein for detecting the presence of PEG-specific antibodies (e.g., an antibody that immunospecifically binds, e.g., a PEG moiety of rAvPAL-PEG or a variant thereof) in a sample (e.g., a body fluid, such as plasma, or a tissue sample). The kits provided herein can also be used to perform the methods provided herein for classifying a patient for eligibility for a pegylated enzyme therapy (e.g., initial or continued pegylated enzyme therapy) with, e.g., a rAvPAL-PEG or variant thereof. The kits provided herein can further be used in the methods provided herein to monitor or otherwise track anti-PEG antibody levels in a patient that has been or will be administered a pegylated enzyme, such as an AvPAL-PEG or variant thereof. The kits provided herein can also be used in the methods provided herein to prevent, treat, or otherwise manage a disease or symptom thereof associated with elevated phenylalanine levels (e.g., PKU) or cancer in a patient.

The kits can be packaged in any suitable manner, typically with the various parts, in a suitable container along with instructions for use. In certain embodiments, the kits may further comprise, where necessary, other agents for reducing the background interference in a test, control reagents, apparatus for conducting a test, and the like.

The following examples are offered by way of illustration, and not by way of limitation.

EXAMPLES

Example 1

Cloning of *Nostoc punctiforme* and *Anabaena variabilis* PAL DNA Manipulations

*N. punctiforme* genomic DNA was purchased from ATCC (29133D) and the PAL gene (ZP_00105927) was PCR-amplified from primers 5'-CACTGTCATAT-GAATATAACATCTCTACAACAGAACAT-3' (SEQ ID NO:12) and 5'-GACAGTGGCGGCCGCTCACGTT-GACTTTAAGCTCGAAAAAATATG-3' (SEQ ID NO:13). The resulting PCR product was digested with NdeI and NotI and the 1.7 kb fragment was ligated into pET-28a(+) and pET-30a(+) (Novagen) for N-His tagged and untagged, respectively.

*A. variabilis* cells were purchased from ATCC (29413). Genomic DNA was extracted (Qiagen) and the PAL gene (YP_324488) was amplified by SOE-PCR to remove an NheI site. Primer 1 (5'-CACTGTGCTAGCATGAAGA-CACTATCTCAAGCACAAAG-3') (SEQ ID NO:14) and primer 2 (5'-GGAAATTTCCTCCATGATAGCTGGCTTG-GTTATCAACATCAATTAGTGG-3') (SEQ ID NO:15) were used to amplify nucleotides 1-1190 and primer 3 (5'-CCACTAATTGATGTTGATAACCAAGCCAGCTAT-CATGGAGGAAATTTCC-3') (SEQ ID NO:16) and primer 4 (5'-CACTGTGCGGCCGCTTAATGCAAGCAGGG-TAAGATATCTTG-3') (SEQ ID NO:17) were used to amplify nucleotides 1142-1771. These two PCR products were combined to amplify the full-length gene with primers 1 and 4. The resulting PCR product was digested with NheI, blunted with Klenow (NEB), then digested with NotI. The 1.7 kb fragment was ligated into pET-28a(+) and pET-30a(+) (Novagen). This plasmid was named 3p 86-23. The *A. variabilis* PAL (AvPAL) gene was also cloned into the vector pIBX7 (Tkalec, et al., Appl. Environ. Microbiol. 66:29-35 (2000)), which was derived from pIBX1 (Su, et al., Appl. Environ. Microbiol. 62:2723-2734 (1996)) (see Example 5).

Bacterial Strains and Culture Conditions

For *N. punctiforme* PAL (NpPAL), *E. coli* BL21(DE3) cells (Stratagene) were transformed with pGro7 (TaKaRa) and competent BL21(DE3)pGro7 cells were prepared by the Inoue Method (Sambrook and Russell, Molecular Cloning: A Laboratory Manual, $3^{rd}$ Edition (Cold Spring Harbor Laboratory Press, Cold Spring Harbor, 2001)). These cells were transformed with pET-28-NpPAL and cultured in 25 mL LB with 50 mg/L kanamycin and 20 mg/L chloramphenicol overnight at 37° C. Twenty milliliters of this culture was seeded into 1 L of LB medium with kanamycin, chloramphenicol, and 500 mg/L L-arabinose and grown at 37° C. At an $OD_{600}$ of 0.6, the culture was chilled on ice. After 5 minutes, the culture was induced with 0.3 mM IPTG and grown for 16 hours at 20° C. Cells were harvested by centrifugation.

BL21(DE3)pLysS cells (Stratagene) were transformed with AvPAL and cultured identically to NpPAL without the arabinose induction.

AvPAL cloned in the pIBX7 vector (see Example 7) was introduced by transformation into BLR(DE3)/pLysS (Novagen) cells and cultured in 25 mL LB with 50 mg/L kanamycin overnight at 37° C. Twenty milliliters of this culture was seeded into 1 L of LB medium with kanamycin, and grown at 37° C. At an $OD_{600}$ of 0.6, the culture was chilled on ice. After 5 minutes, the culture was induced with 0.3 mM IPTG and grown for 16 hours at 30° C. Cells were harvested by centrifugation.

Example 2

Purification of NpPAL and AvPAL

The cultures were centrifuged in a bench-top centrifuge at 5,000 g for 20 minutes and the supernatant discarded. The cell pellets were typically frozen at −70° C. prior to further processing. Upon thawing, the cell pellets were suspended to approximately 80 optical density units (600 nm) in TBS (25 mM Tris, 150 mM NaCl, pH 7.8). The cells were lysed by two passes through an APV pressure homogenizer at 12-14, 000 psi. The crude lysate was then heat-treated at 55° C. for 2 hours. The lysate is centrifuged at 10,000 g for 30 minutes and the supernatant retained and filtered with a 0.2 μm vacuum filter (Corning).

The PAL was purified from the clarified lysate by passage sequentially over a butyl 650M column (Tosoh BioSciences) and a MacroPrep High Q column (BioRad). The eluted product showed a high level of purity by both SDS PAGE and reverse phase HPLC.

Example 3

Generation of Pegylated PAL Variants

A method for pegylation of PAL from *Rhodosporidium toruloides* (RtPAL) is described below. Similar methods are used for pegylation of prokaryotic PAL (e.g., *Nostoc punctiforme* (NpPAL) or *Anabaena variabilis* (AvPAL)) are described in Example 4.

Protein Pegylation

Pegylation uses modifications of literature methods (Hershfield, et al., (1991), ibid.; U.S. Pat. No. 6,057,292; Lu, et al., Biochemistry 40(44):13288-13301 (2001); Nektar Therapeutics, 2003 catalog). Activated PEGs include both the linear PEG succinimidyl succinates (mPEG-SPA, MW 5 kDa or MW 20 kDa) and the branched PEG hydrosuccinimides (mPEG$_2$-NHS ester, MW 10 kDa or MW 40 kDa), which are both capped on one end with a methoxy group and available from Nektar Therapeutics; experimental determination of optimal pegylated proteins is normally required (Veronese, et al., J. Bioactive Compatible Polymers 12:196-207 (1997)). Optimal pegylation conditions are determined using different ratios of PAL:PEG (taking into account the molar ratio of protein along with the number of lysines per protein monomer), different pHs, different buffers, various temperatures and incubation times. High PAL protein:PEG derivatization ratios are necessary since native PAL has a large number of lysines (e.g., 29 per *Rhodosporidium toruloides* (Rt) monomer, 18 per *Anabaena viriabilis* (Av) monomer and 18 per *Nostoc punctiforme* (Np) monomer) and because un-modified PAL displays immunoreactivity upon repeated injection in mice and since naked (wild-type) PAL is quickly inactivated upon exposure to proteases. Pegylation reactions are stopped by freezing at −20° C., and the samples will be analyzed by SDS-PAGE, MALDI-TOF mass spectroscopy, activity assessment, proteolytic sensitivity, and immunoreactivity.

Prior to activity, proteolysis, and immune assessment, and in order to remove excess unreacted PEG, reactions are dialyzed against pH 8.5, 0.05 M potassium phosphate buffer overnight at 4° C. with stirring using Tube-O-Dialyzers (GenoTechnology). After protein concentration is determined using the NI protein assay kit (GenoTechnology), PAL activity measurements will be performed on underivatized and PEG derivatized PAL samples using standard reaction conditions, as previously described. Following in vitro characterization, in vivo trials will be conducted with the most promising pegylated therapeutic candidates using the PKU mouse model.

Characterization

Protein concentration is determined using the PAL extinction coefficient (0.5 and 0.75 mg mL$^{-1}$cm$^{-1}$ for RtPAL and AvPAL, respectively) at 280 nm for non-modified protein samples and for pegylated protein samples the concentration is calculated using the NI Protein Assay (GenoTechnology) that includes sample processing to remove non-protein contaminants that might interfere with accurate protein concentration determination.

PEG-PAL products are characterized by peptide mapping techniques to determine site-specific pegylation (LC/ESI-MSD), and trinitrobenzene sulfonate (TNBS) to determine the free amine titration before and after pegylation. Peptide mapping determines the relative occupancy of pegylation at a majority of the tryptic peptides that terminate with lysine, however, due to size and multiple adjacent lysine tryptic peptides, not all sites are visible using this technique. The TNBS assay more accurately defines the average number of PEG molecules per mol of enzyme, but gives no information about which sites get pegylated. For this reason, both assays are used and are complementary to each other. Rough estimates of percent derivatization of PAL products by PEG can be determined by SDS-PAGE and native gel analyses. Enzymatic assays are used to assess specific activity before and after pegylation and to provide evidence that there is no loss of the tetrameric PAL structure.

PAL Activity Assay

The PAL activity assay is conducted using a Cary UV spectrophotometer (Cary 50) in the kinetics mode. The activity of PAL with L-phenylalanine substrate is assayed at room temperature (25° C.) by measuring the production of trans-cinnamate monitored by the absorbance increase at 290 nm (Hodgins, (1968), ibid.). The molar extinction coefficient of trans-cinnamic acid at 290 nm is 10,238 liter $M^{-1}cm^{-1}$. Reaction mixtures contain 22.5 mM phenylalanine in 100 mM Tris-HCl buffer, pH 8.5. For standard measurements the final enzyme concentration is 0.0035 mg/mL, but for kinetic studies the enzyme concentration in the assay is adjusted so that the slope at 290 nm per min is in the range of 0.005 to 0.02. Activity data is expressed as specific activity ($\mu mol \times min^{-1} mg^{-1}$). One unit of PAL is defined as that amount of enzyme that produces 1 µmol of trans-cinnamic acid per minute at room temperature.

Example 4

Generation of Pegylated NpPAL and AvPAL

In general, pegylation for both NpPAL and AvPAL involves mixing the protein with SUNBRIGHT ME-200HS 20 kDa NHS-activated PEG (NOF).

Protocol for pegylation, standard "HC" method using NHS-activated 20 kDa linear PEG:

1) The Protein was Evaluated for the Presence of Endotoxin.

A protein solution (0.1 mL) was diluted in 0.9 mL fresh MQ water and tested with a hand-held Charles River apparatus (EndoPTS) for endotoxin at the 0.5 EU/mL sensitivity level. If endotoxin was greater than 0.5 EU/mL, then endotoxin was reduced initially by Mustang E filtration, followed by Sterogene Etox resin, and less preferably by further chromatographic purification. Reduction was limited but sufficiently useful by passage over DEAE FF (Amersham) at pH 7.8.

2) Concentration and Buffer Exchange of Protein.

The protein was concentrated to greater than 25 mg/mL but less than or equal to 75 mg/mL and buffer exchanged to 50 mM $KPO_4$, pH 8.5. If a spin filter was used to prepare this concentration, the filter was first tested for endotoxin by spinning at reduced speed and time (3000 rpm, 3 minutes) with buffer alone, then testing the retained buffer for endotoxin in the same way as the protein in step 1. The buffer batch record/recipe for 50 mM KPO4, pH 8.5 consisted of water (QS to 1 L), potassium phosphate dibasic (8.4913 g/L of 48.75 mM), and potassium phosphate monobasic (0.17011 g/L of 1.25 mM). The solution was filtered through a 0.2 µm filter and stored at room temperature. The concentrated product was slowly filtered (1-2 mL/min) through a Mustang E filter acrodisc. A sample diluted and blanked with sterile TBS, pH 7.5 was measured at A280 to determine protein concentration. The extinction coefficient was 0.83 for NpPAL and 0.75 for AvPAL.

3) Pegylation of NpPAL and AvPAL.

PEG normally stored at −80° C. was warmed to room temperature. KPO4 buffer was added to PEG to resuspend by vortexing at maximum speed, and shaking tube hard in hand to ensure all large chunks were suspended. The protein was added to the well-suspended PEG solution within one minute of having first wetted the PEG and mixed by very gentle inversion. Tubes wrapped in aluminum foil were placed on the axis of a rocker and rocked very gently at room temperature for 3 hours. The tubes were filled with TBS (pH 7.5) and sterile filtered. The suspensions were either formulated immediately or stored at 4° C. until ready for formulation.

4) Formulation.

The formulation buffer recipe/batch record consisted of water (QS to 1 L), Tris-Base (3.2 mM), Tris-HCl (16.8 mM), and sodium chloride; the buffer solution was filtered through a 0.2 µm filter and stored at room temperature. The buffer solution was subjected to tangential flow filtration using a Vivaflow 50 (smaller lots) or Vivaflow 200 (larger lots) with a 100 MWCO regenerated cellulose membrane. The solution was flushed with MQ water, 0.1 N NaOH, and 200 mL water again. The solution was equilibrated with TBS, pH 7.5 at 50 mL/min cross-flow. The pH of the permeate was determined to ensure a pH of 7.5.

The solution was buffer exchanged by first diluting with TBS approximately 3-fold and returning to original volume at least four times. Cross-flow was typically 180-200 mL/min for both Vivaflow 50 and 200.

The final product was filtered through Mustang E. The presence of endotoxin was evaluated after diluting 0.1 mL with 1.9 mL sterile fresh water. If endotoxin was greater than 1 EU/mL, reduction was conducted with Sterogene Etox gel. Formulated, sterile pegylated NpPAL or AvPAL were sealed in vials and placed at −70° C. until ready for in vivo studies.

Example 5

Generation of AvPAL Variants (Cysteine Mutants)

Amino acid substitutions were made in the AvPAL polypeptide to reduce aggregation that occurs in bacterially expressed, recombinant proteins. Protein aggregation may reduce enzyme activity and/or increase immunogenicity in vivo. One such form of aggregation occurs as a result of formation of inter-chain disulfide bonds. To minimize this possibility, various AvPAL cysteine residues, alone or in combination, were replaced with serine residues.

The AvPAL polypeptide has 6 cysteine residues, at positions 64, 235, 318, 424, 503 and 565 (SEQ ID NO:4). The following AvPAL single cysteine mutants were generated: AvPAL_C64S (SEQ ID NO:7), AvPAL_C318S (SEQ ID NO:8), AvPAL_C503S (SEQ ID NO:9), and AvPAL_C565S (SEQ ID NO:10). An AvPAL double cysteine mutant, AvPAL_S565SC503S (SEQ ID NO:11), was also generated. FIGS. 3A-3E shows the amino acid sequences of these AvPAL cysteine mutants.

Cloning

The AvPAL gene was amplified from *Anabaena variabilis* genomic DNA (ATCC 29413-U, Qiagen DNeasy Kit) with forward primer AvarPALfor (5'-CACTGTCATATGAAGA-CACTATCTCAAGCACAAAG-3') (SEQ ID NO:18) and reverse primer AvarPALrev (5'-CACTGTCTCGAGATG-CAAGCAGGGTAAGATATCTTG-3') (SEQ ID NO:19). The resulting PCR product was treated with Taq and then ligated into pCR2.1 TOPO TA (Invitrogen). The resulting plasmid was named 1p40.

A 5' NheI site was added and an internal NheI site was removed by SOE-PCR. The upstream AvPAL fragment was amplified from 1p40 with forward primer N-Nhe-AvPAL (5'-CACTGTGCTAGCATGAAGACACTATCTCAAGCA-CAAAG-3') (SEQ ID NO:20) and reverse primer Nhe-AvPALrev (5'-GGAAATTTCCTCCATGATAGCTGGCT-TGGTTATCAACATCAATTAGTGG-3') (SEQ ID NO:21), and the downstream AvPAL fragment was amplified from 1p40 with forward primer Nhe-AvPAL for (5'-CCACTAAT-TGATGTTGATAACCAAGCCAGCTATCATGGAG- GAAATTTCC-3') (SEQ ID NO:22) and reverse primer AvPALrev-r (5'-ACAGTGGCGGCCGCTTAATG-CAAGCAGGGTAAGATATCTTG-3') (SEQ ID NO:23). In a single PCR reaction, the two PCR products were annealed and extended with DNA polymerase to produce the full-length AvPAL gene, and then amplified with primers N-Nhe-AvPAL and AvPALrev-r. The resulting PCR product was digested with NheI, blunted with Klenow, digested with NotI, and ligated into the pET28a+ vector (prepared by digestion with NdeI, blunting with Klenow, and digestion with NotI). The resulting plasmid was named 3p86-23.

New restriction sites were added by PCR. AvPAL was amplified from plasmid 3p86-23 with forward primer AvEcoRIfor (5'-CACTGTGAATTCATGAAGACAC-TATCTCAAGCACAAAG-3') (SEQ ID NO:24) and reverse primer AvSmaIrev (5'-CACTGTCCCGGGTTAATG-CAAGCAGGGTAAGATATCT-3') (SEQ ID NO:25). The resulting PCR product was digested with EcoRI and SmaI and ligated into EcoRI- and SmaI-digested pIBX7 vector. The resulting plasmid was named 7p56 Av3.

Cysteine Mutants

Two cysteine codons in the AvPAL gene, corresponding to positions 503 and 565 of the AvPAL polypeptide, were substituted with serine codons by site-directed mutagenesis (QuickChange XL II, Stratagene). The cysteine codon at position 503 was changed to a serine codon in plasmid 7p56 Av3 by PCR with forward primer Av_C503S (5'-GTCAT-TACGATGCACGCGCC TCTCTATCACCTGCAACTGAG-3') (SEQ ID NO:26) and reverse primer Av_C503Srev (5'-CTCAGTTGCAGGTGA-TAGAGAGGCGCGTGCATCGTAATGAC-3') (SEQ ID NO:27). The serine codon is underlined and the G to C mutation in the coding strand (C to G mutation in the non-coding strand) is indicated in bold. The resulting plasmid was named j282. The cysteine codon at position 565 was changed to a serine codon in plasmid j282 with forward primer Av_C565S (5'-CAGTTCAAGATATCTTACCC TCCTTGCATTAACCCGGGCTGC-3') (SEQ ID NO:28) and reverse primer Av_C565Srev (5'-GCAGCCCGGGT-TAATGCAAGGAGGGTAAGATATCTTGAACTG-3') (SEQ ID NO:29). The serine codon is underlined and the G to C mutation in the coding strand (C to G mutation in the non-coding strand) is indicated in bold. The resulting plasmid was named j298a.

Cysteine codons in the AvPAL gene at positions 64, 318 and 565 of the AvPAL polypeptide were similarly substituted with serine codons using the following primer pairs: C64S, forward primer Av_C64S (5'-GCAGGGTATTCAG-GCATCTTCTGATTACATTAATAATGCTGTTG-3') (SEQ ID NO:30) and reverse primer Av_C64Srev (5'-CAACAG-CATTATTAATGTAATC AGAAGATGCCTGAATACCCTGC-3') (SEQ ID NO:31); C318S, forward primer Av_C318S (5'-CAAGATCGT-TACTCACTCCGATCCCTTCCCCAGTATTTGGGGC-3') (SEQ ID NO:5) and reverse primer Av_C318Srev (5'-GC-CCCAAATACTGGGGAAG GGATCGGAGTGAGTAACGATCTTG-3') (SEQ ID NO:6); and C565S, forward primer Av_C565S (SEQ ID NO:28) and reverse primer Av_C565Srev (SEQ ID NO:29). The serine codons are underlined and the G to C mutations in the coding strands and the C to G mutations in the non-coding strands are indicated in bold.

Example 6

In Vitro Enzyme Activity of AvPAL Variants (Cysteine Mutants)

The purpose of this study was to determine the effect of serine substitution of the various cysteine residues in the AvPAL polypeptide on in vitro phenylalanine ammonia-lyase (PAL) enzyme activity.

AvPAL variants (i.e., cysteine mutants) were cloned as described in Example 5. The AvPAL cysteine mutant expression plasmids were transformed into bacteria and the AvPAL cysteine mutant polypeptides were expressed as described in Example 1 and purified as described in Example 2.

The wild-type (WT) AvPAL and AvPAL cysteine mutants were tested for in vitro PAL enzyme activity as described in Example 3. Table 1 shows that compared to unpegylated WT AvPAL, the in vitro PAL specific activity of the purified, unpegylated AvPAL cysteine mutant proteins was reduced by serine substitution of the cysteine residue at position 64 (AvPAL_C64S), but was not adversely affected by serine substitution of the cysteine residues at either of positions 503 or 565, or at both positions 503 and 565 (AvPAL_C503S, AvPAL_C565S, and AvPAL_C565SC503S, respectively).

TABLE 1

Specific Activity of AvPAL Cysteine Mutants

| AvPAL Protein | Pegylation | Specific Activity (U/mg) |
| --- | --- | --- |
| WT AvPAL | − | 1.7 |
| AvPAL_C503S | − | 1.9 |
| AvPAL_C64S | − | 1.3 |
| AvPAL_C565S E1 | − | 2.0 |
| AvPAL_C565S E2 | − | 2.1 |
| AvPAL_C565SC503S | − | 2.2 |
| WT AvPAL | + | 1.1 |
| AvPAL_C565SC503S | + | 1.1 |

To determine whether the introduction of the serine residues had any effect on enzymatic activity of pegylated AvPAL proteins, the WT AvPAL and double cysteine mutant, AvPAL_C565SC503S, were pegylated as described in Example 4. Table 1 shows that the in vitro PAL specific activity of the pegylated AvPAL protein was not adversely affected by serine substitution of the cysteine residues at both positions 503 and 565.

Example 7

In Vitro Biochemical Characterization of AvPAL Variants (Cysteine Mutants)

The purpose of this study was to determine the effect of serine substitution of the various cysteine residues in the AvPAL polypeptide on: (1) accelerated stability; (2) aggregate formation; and (3) site-specific pegylation.

Accelerated Stability

The effect of serine substitution of cysteine residues in AvPAL on in vitro stability was determined by storing the purified AvPAL cysteine mutants, either pegylated or un-pegylated, for various time periods at 37° C., and then measuring the in vitro PAL specific activity of these proteins as described in Example 3.

Wild-type AvPAL and AvPAL cysteine mutants, either upegylated or pegylated, were prepared as described in Example 4.

Figure 4B:
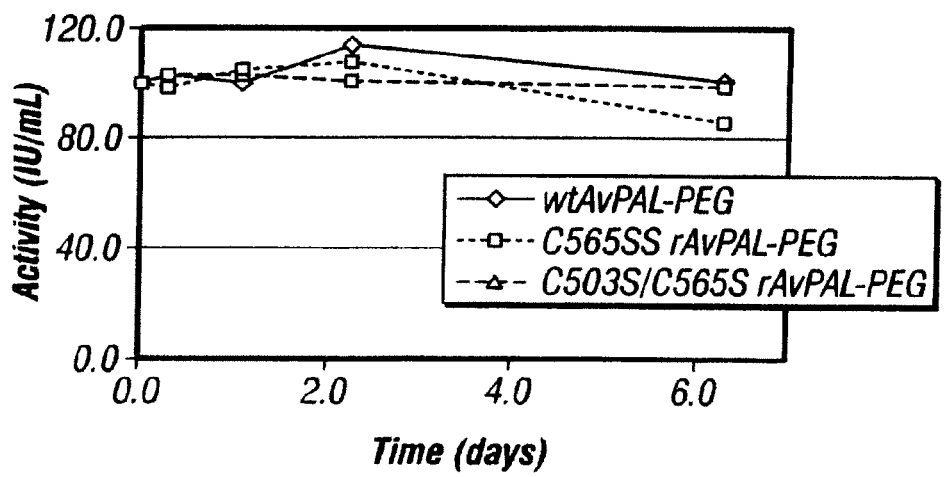

As shown in FIG. 4A, the specific activities of the unpegylated AvPAL proteins were stable for at least 5 days at 37° C., and were not adversely affected by serine substitution of the cysteine residues at position 565, or at both positions 503 and 565. Similarly, as shown in FIG. 4B, the specific activities of the pegylated AvPAL proteins were stable for at least 6 days at 37° C. The single cysteine AvPAL mutant, AvPAL_C565S, showed somewhat reduced stability compared to wild-type AvPAL and the double cysteine AvPAL mutant, AvPAL_C565SC503S, after 6 days at 37° C.

Aggregate Formation

The effect of serine substitution of cysteine residues in AvPAL on formation of protein aggregates in solution was determined by separating the purified, unpegylated wild-type AvPAL and AvPAL cysteine mutants by either denaturing and native gel electrophoresis or by SEC-HPLC.

The purified AvPAL preparations were separated by gel electrophoresis under either denaturing conditions (4-12% NuPAGE Bis-Tris) or native conditions (8% Tris-Gly, pH 8.3). The separated AvPAL proteins were stained with Coomassie Blue.

The purified AvPAL preparations were separated by SEC-HPLC. AvPAL proteins were loaded onto a TSK gel column (G3000SWxl, 7.8 mm×30 cm, 5 μm (Tosoh Bioscience, LLC)) in 20 mM Na-phosphate, 300 mM NaCl, pH 6.9, and eluted at a flow rate of 0.5 mL/min. The separated AvPAL proteins were analyzed on an Agilent series 1100 spectrometer.

Figure 5A:
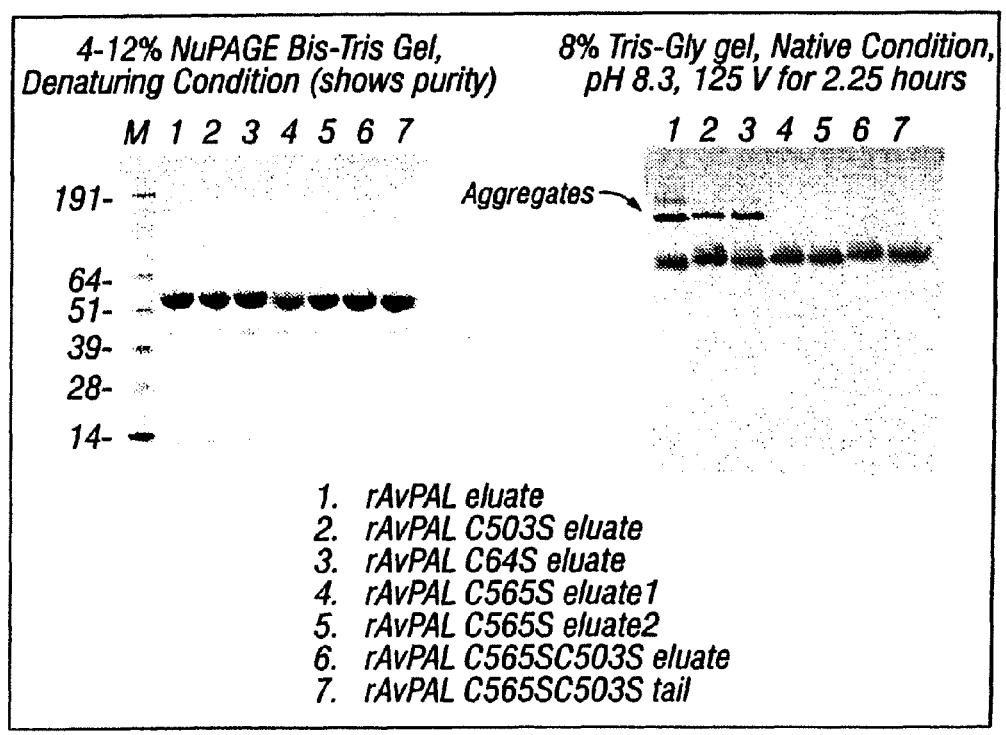
FIGS. 5A-5B depict the effect of cysteine to serine substitutions in AvPAL on formation of protein aggregates in solution as analyzed by (A) gel electrophoresis under denaturing conditions (left panel) or native conditions (right panel) or (B) SEC-HPLC.
Figure 5B:
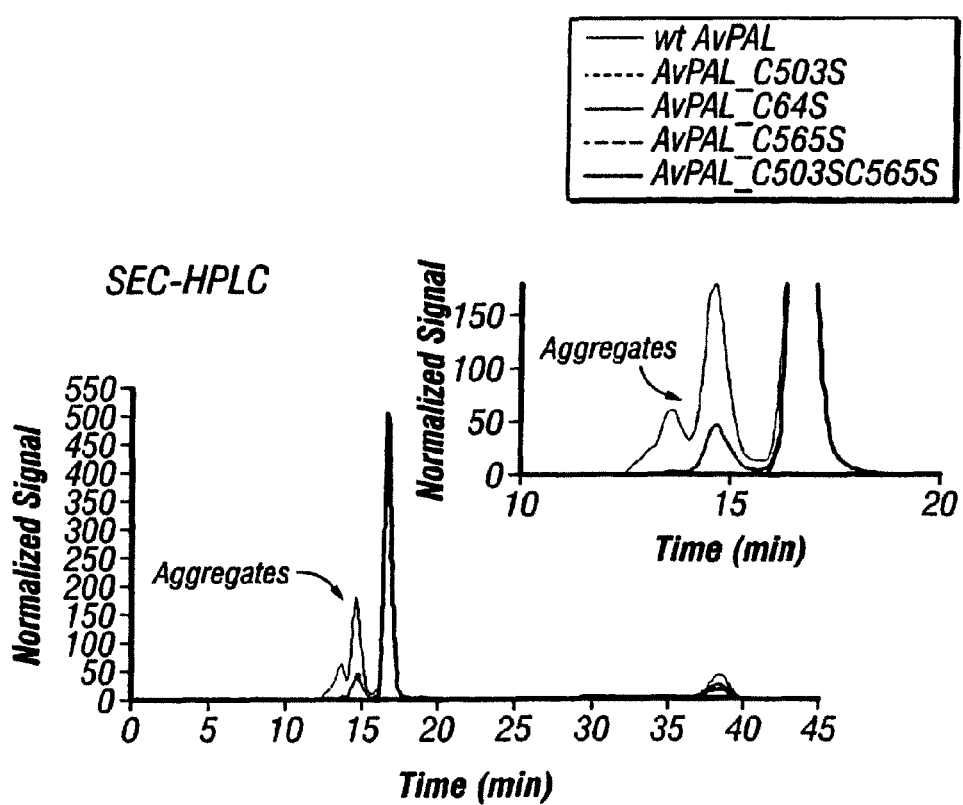

Aggregates were present in the wild-type AvPAL preparation and in the AvPAL_C503S and AvPAL_C64S preparations, but not in the AvPAL_C565S and AvPAL_C565SC503S preparations, as judged by either gel electrophoresis (FIG. 5A) or SEC-HPLC (FIG. 5B).

Site-Specific Pegylation

The effect of serine substitution of cysteine residues in AvPAL on site-specific pegylation was determined by pegylating the wild-type AvPAL and double cysteine mutant AvPAL_C503SC565S as described in Example 4, and then comparing the relative pegylation at the AvPAL lysine residues: K2, K10, K32, K115, K145, K195, K301, K335, K413, K419, K493, K494 and K522.

Approximately 100 μg (10 μL at 10 μg/μL) of unpegylated or pegylated AvPAL proteins were denatured in 8 M urea. The denatured proteins were then digested in a 100 μL reaction volume with trypsin in 0.8 M urea at pH 8.2 overnight (~20 hours) at 37° C. The trypsin-digested proteins were reduced by treatment with 1 μL of 1 M DTT for 1 hour at 37° C., followed by quenching with 3 μL 15% TFA. Digested proteins were separated on a C18 reverse-phase column. Percent pegylation of each of the pegylated AvPAL peptides was calculated by subtractive peptide mapping of the corresponding unpegylated peptide.

Figure 6:
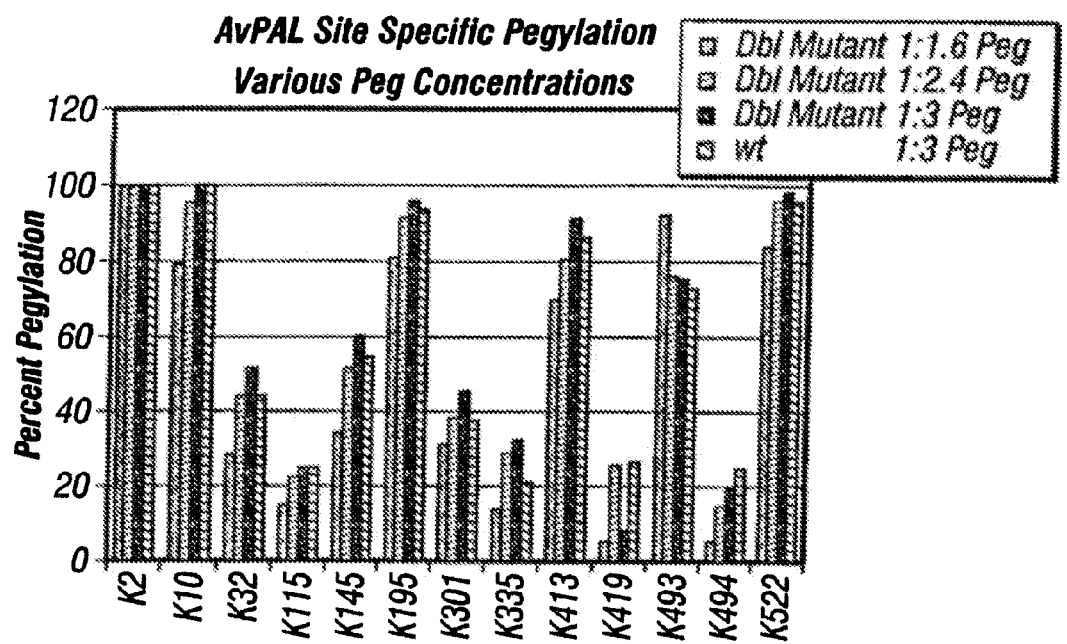
FIG. 6 depicts the effect of cysteine to serine substitutions at positions 565 and 503 in AvPAL (AvPAL_C565SC503S) on site-specific pegylation at various PEG concentrations.

As shown in FIG. 6, at a ratio of AvPAL protein:PEG of 1:3, there was no striking difference in the percent pegylation of any of the lysine (K) residues with the possible exception of K419, in which the percent pegylation of the double cysteine mutant C565SC503S was lower compared to wild-type AvPAL. However, the results obtained using the double cysteine mutant at increasing AvPAL protein:PEG ratios, in which no dose-response relationship was observed, taken together with the relatively small percent pegylation, indicates that the observed differences at K1419 are not likely to be meaningful. Thus, serine substitution of cysteine residues at positions 503 and 565 does not appear to affect site-specific pegylation of AvPAL.

Example 8

Detection of Pegylated Recombinant *Anabaena variabilis* Phenylalanine Ammonia-Lyase (rAvPAL-PEG) in Plasma The purpose of this assay development was to create a method to determine the plasma concentration of pegylated recombinant *Anabaena variabilis* phenylalanine ammonia-lyase (rAvPAL-PEG) or variant thereof. In particular, an enzyme-linked immunosorbent assay (ELISA) method was developed to detect rAvPAL-PEG in rat, monkey, and human plasma.

Materials

The following antibodies and chemicals were used: AvPAL (unpegylated enzyme) and rAvPAL-PEG (pegylated enzyme) in formulation buffer (10 mM Tris-HCl, 150 mM NaCl, pH 7.5); see Examples 1, 2 and 4 above, as well as U.S. Pat. No. 7,531,341; capture reagent: affinity-purified rabbit anti-rAvPAL-PEG polyclonal antibody BP79ex (prepared using standard methods known to those in the art); competing antibody: Protein G-purified rabbit anti-rAvPAL-PEG polyclonal antibody BP80 (prepared using standard methods known to those in the art); detection reagent: anti-PEG mouse monoclonal IgM antibody (Academia Sinica, Cat No. AGP3); biotinylated anti-PEG mouse monoclonal IgM antibody; conjugate: HRP-conjugated Streptavidin (Pierce, Cat No. 21127); Dulbecco's phosphate buffered saline (DPBS), 1× (Cellgro, Cat No. 21-031-CV); sulfuric acid ($H_2SO_4$), 12 N (VWR, Cat No. VW3481-1); glycine (Sigma, Cat No. 67126); BupH Carbonate-Bicarbonate Buffer Pack (Pierce, Cat No. 28382); Tween 20 (Acros Organics, VWR, Cat No. 233360010); Trizma (Sigma, Cat No. T6066-500G); TMB 2 Component (BioRad Component A, Cat No. 210002430; Component B, Cat No. 210002327); ProClin 300 (Supelco, Cat No. 48912-V); bovine serum albumin (BSA), Fraction V, Omnipure (EMD, VWR, Cat No. 2930); pooled rat plasma LiHeparin (Bioreclamation, Inc. Cat No., RATPLIHP); pooled cyno plasma LiHeparin (Bioreclamation, Inc. Cat No., CYNPLIHP); and pooled human plasma LiHeparin (Bioreclamation, Inc., Cat No. HMPLIHP).

The particular antibodies used here are illustrative and not meant to be limiting in any way. Different capture reagents and competing antibodies can be used in this assay, for example, affinity-purified rabbit anti-rAvPAL-PEG polyclonal antibody BP83ex as capture reagent, and Protein G-purified rabbit anti-rAvPAL-PEG polyclonal antibody BP84 as competing antibody. Different detection reagents can be used in this assay, for example, rabbit monoclonal anti-PEG IgG (Epitomics, Inc.).

The following plasticware and disposables were used: pH paper, Baker-pHIX (JT Baker, VWR, Cat No. 4393-01); 1.2 mL cluster tubes (Costar, Cat No. 11508); microcentrifuge tubes, 1.5 ml, (USA Scientific, VWR, Cat No. 1615-550); flat bottom MaxiSorp 96-well plate (Nunc International, VWR, Cat No. 12-565-135); microplate adhesive film sealer (USA Scientific, Cat No. 2920-0000); pipetman tips: 20 μL, 250 μL, and 1000 μL (Rainin Instruments, Cat Nos. GPS-L1000, GPS-L250, GPS-L10); reagent reservoir, 50 mL Capacity (Corning, VWR, Cat No. 07200127); and serological pipettes, 10 mL and 25 mL (VWR, Cat Nos. 13-678-11D and 13-678-11E).

The following equipment were used: Elx405 Select Plate Washer (Bio-Tek); multichannel pipetman, 12-well, LTS 20-200 μL (Rainin Instruments); multichannel pipetman, 12-well, LTS 100-1200 μL (Rainin Instruments); pipet-aid, multi-speed, Drummond (VWR, Cat No. 13-681-15E); SOFTmax Pro v3.0 (Molecular Devices); SpectraMax PLUS Microplate Spectrophotometer (Molecular Devices); timer, three channel alarm (VWR, Cat No. 62344-600); and titer plate shaker (Barnstead/Lab-Line Instruments).

Buffers

The following buffers were used: acidification reagent: 0.1 M glycine, pH 2.7; neutralization buffer: 0.5 M Tris-HCl, pH 8.5; coating buffer (CB): carbonate-bicarbonate buffer, pH 9.2; blocking buffer (BB): 1×DPBS/0.05% Tween 20/5% BSA or 1×DPBS/5% BSA; wash buffer (WB): 1×DPBS/ 0.1% Tween 20/0.05% Proclin 300; TMB substrate solution: 10 mL component A and 1.2 mL component B; and stop solution: 2N $H_2SO_4$.

ELISA Protocol

The following ELISA protocol was used. The capture antibody BP79ex was prepared in CB to a final concentration of 1 µg/mL, and 100 µL/well was dispensed in a flat bottom MaxiSorp 96-well plate, followed by incubating the plate overnight at 4° C. The plate was washed 3× with 300 µL/well WB. BB was added at 300 µL/well, and the plate was incubated with shaking for 2 hours at room temperature (RT). After removing BB, the plate was washed 3× with 300 µL/well WB. For acidification, 1 mg/mL rAvPAL-PEG standard stock solutions were diluted 20-fold in the appropriate plasma matrix to a final concentration of 50 µg/mL. Four (4) volumes of 0.1 M glycine, pH 2.7, were added to the diluted plasma standards, followed by incubating the plate for 30 min at RT. Standards and samples were neutralized with 1 volume 0.5 M Tris-HCl, pH 8.5. The neutralized standards and samples were then diluted to a final plasma concentration of 2% (v/v) by adding BB. Subsequent samples and standards dilutions were made in BB containing 2% rat plasma to match the plasma matrix. Final dilutions of standards and samples were added at 100 mL/well to the plate, followed by incubating the plate without shaking for 2 hours at 37° C. After incubation, the plate was washed 3× with 300 µL/well WB. The Detection Antibody (mouse anti-PEG monoclonal IgM antibody conjugated to biotin) was diluted to 1 µg/mL in BB and then dispensed at 100 µL/well, followed by incubating the plate with shaking for 1 hour at RT. After incubation, the plate was washed 3× with 300 µL/well WB. The Streptavidin HRP was diluted to 1 µg/mL in BB and then dispensed at 100 µL/well, followed by incubating the plate with shaking for 1 hour at RT. After incubation, the plate was washed 3× with 300 µL/well WB. TMB Substrate Solution was added to the plate at 100 µL/well, followed by incubating the plate for 30 min at RT. Stop Solution was added to the plate at 100 µL/well, followed by reading the plate for absorbance at 450 nm. It should be understood that the concentrations of antibodies used in this assay may differ in assays using alternative antibodies.

Assay Design Parameters

To establish the assay format and determine the concentrations of capture and detection antibodies and additional reagents, multiple rabbit polyclonal anti-AvPAL antibodies were tested to identify the optimal coating antibody (i.e., BP77, BP78, BP79, BP80). For coating, Protein G-purified rabbit polyclonal anti-AvPAL antibodies were tested at 5 µg/mL upon dilution in CB. Some of these antibodies were tested for antigens diluted in CB and in 2% rat plasma to identify antibodies that would give stronger signals with minimal matrix interference. The affinity-purified rabbit polyclonal anti-AvPAL antibody BP79ex was also tested as a replacement for the affinity-purified antibodies.

The initial screening of BP77, BP78, BP79, and BP80 antibodies identified BP79 and BP80 as lead candidates for coating antibody. Further testing of these antibodies at 2 µg/mL in CB and in 2% rat plasma identified BP79 as the best coating antibody. Further testing demonstrated that the affinity-purified BP79 antibody, BP79ex, showed improved sensitivity and linearity, and the coating concentration was reduced to 1 µg/mL. Additional experiments demonstrated equivalent linearity and range in the ELISA when used to detect the double cysteine mutant, pegylated AvPAL, rAvPAL-PEG_C565SC503S, having the cysteine residues at positions 503 and 565 substituted with serine residues, as compared to the wild-type rAvPAL-PEG. Further experiments identified BP83ex as a suitable coating antibody and BP84 as a suitable competing antibody.

Acidification

Development of a suitable assay to detect an extensively pegylated therapeutic enzyme (i.e., an enzyme having a sufficient number of polyethylene glycol (PEG) molecules attached such that at least some of the enzyme's immunogenic epitopes are masked by PEG molecules) in a body fluid or tissue sample from a mammal requires finding a way to expose the immunogenic epitopes of the therapeutic enzyme (i.e., AvPAL) for capture by an immobilized antibody specific for the target therapeutic enzyme, maximizing the number of epitopes recognized by the antibodies, while at the same time minimizing the number of epitopes masked by the PEG molecules. To accomplish this, various methods were evaluated, including acidification, to denature and subsequently renature the target pegylated therapeutic enzyme (i.e., rAvPAL-PEG).

Acidification/neutralization has been used to remove bound binding proteins in blood from interfering in an ELISA used to measure transforming growth factor beta 1 (TGF-β1) (Kropf et al., *Clin. Chem.* 43:1965-1974 (1997)). In this procedure, plasma or serum samples were acidified to pH 2 to 3 with HCl, and subsequently neutralized to pH 7 to 8 with NaOH. Acidification/neutralization has also been used to dissociate inhibitor complexes from interfering in an ELISA to measure human tissue plasminigen activator (tPA) in plasma samples (Ranby et al., *Thromb. Haemost.* 61:409-414 (1989)). In this procedure, samples were acidified by adding an equal volume of 1 M potassium acetate buffer, pH 3.9, followed by neutralization with an equal volume of 0.5 M Tris containing 0.2 M $NaH_2PO_4$. Heat denaturation and acidification/neutralization have been used to dissociate immune complexes that interfere with an ELISA to detect HIV-1 p24 antigen in serum or plasma (Schupbach et al., *AIDS* 10:1085-1090 (1996)).

The effect of acidification on assay sensitivity and robustness was evaluated.

Standards were incubated under different acidification/ neutralization conditions with the following acidification reagents and neutralization buffers: (1) acidify with 0.1 M glycine, pH 2.7, neutralize with 0.5 M Tris-HCl, pH 8.5; (2) acidify with 0.5 M acetic acid and 0.2 M NaCL, neutralize with 0.5 M Tris-HCl, pH 8.5; (3) acidify with 0.5 N HCl, neutralize with 0.5 M Tris-HCl, pH 8.5; and (4) acidify with 2 N HCl, neutralize with 2 N NaOH; or no acid treatment.

Pegylation of AvPAL decreased the accessibility of capture antibodies (i.e., BP79ex) to potential epitopes. Therefore, it was necessary to acidify the pegylated AvPAL to reliably detect these epitopes. Treatments (1) and (3) gave better results than treatment (4) or no treatment (i.e., buffer curve). Treatment (3), however, often showed a viscous, white precipitate at the higher end concentrations that drastically lowered the signal. Treatment (2) also showed improvement over no treatment, but was not deemed significant over treatment (1) in the presence of plasma. Therefore, treatment (1) was deemed the most feasible and reliable acidification method.

Quantitative Range

The quantitative range of the ELISA assay was determined by running standard curves of rAvPAL-PEG ranging from 1000 to 0.244 ng/mL when diluted in 2% rat plasma. The quantitative range was established by running Quality Controls (QCs) from a stock of rAvPAL-PEG at various concentrations in 2% rat plasma (LiHeparin).

The standard curve, for example, of 0, 0.244, 0.977, 3.906, 15.625, 62.5, 250, and 1000 ng/mL rAvPAL-PEG in 2% plasma was evaluated. Curve fits were generated by plotting the absorbance at 450 nm for the average of each triplicate versus nominal concentration and fitting with the four-parameter model. The accuracy of back-calculation of each point on the standard curve was evaluated along with the $R^2$ value for the overall fit.

The four-parameter model in SoftMax Pro generated a high quality fit for standard curves constructed in 2% rat, monkey, and human plasma. The back-calculation accuracy of the expected concentration for at least 6 of the 7 non-zero standards was 86-124%, 76-110%, and 92-104% for rat, monkey and human plasma, respectively.

To establish the upper limit of quantitation (ULOQ), rAvPAL-PEG was prepared at 350, 300, and 200 ng/mL. The lower limit of quantitation (LLOQ) was prepared at 5, 3, and 2 ng/mL. For rat plasma, the ULOQ and LLOQ were 350 ng/mL and 5 ng/mL respectively, with accuracy between 71-74%. For monkey plasma, the ULOQ was 350 ng/mL and the LLOQ was 2 ng/mL, with accuracy between 75-94%. For human plasma, the ULOQ was 350 ng/mL and the LLOQ was 2 ng/mL, with accuracy between 73-97%.

Selectivity

The selectivity of the ELISA assay was determined by analyzing samples of rAvPAL-PEG in 2% plasma from different lots of rat, monkey or human plasma.

Selectivity is a measure of variation in accurately determining analyte concentration between different lots of plasma due to interfering substances. The accuracy of determining rAvPAL-PEG concentration in plasma from multiple individuals was evaluated by analyzing samples of 200, 20, and 6 ng/mL rAvPAL-PEG in 2% plasma from three lots of rat, monkey, or human plasma. These controls were compared against a standard curve constructed in a 2% pooled plasma lot from each species. The relative accuracy for each lot of rat plasma (in relation to the pooled plasma) was 46%-115% for 6, 20, and 200 ng/mL. However, if the 20 ng/mL concentration is not considered, the relative accuracy across different lots of rat plasma is 84%-115%. The relative accuracy for monkey plasma was 84-153% for 6, 20, and 200 ng/mL. The relative accuracy for the human selectivity experiment was 83-246% for 6, 20, and 200 ng/mL. However, if one sample was excluded from the analysis, the accuracy across human plasma lots was 83%-123%. In addition, the high quality control had low back calculated concentration, which skewed nominal and relative accuracy. Because the variable accuracy appears random across the high, mid, and low concentrations, selectivity is not likely to be a major factor.

Specificity

The specificity of the ELISA assay for the rAvPAL-PEG molecule when challenged with AvPAL or an inactivated PEG molecule was evaluated. A standard curve was prepared from 1000 to 0.244 ng/mL rAvPAL-PEG. AvPAL and inactivated PEG were spiked into plasma separately and tested in the standard ELISA assay.

The absorbance for rAvPAL-PEG samples was proportional to concentration across the quantitative range. The absorbance for 200 ng/mL inactivated PEG, unpegylated AvPAL, and an unrelated protein, such as recombinant human arylsufatase B (rhASB), was below the limit of detection (LOD), indicating that the assay is specific to rAvPAL-PEG.

Interference from Plasma Matrix

The effect of different matrices (i.e., rat, monkey and human plasma) on the concentration-response relationship was evaluated. Standard curves in plasma at various percentages from different species were prepared, and the concentration of standards in the presence of plasma as compared to the concentration of standards in 2% plasma was calculated to determine the accuracy relative to the nominal concentration.

Samples of rAvPAL-PEG at 200, 20, and 6 ng/mL in 10%, 5%, and 2% plasma were compared against standard curves constructed in 2% rat, monkey, and human plasma. The accuracy was 78%-122% for 6, 20, and 200 ng/mL in 2% rat, monkey, and human plasma. In 5% human plasma, the accuracy was 79%-98% for 6, 20, and 200 ng/mL. Therefore, the rat, monkey, and human plasma dilutions of 1:50 (2%) are acceptable for sample analysis. Human plasma dilution of 1:25 (5%) was also found to be acceptable. Plasma dilutions of 1:10 (10%) were not acceptable because accuracies in these matrices were too low for rat and monkey plasma. For 10% human plasma, the accuracy was slightly better, but still not acceptable across the entire range (6-200 ng/mL).

Interference from Antibodies

The interfering effect of anti-rAvPAL-PEG antibodies on the concentration-response relationship was evaluated by pre-incubating combinations of anti-rAvPAL-PEG antibodies (BP80 and BP79ex) at various concentrations with rAvPAL-PEG at various concentrations for 30 min, carrying out the standard acidification procedure, and then examining the accuracy of the controls in the presence of increasing amounts of antibody.

Samples of 200, 20 and 6 ng/mL rAvPAL-PEG in rat plasma containing 0, 4, 40, and 40 ng/mL affinity-purified rabbit anti-rAvPAL-PEG antibody (BP79ex) were analyzed relative to a standard curve in 2% plasma. BP79ex is the capture antibody for this ELISA. Accuracy of the 6 ng/mL rAvPAL-PEG concentrations decreased as antibody concentrations increased. The relative accuracy of 200 ng/mL rAvPAL-PEG was within 87%-95% for up to 400 ng/mL antibody versus 0 ng/mL antibody. However, nominal accuracy for 200 ng/mL was poor even without interfering antibody. The relative accuracy for 20 ng/mL was within 93%-96% for up to 400 ng/mL antibody versus 0 ng/mL antibody. The relative accuracy for 6 ng/mL was 76%-107% for up to 400 ng/mL antibody versus 0 ng/mL antibody. Although it is difficult to predict the likelihood or impact of antibody interference on accuracy prior to non-clinical and clinical studies, we did not measure a clear effect of BP79ex on this assay.

Dilution Linearity

To ensure that accurate results are reported independent of the final dilution factors that fall within the quantitative range of the assay, the dilution linearity was investigated for rAvPAL-PEG. Samples of 1000, 200, and 20 ng/mL rAvPAL-PEG in 2% rat plasma were analyzed at dilutions of 1:2, 1:4, 1:8, and 1:16 (in addition to the initial 1:50 dilution). For results within the quantitative range of the assay, the plasma concentration was calculated as dilution factor multiplied by the concentration of the dilution. Within the quantitative range of the assay, the percent accuracy for individual dilutions was within 69%-116% of the expected value. The 1000 ng/mL sample did not accurately dilute.

Precision and Accuracy

To assess precision, samples of rAvPAL-PEG were prepared at 200, 20 and 6 ng/mL in 2% rat plasma and analyzed against standard curves. Two analysts evaluated intra-assay precision and inter-assay precision with three experiments over at least a 2-day period. Intra-assay (within run) precision (CV %) ranged from 1.6%-11.9% across the quality control concentrations tested. Inter-assay (between runs) precision (CV %) was 17.7%, 10.6% and 17.3% for 200 ng/mL, 20 ng/mL and 6 ng/mL, respectively. Accuracy was 85.9%, 115.9% and 103.3% respectively for these three quality controls.

Robustness of Reagent Concentrations and Incubation Times

The capacity of the ELISA assay to remain unaffected by small, but deliberate variations in the method parameters and provide an indication of its reliability during normal usage was determined.

Standard curves of rAvPAL-PEG were analyzed using minimum and maximum reagent concentrations of BP79ex, and anti-IgM at 90% and 110% of the optimized values of 1 µg/mL. The accuracy of the back-calculated minimum reagent concentration (90%) standard curve did not meet acceptance criteria and had accuracies of 25%-41% across the standard curve range. The accuracy of the back-calculated maximum reagent concentration (110%) plate ranged from 82%-126% across the quantitative range. The low end of the curve suffered the most from the deviation from optimal conditions. Overall, the maximum concentration standard curve was acceptable with 5 of 7 non-zero points demonstrating good accuracy. It is recommended that the optimal conditions are adhered to, but some modest increase in BP79ex and anti-IgM antibody concentration can be tolerated.

A minimum and a maximum plate were tested with the 10% variation away from the optimal incubation times of each critical assay steps. The cumulative decrease in incubation times at each critical step adversely impacted accuracy of quality controls. The minimal incubation plate had nominal accuracies of 71%-138% for the 200, 20, and 6 ng/mL quality controls. In contrast, the maximum incubation time-plate had excellent curve fit and acceptable accuracy (99%-121%). Therefore, it is recommended that the optimal incubation times are adhered to, but some modest (10% increase) in time of incubation at each step is likely to be tolerated in the assay.

Reagent Stability

The stability of the reagents (e.g., antibodies and quality controls) over a time period equal to the typical sample preparation, sample handling, and analytical run times using the intended storage temperatures was characterized.

Samples of 200, 20 and 6 ng/mL rAvPAL-PEG were frozen at −70° C. Samples subjected to multiple freeze-thaw cycles (FT 1-FT 3), or storage overnight at 4° C., or for 4 hours at RT, were analyzed against a freshly prepared standard curve along with freshly thawed samples (FT 0). The signal for the 6 ng/mL samples was above the limit of quantitation for all stability tests and will not be considered herein. However, the mid- and high-quality controls (20 ng/mL and 200 ng/mL) were stable after 3 freeze thaw cycles with nominal accuracy of 114% and 85%, respectively. The stability of the mid- and high-quality controls (20 ng/mL and 200 ng/mL) stored overnight at 4° C. had nominal accuracies of 89% and 66%, and relative accuracies of 101% and 107%, respectively. RT stability after 4 hours demonstrated nominal accuracies of 65% for the high quality control, and 74% for the mid quality control, and relative accuracies of 105% and 84%, respectively. These values indicate that test samples could tolerate up to three freeze-thaw cycles. Storage of test samples overnight at 4° C. or for greater than 4 hours at RT is tolerated.

Example 9

Detection of IgG Antibodies Specific to *Anabaena variabilis* Phenylalanine Ammonia-Lyase in Serum The purpose of this assay development was to create a method to assess the immunogenicity of recombinant *Anabaena variabilis* phenylalanine ammonia-lyase (AvPAL) or variant thereof. In particular, an enzyme-linked immunosorbent assay (ELISA) method was developed to detect IgG antibodies to AvPAL in serum.

Materials

The following enzymes were used: AvPAL (unpegylated enzyme) and rAvPAL-PEG (pegylated enzyme) in formulation buffer (10 mM Tris-HCl, 150 mM NaCl, pH 7.5); see Examples 1, 2 and 4 above, as well as U.S. Pat. No. 7,531,341.

The following antibodies were used: BP79: Protein G-purified rabbit anti-rAvPAL-PEG IgG (Positive Control) in 1×DPBS, pH 7.0-7.2; BP79ex: affinity-purified rabbit anti-rAvPAL-PEG IgG (Positive Control) in 1×DPBS, pH 7.0-7.2; BP80: Protein G-purified rabbit anti-rAvPAL-PEG IgG (Positive Control) in 1×DPBS, pH 7.0-7.2; BP14: rabbit anti-recombinant human arylsulfatase B (rhASB) antiserum; J3549: purified rabbit anti-rhASB IgG; quality control (QC) high positive control (HP) anti-rAvPAL-PEG neat rat serum, 042-371 (SNBL USA, Inc.); QC mid positive control (MP) anti-rAvPAL-PEG neat rat serum, 042-372 (SNBL USA, Inc.); QC low positive control (LP) anti-rAvPAL-PEG neat rat serum, 042-372 (SNBL USA, Inc.); detection reagent 1: HRP-conjugated donkey anti-mouse IgG (Jackson ImmunoResearch, Cat. No. 715-065-150); detection reagent 2: HRP-conjugated goat anti-rat IgG Fc (Jackson ImmunoResearch, Cat. No. 112-035-008); detection reagent 3: HRP-conjugated goat anti-rat IgG+IgM (H+L) (Jackson ImmunoResearch, Cat. No. 111-036-068); detection reagent 4: HRP-conjugated goat anti-rabbit IgG (H+L) (Jackson ImmunoResearch, Cat. No. 111-036-045); detection reagent 5: HRP-conjugated donkey anti-rabbit IgG (H+L) (Abcam, Cat. No. ab6721-1); detection reagent 6: HRP-conjugated goat anti-human IgG Fc (Jackson ImmunoResearch, Cat. No. 111-036-098); detection reagent 7: HRP-conjugated goat anti-human IgA+IgG+IgM (H+L) (Jackson ImmunoResearch, Cat. No. 111-036-064); and detection reagent 8: goat anti-rabbit IgG Fc (Jackson ImmunoResearch, Cat. No. 111-006-046).

The following matrices were used: C57 mouse serum (Fitzgerald, Cat No. 88-NM35); C57BL6 mouse serum (Bioreclamation, Inc., Cat No. MSESRM.C57); C57BL6 mouse serum (Rockland, Code No. D208-00-0050); pooled and individual naïve-normal rat serum (Bioreclamation, Inc., Cat No. RATBREC); pooled naïve-normal Beagle dog serum (Bioreclamation, Inc., Cat No. BGLBREC); pooled naïve-normal rabbit serum (Bioreclamation, Inc., Cat No. RABBREC); pooled and individual naïve-normal Cynomolgous monkey serum, Mauritius origin (Bioreclamation, Inc., Cat No. CYNBREC, CYNSRM); and pooled and individual naïve-normal human serum (Bioreclamation, Inc., Cat No. HUMSRM; The Binding Site, Cat No. CUS057).

The following ELISA reagents were used: coating buffer: 1×DPBS (Mediatech, Fisher Cat No. MT-21-031-CV); wash buffer 1:1×DPBS/0.1% Polysorbate-20/0.05% Proclin 300; wash buffer 2:1×DPBS/0.25% Polysorbate-20/0.05% Proclin 300; bovine serum albumin (BSA), fraction V, Omnipure (EMD, VWR Cat No. 2930); blocking buffer 1: Blocker Casein in PBS (Pierce, Cat No. 37528); blocking buffer 2: Blocker Casein in TBS (Pierce, Cat No. 37532); blocking buffer 3: SuperBlock T20 TBS (Pierce, Cat No. 37536); blocking buffer 4: StartingBlock T20 PBS (Pierce, Cat No. 37539); development reagent: TMB Peroxidase EIA Substrate Kit, 250 mL (BioRad, Cat No. 172-1066); and stop solution: 2 N $H_2SO_4$.

The following chemicals were used: de-ionized water (MilliQ filtered); Dulbecco's phosphate buffered saline (DPBS), 1× (Mediatech, Fisher Cat No. MT-21-031-CV); Dulbecco's phosphate buffered saline (DPBS), 10× (Mediatech, Fisher Cat No. MT-20-031-CV); sulfuric acid ($H_2SO_4$), 11 N (VWR, Cat No. VW3481-1); polysorbate-20 (Acros Organics, VWR Cat No. 233360010); and Proclin 300 (Supelco, Cat No. 4-8126).

The following plasticware and other materials were used: assay dilution block: 96-wwll, Polypropylene, V-bottom, non-sterile, 2 mL well (VWR, Cat No. 40002-012); ELISA plate: 96-well, Maxisorp, flat bottom "F" (Nalge/Nunc International, VWR Cat No. 12-565-135); microcentrifuge tubes, 1.5 mL (USA Scientific, VWR Cat No. 1615-550); microcentrifuge tubes, 2.0 mL (Eppendorf, VWR Cat No. 62111-754); microplate adhesive film (USA Scientific, Cat No. 2920-0000); pipetman tips: 20 µL, 250 µL, and 1000 µL (Rainin Instruments, Cat Nos. GPS-L1000, GPS-L250, GPS-L10); reagent reservoir, 50 mL capacity (Corning, VWR Cat No. 82026-350); and serological pipettes, 10 mL and 25 mL (VWR, Cat No. 13-678-11D and 13-678-11E).

The following equipment and software were used: Elx405 Select Plate Washer (Bio-Tek); multichannel pipetman, 12-well, LTS 20-200 µL (Rainin Instruments); multichannel pipetman, 12-well, LTS 100-1200 µL (Rainin Instruments); pipet-aid, multi-speed, Drummond (VWR, Cat No. 13-681-15E); SOFTmax Pro v 3.0 (Molecular Devices); SpectraMax PLUS Microplate Spectrophotometer (Molecular Devices); timer, three channel alarm (VWR, Cat No. 62344-600); and titer plate shaker (Barnstead/Lab-Line Instruments).

ELISA Protocol

Preparation of Samples.

Serum samples for screening and titering were initially diluted 1:50. For titering, the samples were then serially diluted three-fold in Blocking Buffer 1. A four-dilution factor cluster was chosen based on the screening assay signal where one dilution factor sample will fall above the established cutpoint. For suspected high titers, samples were diluted at a higher initial dilution, and then serially diluted three-fold thereafter.

Preparation of Positive Controls.

Positive controls were prepared in Blocking Buffer 1 at 10, 100, and 500 ng/mL. The positive control was BP80, a Protein G-purified rabbit polyclonal antibody against rAvPAL-PEG. An analogous lot of BP79 and BP79ex (affinity-purified anti-AvPAL antibodies from BP79) were also used in specialized applications during development. The detection reagent used for this control was Detection Reagent 5, an HRP-conjugated goat anti-rabbit-IgG diluted to 1:5,000 in Blocking Buffer 1.

ELISA Procedure.

AvPAL was prepared at 1 µg/mL in Coating Buffer (1×DPBS), dispensed at 100 µL per well into the ELISA plate (Nalgen/Nunc MaxiSorp surface), and incubated 12 to 20 hours (overnight) at 4° C. Blocking Buffer 1 (Blocker Casein PBS) was added at 300 µL/well and incubated on a shaker for 1 hour at room temperature (RT). Blocking Buffer 1 was removed by pouring into a waste reservoir. Serum samples and controls were aliquoted at 100 µL/well according to a template plate map configuration and incubated on a shaker for 1 hour at RT. HRP-conjugated Detection Reagents 2, 5 and 6 were prepared in Blocking Buffer 1 at a 1:5,000 dilution, dispensed at 100 µL/well, and incubated on a shaker for 1 hour at RT. TMB development substrate was added at 100 µL/well and the plate was incubated on a shaker for 15 minutes at RT. Stop Solution was added at 100 µL/well and the plate was read immediately at 450 nm.

Assay Design Parameters

Development of a suitable assay to detect AvPAL-specific antibodies of a particular isotype in a body fluid or tissue sample from a mammal requires identifying an immunoassay and reaction conditions that are sensitive to detect small amounts AvPAL-specific antibodies of a particular isotype in a sample containing AvPAL-specific antibodies of different isotypes, as well as large amounts of non-specific antibodies.

To identify the parameters for assay reagents and format to detect AvPAL-specific antibodies of the IgG isotype, the concentrations for capture and detection reagents, as well as the incubation times and methods to reduce background signal, were determined.

Conditions optimal for assay development included coating with 1 µg/mL PAL, blocking with Blocker Casein PBS (Buffer 1), and then testing samples and controls. Detection of anti-AvPAL antibodies was achieved by using HRP-conjugated species-specific anti-IgG antibodies at 1:5,000 dilution. Additional experiments were performed to evaluate the blocking buffer selection, detection antibody evaluation, and PAL coating condition. The Casein PBS block decreased background as compared to StartingBlock and SuperBlock. Different anti-rabbit antibodies detecting rabbit BP80 positive control in 2% naïve pooled rat, monkey, and human serum were compared. Jackson Labs HRP-conjugated anti-rabbit (Detection Reagent 4) worked best with our BP79, BP79ex, and BP80 positive controls. During sample testing, species-specific HRP conjugated secondary antibodies were used (Detection Reagent 2 for rat and Detection Reagent 6 for monkey/human). One (1) µg/mL PAL was found to be a superior coating concentration for good signal-to-noise ratio (i.e., positive signal versus negatives/background).

Cutpoint Determination

To determine the threshold for a positive result (i.e., cutpoint), the signal distribution for individual naïve sera and a pooled serum lot was tested. The cutpoint was set at a 95% confidence interval to provide a 5% false positive rate.

The standard ELISA protocol described above was used. Twenty naïve samples (10 males and 10 females) were examined for signal distribution in 2% serum (i.e., 50-fold dilution). The average assay signal for multiple naïve individuals was calculated from two replicates in the same manner as unknown samples. The percent difference relative to a pooled lot was calculated. The average and standard deviation were also calculated. To obtain the cutpoint factor, the standard deviation was multiplied by 1.65 (i.e., the student's t-factor for a one-tailed 95% confidence interval).

The cutpoint factor was then added to the absorbance obtained for the pooled sample to obtain the plate cutpoint for each species.

Cutpoints were established by: assaying 20 lots of individual naïve sera per species (e.g., rat, monkey, and human). Two replicates were used for each serum sample to match the samples, which were also analyzed in duplicate. The average signal (A450) for the samples in 2% sera was 0.109 for rat, 0.169 for monkey, and 0.193 for human. This was lower than the normal pooled serum at 0.215 for rat and 0.221 for human, and similar to the signal for pooled serum at 0.163 for monkey. It was also notable that the A450 varied among individual sera from 0.065 to 0.227 in rat, 0.060 to 0.597 in monkey, and 0.083 to 0.401 in human. The CV % between samples was 35.2% in rat, 88.1% in monkey, and 44.9% in human. There was little difference between male and female rat samples, but human female sera had a higher signal than male sera (0.227 versus 0.177). Monkey male sera had a higher signal than female (0.220 vs. 0.163). The cutpoint factors for rat, monkey and human were 0.0635, 0.279, and 0.143, respectively. Based on the determination of the cutpoint factors, the cutpoint for rat, monkey and human were 0.279, 0.442, and 0.364, respectively.

Free Drug Interference

To evaluate the effect of free drug (e.g., rAvPAL-PEG) on the concentration-response relationship, Protein G-purified rabbit anti-rAvPAL-PEG (BP80) was prepared at 10, 100, and 500 ng/mL in naïve serum containing 0, 10, 100, 1,000, and 10,000 ng/mL rAvPAL-PEG. The signal accuracy with and without free drug was compared following the standard ELISA protocol described above.

The signal accuracy using 2% rat and human sera was 80-100% for all QCs, regardless of free drug concentration. For 500 ng/mL BP80 QC in 2% monkey serum, the accuracy fell below 80% at 100 ng/ml rAVPAL-PEG and higher. The low and mid QCs in monkey serum were within +15%.

Matrix Interference

To evaluate the effect of matrix (e.g., serum) on the concentration-response relationship, the accuracy was determined from the signal of samples diluted into increasing amounts of serum. Protein G-purified anti-rAvPAL-PEG rabbit polyclonal antibody (BP80) was prepared at 10, 100, 250, 500, 750, and 1000 ng/mL in naïve-pooled serum from rat, monkey and human at 2%, 5%, and 10%.

The concentration-response relationship of samples diluted in Casein Blocking Buffer versus 2% rat, monkey, and human serum was determined. The 1,000 ng/mL QC was omitted from the analysis due to signal saturation in some samples (OD=4.0). Accuracy in 2% serum was within +25% for all QCs for all three species (90.7-113.0% for rat, 74.5-112.2% for monkey, and 86.0-102.0% for human). Serum increased the signal in 10 ng/mL QC, and attenuated the signal in the 100-750 ng/mL QCs. The accuracy remained within ±25% for 5% and 10% human serum, but was unacceptable for some rat and monkey QCs at these serum concentrations. Therefore, matrix interference is acceptable if rat, monkey, and human sera concentrations remain at 2% in the samples.

Limit of Detection

To determine the lowest amount of analyte that can be detected but not necessarily quantitated (i.e., the limit of detection or LOD, which is the analyte concentration for which the measured mean signal is higher than the cutpoint), a known sample of AvPAL-seropositive rat individual sera positive QC (study 042, animal 371, pooled days 32-59) was prepared at dilutions of 1:3,000, 1:9,000, 1:27,000, and 1:81,000 in 2% rat serum. Using a reference range of anti-AvPAL affinity-purified rabbit IgGs (BP79ex), these dilutions corresponded to approximately 8.0, 3.1, 1.4, and 0.9 ng/mL, respectively. A known sample of AvPAL-seropositive human individual sera positive QC (CUS057 adult male lot 50) was prepared at dilutions of 1:250, 1:750, 1:2,250, 1:6,750, and 1:20,250 in 2% human serum. Using a reference range of BP79ex, these dilutions corresponded to 8.6, 4.2, 2.1, 1.6, and 1.1 ng/mL, respectively. The signal from the dilutions of prepared concentrations was compared to the signal from a 1:50 dilution of naïve pooled serum. Duplicates for each concentration were analyzed and reported as positive or negative versus the rat or human cutpoints. LOD in monkey serum was not calculated at present due to lack of monkey positive control.

The lowest concentration that was consistently above the cutpoint (i.e., 4 out of 5 replicates) determined the LOD. The LOD was associated with 1.4 ng/mL IgG concentration for the rat positive control, and 1.6 ng/mL IgG concentration for the human positive control.

Reagent Stability

To characterize the robustness of preparation and storage stability of the reagents, reagent quality and integrity was observed throughout assay development.

The reagents should be stable over a time period equal to the typical sample preparation, sample handling, and analytical run times using the intended storage temperatures. The quality controls should remain above the pooled serum and the signal proportionality from freshly prepared quality controls must be maintained from the beginning through the end of assay development. No significant changes in control antibody (BP80), PAL coating, Casein block, or detection antibody were observed.

Robustness

To determine its robustness, the capacity of the assay to remain unaffected by small, but deliberate variations in method parameters, and to provide an indication of its reliability during normal usage, was determined. Although not formally tested, most assay parameters and characteristics behaved robustly throughout assay development.

The assay was somewhat sensitive to changes in coating concentration and coating time. The detection antibody seemed to tolerate a range of dilutions (1:2,000-1:10,000). Other assay parameters appeared to be robust.

Selectivity

To determine selectivity (i.e., the ability of the assay to accurately detect the analyte in the presence of different matrix lots), the accuracy of detecting anti-AvPAL control spiked into 5-6 different lots of 2% individual serum at 0, 10, 100, 250, 500, 750, and 1,000 ng/mL was tested.

The 1,000 ng/mL QC was omitted from the analysis due to signal saturation in some samples (A450=4.0). At the 500-750 ng/mL concentrations of anti-PAL BP80, the accuracy was between 77.8 and 105.3%, between 74.3 and 94.2%, and between 82.2 and 102.2% for the rat, monkey and human serum lots. At and below 250 ng/mL BP80, the reproducibility of the signal was even tighter (i.e., all accuracies were within 80-120% and most were very close to 100%). This indicates that lot-to-lot variation will probably not be a serious concern during assay validation.

Specificity

To determine specificity of the assay for anti-AvPAL antibodies and for species cross-reactivity of detection antibodies, rabbit anti-rhASB antibodies (1,000 ng/mL) were tested for cross-reactivity to immobilized PAL. The signals to BP79ex and BP80 rabbit anti-PAL antibodies at high, mid, and low QCs were compared. The ability of excess PAL to compete away positive signal (i.e., confirmatory assay) was determined.

Recombinant human arylsufatase B (rhASB) has no significant homology and identity with AvPAL. The detection response for the positive control was proportional to analyte concentration, and all QCs had mean signals above the purified rabbit anti-rhASB antibodies (BP14 and J3549) and buffer signals. BP14, J3549, and buffer signals all fell below the cutpoints of the three species. Therefore, the assay is specific for the detection of AvPAL antibodies. Rabbit polyclonal antibodies to other PAL variants (BP60ex for *Rhodosporidium toruloides* PAL ((RtPAL); BP64 for *Nostoc punctiforme* PAL (NpPAL)) also demonstrated varying levels of cross-reactivity with AvPAL at equivalent concentrations, but should not be present in samples from pre-clinical and clinical AvPAL studies.

The confirmatory assay also demonstrated specificity for AvPAL antigen in some mammal's samples. Adding excess rAvPAL-PEG (10 µg/mL) deceased the positive control signal by a percentage greater than (cutpoint factor)/(cutpoint). A sample with ≥22.8% decrease in signal in the confirmatory assay was considered a true positive for rat serum. The 042-study rat positive control satisfied this criterion. We also noted seropositive samples from so-called naïve human and monkey samples. A sample with ≥63.1% decrease in signal in the confirmatory assay was considered a true positive for monkey serum. A sample with ≥39.3% decrease in signal in the confirmatory assay was considered a true positive for human serum.

Example 10

Detection of IgM Antibodies Specific to *Anabaena variabilis* Phenylalanine Ammonia-Lyase (AvPAL) in Serum The purpose of this assay development was to create a method to assess the immunogenicity of recombinant *Anabaena variabilis* phenylalanine ammonia-lyase (AvPAL) or variant thereof. In particular, an enzyme-linked immunosorbent assay (ELISA) method was developed to detect IgM antibodies to AvPAL in serum.

Materials

The following therapeutic enzymes were used: AvPAL (unpegylated enzyme) and rAvPAL-PEG (pegylated enzyme) in formulation buffer (10 mM Tris-HCl, 150 mM NaCl, pH 7.5); see Examples 1, 2 and 4 above, as well as U.S. Pat. No. 7,531,341.

The following antibodies were used: BP79: Protein G-purified rabbit anti-rAvPAL-PEG IgG (Positive Control) in 1×DPBS, pH 7.0-7.2; BP79ex: affinity-purified rabbit anti-rAvPAL-PEG IgG (Positive Control) in 1×DPBS, pH 7.0-7.2; BP80: Protein G-purified rabbit anti-rAvPAL-PEG IgG (Positive Control) in 1×DPBS, pH 7.0-7.2; BP14: rabbit anti-recombinant human arylsulfatase B (rhASB) purified IgG; rat quality control (QC) at high, mid and low dilutions (HP=1:50, MP=1:150, LP=1:450) of anti-AvPAL IgM in neat rat serum (unpurified individual rat sera confirmed positive against AvPAL from Bioreclamation, Inc., Cat No. RATBREC.34982F and RATBREC.26135M); monkey quality control (QC) at high, mid and low dilutions (HP=1:50, MP=1:150, LP=1:450) of anti-AvPAL IgM in neat monkey serum (unpurified individual monkey sera confirmed positive against AvPAL from Bioreclamation, Inc., Cat No. CYNSRM.28918F); human quality control (QC) at high, mid and low dilutions (HP=1:50, MP=1:150, LP=1:450) of anti-AvPAL IgM in neat human serum (unpurified individual human sera confirmed positive against AvPAL from The Binding Site, Cat No. CUS057 lot 3 and Bioreclamation, Inc., Cat No. HUMSRM.BRH73661); detection reagent 2: HRP-conjugated goat anti-rat IgM Fc (Jackson ImmunoResearch, Cat. No. 112-036-075); detection reagent 4: HRP-conjugated goat anti-rabbit IgG (H+L) (Jackson ImmunoResearch, Cat. No. 111-036-045); detection reagent 5: HRP-conjugated donkey anti-human IgM Fc (Jackson ImmunoResearch, Cat. No. 709-036-064).

The following matrices were used: pooled and individual naïve-normal Sprague Dawley rat serum (Bioreclamation, Inc., Cat No. RATSRM.RATBREC); pooled and individual naïve-normal Cynomolgous monkey serum, Mauritius origin (Bioreclamation, Inc., Cat No. CYNSRM.CYNBREC); and pooled and individual naïve-normal human serum (Bioreclamation, Inc., Cat No. HUMSRM; The Binding Site, Cat No. CUS057).

The following ELISA reagents were used: coating buffer: 1×DPBS (Mediatech, Fisher Cat No. MT-21-031-CV); wash buffer 1:1×DPBS/0.1% Tween-20/0.05% Proclin 300; wash buffer 2:1×DPBS/0.25% Tween-20/0.05% Proclin 300; bovine serum albumin (BSA), fraction V, Omnipure (EMD, VWR Cat No. 2930); blocking buffer 1: Blocker Casein in PBS (Pierce, Cat No. 37528); blocking buffer 2: Blocker Casein in TBS (Pierce, Cat No. 37532); blocking buffer 3: SuperBlock T20 TBS (Pierce, Cat No. 37536); blocking buffer 4: StartingBlock T20 PBS (Pierce, Cat No. 37539); development reagent: TMB Peroxidase EIA Substrate Kit, 250 mL (BioRad, Cat No. 172-1066); and stop solution: 2 N $H_2SO_4$.

The following chemicals were used: de-ionized water (MilliQ filtered); Dulbecco's phosphate buffered saline (DPBS), 1× (Mediatech, Fisher Cat No. MT-21-031-CV); Dulbecco's phosphate buffered saline (DPBS), 10× (Mediatech, Fisher Cat No. MT-20-031-CV); sulfuric acid ($H_2SO_4$), 11 N (VWR, Cat No. VW3481-1); Tween-20 (Acros Organics, VWR Cat No. 233360010); and Proclin 300 (Supelco, Cat No. 4-8126).

The following plasticware and other materials were used: recombinant human arylsulfatase B (rhASB) in 1×DPBS; assay dilution block: 96-well, polypropylene, V-bottom, non-sterile, 2 mL well (VWR, Cat No. 40002-012); ELISA plate: 96-well, Maxisorp, flat bottom "F" (Nalge/Nunc International, VWR Cat No. 12-565-135); microcentrifuge tubes, 1.5 mL (USA Scientific, VWR Cat No. 1615-550); microcentrifuge tubes, 2.0 mL (Eppendorf, VWR Cat No. 62111-754); microplate adhesive film (USA Scientific, Cat No. 2920-0000); pipetman tips: 20 µL, 250 µL, and 1000 µL (Rainin Instruments, Cat Nos. GPS-L1000, GPS-L250, GPS-L10); reagent reservoir, 50 mL capacity (Corning, VWR Cat No. 82026-350); and serological pipettes, 10 mL and 25 mL (VWR, Cat No. 13-678-11D and 13-678-11E)

The following equipment and software were used: Elx405 Select Plate Washer (Bio-Tek); multichannel pipetman, 12-well, LTS 20-200 µL (Rainin Instruments); multichannel pipetman, 12-well, LTS 100-1200 µL (Rainin Instruments); pipet-aid, multi-speed, Drummond (VWR, Cat No. 13-681-15E); SOFTmax Pro v 3.0 (Molecular Devices); SpectraMax PLUS Microplate Spectrophotometer (Molecular Devices); timer, three channel alarm (VWR, Cat No. 62344-600); and titer plate shaker (Barnstead/Lab-Line Instruments).

ELISA Protocol

Preparation of Samples:

Serum samples for screening were initially diluted 1:50. For suspected highly positive samples, dilutions were higher. Screened samples were compared to the species-specific assay cutpoint. For positive samples above the cutpoint, the confirmation step was performed to determine whether the sample was a true positive (i.e., observed signal loss due to spiked AvPAL in sample).

Preparation of Positive Controls:

Rabbit positive controls were prepared in Blocking Buffer 1 at 10, 100, and 500 ng/mL BP80. BP80 is a Protein G-purified rabbit polyclonal antibody against rAvPAL-PEG. An analogous lot of BP79 and BP79ex (affinity-purified anti-AvPAL antibodies from BP79) were also used in specialized applications. These rabbit antibodies were used as surrogate QCs in some experiments due to scarcity of supply of anti-AvPAL IgM. The detection reagent used for these controls was Detection Reagent 4, an HRP-conjugated goat anti-rabbit-IgG diluted to 1:5,000 in Blocking Buffer 1. Rat IgM positive controls were prepared in Blocking Buffer 1 at 1:50 dilution (approximately 2.1 ng/mL IgM). The rat positive controls were RATBREC.34982F and RATBREC.26135M, individual rat serum lots seropositive against AvPAL. The detection reagent used for these controls was Detection Reagent 2, an HRP-conjugated goat anti-rat-IgM diluted to 1:5,000 in Blocking Buffer 1. Monkey IgM positive controls were prepared in Blocking Buffer 1 at 1:150 dilution (approximately 2.8 ng/mL IgM). The monkey positive control was CYNSRM.28918F, an individual monkey serum lot seropositive against AvPAL. The detection reagent used for this control was Detection Reagent 5, an HRP-conjugated donkey anti-human-IgM diluted to 1:5,000 in Blocking Buffer 1. Human IgM positive controls were prepared in Blocking Buffer 1 at 1:150 dilution (approximately 2.8 ng/mL IgM). The human/monkey positive controls were CUS057 lot 3 and HUMSRM.BRH73661, individual human serum lots seropositive against AvPAL. The detection reagent used for these controls was Detection Reagent 5, an HRP-conjugated donkey anti-human-IgM diluted to 1:5,000 in Blocking Buffer 1.

ELISA Procedure:

AvPAL was prepared at 1 µg/mL in Coating Buffer (1×DPBS), dispensed at 100 µL per well into the ELISA plate (Nalge/Nunc MaxiSorp surface), and incubated 12 to 20 hours (overnight) at 4° C. Blocking Buffer 1 (Blocker Casein PBS) was added at 300 µL/well and incubated on a shaker for 1 hour at room temperature (RT). Blocking Buffer 1 was removed by pouring into a waste reservoir. Serum samples and controls were aliquoted at 100 µL/well according to a template plate map configuration and incubated on a shaker for 1 hour at RT. HRP-conjugated Detection Reagents were prepared in Blocking Buffer 1 at a 1:5,000 dilution, dispensed at 100 µL/well, and incubated on a shaker for 1 hour at RT. TMB development substrate was added at 100 µL/well and the plate was incubated on a shaker for 15 minutes at RT. Stop Solution was added at 100 µL/well and the plate was read immediately at 450 nm.

Assay Design Parameters

To identify the parameters for assay reagents and format to identify AvPAL-specific antibodies of the IgM isotype, the concentrations for capture and detection reagents, as well as the incubation times and methods to reduce background, were determined.

Conditions optimal for assay development included coating with 1 µg/mL AvPAL, blocking with Blocker Casein PBS (Buffer 1), and then testing samples and controls. Detection of anti-AvPAL antibodies was achieved by using HRP-conjugated species-specific anti-IgM antibodies at 1:5,000 dilution. Casein PBS was the superior blocker to decrease background when compared to other Pierce blockers.

Cutpoint Determination

To determine the threshold for a positive result (i.e., cutpoint), the signal distribution for individual naïve sera and a pooled serum lot was tested. The cutpoint was set at a 95% confidence interval to provide a 5% false positive rate.

Signal distribution in 2% serum was tested for 20 naïve rat, monkey, and human serum samples (approximately 50% male and 50% female). The average assay signal for multiple naïve individuals was calculated from two replicates in the same manner as unknown samples. The percent difference relative to a pooled lot was calculated. The average and standard deviation were also calculated. To obtain the cutpoint factor, the standard deviation was multiplied by 1.65 (i.e., the student's t-factor for a one-tailed 95% confidence interval). The cutpoint factor was then added to the pool average to obtain the plate cutpoint for each species.

Cutpoints were established by assaying 10-20 lots of individual naïve sera per species (i.e., rat, monkey, and human). Two replicates were used for each serum sample to match the samples, which were also analyzed in duplicate. The average signal (A450) for the samples in 2% sera was 0.385 for rat, 0.341 for monkey, and 0.167 for human. The naïve pooled serum was 0.314 for rat, 0.187 for monkey, and 0.300 for human. It was also notable that the A450 varies among individual sera from 0.248 to 0.596 in rat, 0.152 to 0.627 in monkey, and 0.090 to 0.321 in human. The CV % between samples was 27.2% in rat, 50.6% in monkey, and 37.2% in human. There was little difference between male and female rat samples, but monkey and human female sera had higher signals than male sera (0.411 versus 0.262 and 0.204 versus 0.130, respectively). The cutpoint factors for rat, monkey, and human were 0.0635, 0.285, and 0.102, respectively. Based on the determination of the cutpoint factors, the cutpoints for rat, monkey, and human were 0.475, 0.472, and 0.402, respectively. The number of false positives of individual lots for rat, monkey and human were 3/19 (16%), 4/16 (25%), and 0/20 (0%), respectively. Since the desired rate of false positives in the assay is 5%, the IgM ELISA for rat and monkey may over-estimate the number of positive samples above the cutpoint. However, the confirmation step in the assay is designed to identify true positives versus samples with unusually high background or nonspecific IgM binding.

Free Drug Interference

The effect of free drug on the concentration-response relationship was evaluated. Seropositive QCs against AvPAL from each species were prepared at low (LP=1:450), mid (MP=1:150), and high (HP=1:50) QC dilutions in naïve serum containing 0, 10, 100, 1,000, and 10,000 ng/mL AvPAL or rAvPAL-PEG. The signal accuracies with and without free drug were compared.

The accuracy results for the different rAvPAL-PEG drug concentrations showed that the accuracy in 2% rat, monkey, and human sera was 80-110% for all QCs, regardless of free drug concentration. The QCs that had signals above the cutpoints in buffer did not fall below the cutpoints in the presence of drug. In general, the LP had better accuracies than MP or HP. The accuracy results for the different unpegylated AvPAL concentrations showed that, similar to the confirmatory data, the accuracy for most of the QCs at HP and LP dilutions decreased with increasing AvPAL spike.

In many cases, the reduction in accuracy was greater with unpegylated AvPAL spike versus rAvPAL-PEG Matrix Interference To evaluate the effect of matrix (e.g., serum) on the concentration-response relationship, the effect of matrix on accuracy from the signal of QC samples diluted into increasing amounts of serum was determined. Seropositive QCs against AvPAL from each species were prepared at low, mid, and high QC dilutions (1:540, 1:180, and 1:60) in naïve pooled serum from rat, monkey and human each at 1%, 2%, and 10%.

The accuracy of the QCs at the different serum concentrations showed that serum served to increase the signal in most QCs of each species, but attenuated the signal at the 1:60 QC in human. The accuracy remained within ±25% for the mid and low dilutions in 1%, 2%, and 10% human serum, but was unacceptable for most rat and monkey QCs. Since the standard 2% naïve pooled serum background for all three species was approximately 0.3 (A450), the mean signal seemed to be additive with QCs in rat and monkey (i.e., the QC signal in 2% serum was approximately equal to the QC signal in buffer plus 2% serum background signal). Therefore, when the 2% serum background signal was subtracted from the rat and monkey QCs, most of the QCs were within ±25% accuracy. But the low absolute signal strength of the rat and monkey QCs (~0.8 A450 at HP 1:50 dilution) may have contributed to the significant matrix interference. This problem is probably not an attribute of the assay itself, because the human QCs in naïve matrix passed properly.

Relative Limit of Detection (LOD)

The approximate lowest amount of analyte that can be detected, but not necessarily quantitated, was determined. The relative limit of detection or LOD is the analyte concentration for which the measured mean signal is higher than the cutpoint in 4 out of 5 replicates. Known samples of AvPAL-seropositive rat (RATBREC.34982F), monkey (CYNSRM.28918F), and human (CUS057 adult female lot 3) individual sera positive QCs were prepared at dilutions of 1:50, 1:150, 1:450, and 1:1,350 in 2% naïve pooled serum. Using a 50-0 ng/mL reference range of AvPAL-affinity-purified rabbit IgGs (BP79ex), these dilutions corresponded to approximations of specific anti-AvPAL IgMs. The signal from the dilutions of prepared concentrations was compared to the signal from a 1:50 dilution of naïve pooled serum. Duplicates for each concentration were analyzed and reported as positive or negative versus the rat, monkey, or human cutpoints.

To estimate the relative LOD, we compared the signal from true positive rat, monkey, and human individual serum lots to a reference curve of BP79ex anti-rAvPAL-PEG affinity purified rabbit IgGs of known concentration. We therefore made three assumptions: (1) a comparable concentration of rat, monkey, and human anti-AvPAL IgMs bound similarly to immobilized AvPAL as the anti-rAvPAL-PEG rabbit IgG reference, (2) said antibodies are similarly detected with species-and-chain-specific HRP-conjugated secondaries, and (3) the presence of ≤2% naïve serum did not greatly affect the QC signals versus BP79ex. These assumptions allowed for a ballpark estimate of the relative LOD. The lowest concentration that is consistently above the cutpoint (4 out of 5 replicates) determines the relative LOD. A known sample of AvPAL-seropositive rat individual sera QC (RATBREC.34982F) was prepared at dilutions of 1:50, 1:150, 1:450, and 1:1,350 in 2% rat serum. Using a reference range of AvPAL-affinity-purified rabbit IgGs (BP79ex), these dilutions corresponded to approximately 2.1, 0.6, <0.6, and <<0.6 ng/mL, respectively. A known sample of AvPAL-seropositive monkey individual sera QC (CYNSRM.28918F) was prepared at dilutions of 1:50, 1:150, 1:450, and 1:1,350 in 2% monkey serum. Using a reference range of AvPAL-affinity-purified rabbit IgGs (BP79ex), these dilutions corresponded to approximately 5.0, 2.6, 0.9, and 0.2 ng/mL, respectively. A known sample of AvPAL-seropositive human individual sera QC (CUS057 adult female lot 3) was prepared at dilutions of 1:50, 1:150, 1:450, and 1:1,350 in 2% human serum. Using a reference range of BP79ex, these dilutions corresponded to 5.9, 2.8, 0.95, and <0.95 ng/mL, respectively. The LOD was associated with 2.1 ng/mL IgM concentration for rat positive control, 2.6 ng/mL IgM concentration for monkey positive control, and 2.8 ng/mL IgM concentration for human positive control. The true LODs may be higher or lower than 2-3 ng/mL, but cannot be determined without purified, well-characterized anti-AvPAL IgM antibodies from each of the three species.

Reagent Stability

To characterize the robustness of preparation and storage stability of the reagents, reagent quality and integrity was observed throughout assay development.

This assay parameter will be formally tested during validation. The reagents should be stable over a time period equal to the typical sample preparation, sample handling, and analytical run times using the intended storage temperatures. The quality controls should remain above the pooled serum and the signal proportionality from freshly prepared quality controls must be maintained from the beginning through the end of assay development. No significant changes in control antibody, AvPAL coating, Casein Block, or detection antibody were observed.

Robustness

To determine its robustness, the capacity of the assay to remain unaffected by small, but deliberate variations in method parameters, and to provide an indication of its reliability during normal usage, was determined. Although not formally tested, most assay parameters and characteristics behaved robustly throughout assay development.

The assay was somewhat sensitive to changes in coating concentration and coating time. The detection antibody seemed to tolerate a range of dilutions (1:2,000-1:10,000). Other assay parameters appear to be robust.

Selectivity

The selectivity (i.e., the ability of the assay to accurately detect analyte in the presence of different matrix lots) was determined by testing the accuracy of detecting anti-AvPAL QCs spiked into at least 3 different lots of 2% individual serum at low (LP=1:450), mid (MP=1:150), and high (HP=1:50) QC dilutions.

In general, the HP and MP QCs had better accuracies than LP. For the lots of rat serum, the accuracy varied from 68.7-119.4%, with all but one QC within ±25%. For the lots of monkey serum, the accuracy varied from 64.5-93.2%, with all but two QCs within ±25%. For the lots of human serum, the accuracy varied from 77.1-110.8%, with all QCs within ±25%. This indicates that lot-to-lot variation will probably not be a serious concern during assay validation.

Specificity

To determine the specificity of the assay for anti-AvPAL IgMs versus species cross-reactivity and foreign antibodies/antigens, anti-rhASB and anti-AvPAL QCs were tested for cross-reactivity to immobilized AvPAL and recombinant human ASB (rhASB). The ability of excess AvPAL to compete away positive signal (i.e., confirmatory assay) was determined.

Recombinant human arylsulfatase B (rhASB) has no significant homology and identity with AvPAL. The determination of specificity showed that the species-specific anti-AvPAL IgM QCs had a concentration-dependent A450 response, and the signal detected with anti-IgM-HRP was always higher than the anti-IgG-HRP signal under the same conditions. Therefore, the QCs are specific to anti-AvPAL IgMs versus IgGs. The anti-AvPAL IgM QCs preferentially bound to immobilized AvPAL versus immobilized rhASB. The anti-AvPAL QC signals were above the species cutpoints, and the anti-rhASB negative control was below the cutpoint. Therefore, the assay is specific for the detection of AvPAL antibodies. The rhASB and AvPAL coated properly because they were readily detectable by specific rabbit IgGs with no observed cross-reactivity (i.e., BP14 against rhASB and BP79ex against AvPAL). Therefore, the anti-AvPAL IgM QCs are specific for AvPAL, and the detected IgM signal is not heavily contaminated with IgG.

The confirmatory assay also demonstrated specificity for AvPAL antigen. By adding excess AvPAL (0.1 mg/mL), the positive control signal was decreased by a percentage greater than (cutpoint factor)/(cutpoint). A sample with ≥34.0% decrease in signal in the confirmatory assay was considered a true positive for rat serum. A sample with ≥60.4% decrease in signal in the confirmatory assay was considered a true positive for monkey serum. A sample with ≥25.4% decrease in signal in the confirmatory assay was considered a true positive for human serum. We observed true seropositives from several so-called naïve individual samples. Such samples will be omitted from future cutpoint determinations during assay validation.

Example 11

Detection of Neutralizing Antibodies Specific to *Anabaena variabilis* Phenylalanine Ammonia-Lyase (AvPAL) in Serum The purpose of this assay development was to create a method to detect the neutralizing antibodies to recombinant *Anabaena variabilis* phenylalanine ammonia-lyase (AvPAL) or variant thereof. In particular, an enzyme activity assay method was developed to detect antibodies in serum that are able to inhibit the AvPAL enzymatic activity.

Materials

The following materials were used: rAvPAL-PEG (pegylated enzyme) (1.4 mg/mL); see Examples 1, 2 and 4 above, as well as U.S. Pat. No. 7,531,341.

The following antibodies were used: KK84: positive control antibody (Cynomolgous anti-rAvPAL-PEG, affinity purified); and G192: (Sheep anti-recombinant human arylsulfatase B (rhASB) antiserum, affinity purified). KK84 was generated by immunizing Cynomolgous monkeys with rAvPAL-PEG with adjuvant. Sera from the immunized Cynomolgous monkeys were collected and purified for anti-AvPAL antibodies; IgG from three Cynomolgous monkeys were tested, and one was positive.

The following matrices were used: normal Cynomolgous monkey serum, Mauritius origin (Bioreclamation, Inc., lot#16895A); and normal human serum (Bioreclamation, Inc., lot#22234).

The following chemicals were used: Trizma (Sigma T1503-500G); 6N HCL (J. T. Baker 5619-02); BSA Fraction V (Sigma A3059-500G); phenylalanine (Sigma P-5482); sodium azide (Sigma 58032-25G); sodium chloride (VWR BDH0286-500G); Tween 80 (EM Science OmniPur 9490); and sulfuric acid ($H_2SO_4$) 12N (VWR Cat No. VW3481-1).

The following plasticware and other materials were used: UV plate: 96-well flat bottom, Costar 3635; microcentrifuge tubes, 1.5 mL (USA Scientific, VWR Cat No. 1615-550); microcentrifuge tubes, 2.0 mL (Eppendorf, VWR Cat No. 62111-754); microplate adhesive film (USA Scientific, Cat No. 2920-0000); pipetman tips: 20 µL, 250 µL, and 1000 µL (Rainin Instruments, Cat Nos. GPS-L1000, GPS-L250, GPS-L10); reagent reservoir, 50 mL capacity (Corning, VWR Cat No. 82026-350); and serological pipettes, 10 mL and 25 mL (VWR, Cat No. 13-678-11D and 13-678-11E).

The following equipment and software were used: Jitterbug incubator/shaker; multichannel pipetman, 12-well, LTS 20-200 µL (Rainin Instruments); multichannel pipetman, 12-well, LTS 100-1200 µL (Rainin Instruments); pipet-aid, multi-speed, Drummond (VWR, Cat No. 13-681-15E); SOFTmax Pro v 5.0 (Molecular Devices); SpectraMax M2E Microplate Spectrophotometer (Molecular Devices); timer, three channel alarm (VWR, Cat No. 62344-600); and pipetman LTS-20, LTS-100, LTS-200, and LTS-1000 (Rainin Instruments).

The following buffers were used: dilution buffer: 1.6 mM Tris-base, 8.4 mM Tris-HCl, 140 mM NaCl, 2 mg/mL BSA, 1 mM Phe, 0.05% Tween 80 and 0.01% sodium azide, pH 7.3; and substrate buffer: 0.1 M Tris, pH 8.5, 22.5 mM L-Phe.

Activity Assay Protocol

Preparation of rAvPAL-PEG Working Solution:

The 1.4 mg/mL rAvPAL-PEG stock solution was diluted 1:140 in Dilution Buffer to give a working solution at 10 µg/mL.

Preparation of Samples:

A baseline sample, test samples and a positive neutralizing antibody control were prepared in cluster tubes as follows. For the baseline sample, 75 µL of rAvPAL-PEG was combined with 7.5 µL of pooled cyno serum, then 67.5 µL of Dilution Buffer was added to test sample for a final volume of 150 µL. For the test samples, 75 µL of rAvPAL-PEG was combined with 7.5 µL of serum, then 67.5 µL of Dilution Buffer was added to test sample for a final volume of 150 µL. For the positive neutralizing antibody control, 75 µL of rAVPAL-PEG was combined with 7.5 µL of pooled cyno serum, then 29 µL of KK84 positive control antibody (520 µg/mL stock) was added. 38.5 µL of Dilution Buffer was added for final volume of 150 µL.

Activity Assay:

100 µL of mixed samples were transferred to a Costar UV flat bottom plate. Rows 1, 5 and 9 on the plate were used to run up to 22 test samples, baseline sample and positive control samples. 200 µL of Substrate Buffer was added to rows 2, 3, 4, 6, 7, 8, 10, 11 and 12. The plate was preincubated for 30 minutes at 30° C. Following preincubation, the activity assay was started by transferring in triplicate, 20 µL of test samples, baseline sample and positive control sample from row 1 to substrate containing rows 2, 3 and 4; this transfer step was repeated from row 5 to substrate containing rows 6, 7 and 8, and from row 9 to substrate containing rows 10, 11 and 12. Reactions containing mixed samples and substrate were incubated for an additional 30 minutes at 30° C., then the reactions were stopped by adding 50 µL of 2N $H_2SO_4$. In end point mode, the plate was read after 30 minutes using 290 nm absorbance. The plate cutpoint was determined by subtracting the cutpoint factor (0.048 for cyno serum and 0.065 for human serum) from the baseline sample. A test sample was scored as positive for neutralizing anti-rAvPAL-PEG antibody if the OD value was found to be below plate cutpoint.

Assay Design Parameters

Development of a suitable assay to detect neutralizing AvPAL-specific antibodies in a body fluid or tissue sample from a mammal requires identifying an enzyme assay (i.e., phenylalanine converting activity) and reaction conditions that are sensitive to detect small amounts of neutralizing AvPAL-specific antibodies in a sample containing large amounts of non-neutralizing AvPAL-specific antibodies and non-specific antibodies. In addition, the enzyme assay has to take into consideration the baseline level of AvPAL activity, which can easily be affected by active AvPAL enzyme in the serum or plasma samples, thereby causing potential false negative results.

To identify the parameters for assay reagents and format to detect neutralizing AvPAL-specific antibodies, the reagent concentration, incubation buffers, and controls for the activity assay, as well as the performance characteristics of the kinetic method and endpoint method, were determined.

The optimal concentrations of rAvPAL-PEG were established by examining a range of concentrations via kinetic and endpoint modes. Serial 2-fold dilutions of rAvPAL-PEG from 50 μg/mL to 3 ng/mL in dilution buffer were prepared, and the concentration-response relationship was examined in the activity assay. The substrate-enzyme concentration response relationship was measured using both endpoint and kinetic measurements in 2% matrix and buffer. Measurements at 290 nm (trans-cinnamic acid absorbance) were taken every 30 seconds using the kinetic read mode, and the Vmax (mOD/min) was determined. For endpoint analysis, the reactions were stopped at 20, 30, and 60 minutes, the OD at 290 nm was measured, and results were plotted on SoftMaxPro using a 4-parameter fit.

Increasing the rAvPAL-PEG concentration in the presence of excess Phe substrate resulted in increased trans-cinnamic acid using the kinetic read. The concentration of rAvPAL-PEG spanned 50 μg/mL to 3 ng/mL and provided good curve fit and back-calculated accuracy to approximately 1 μg/mL. This dose response information can be used to estimate the optimal amount of rAvPAL-PEG to use to assess the presence of neutralizing antibodies. For the endpoint assay, the same reaction was performed and at the end the reaction was stopped by addition of 50 μL of 2N $H_2SO_4$ and read at 290 nm after 20 minutes or 60 minutes. In both of the kinetic and endpoint assays, the interference from 2% rat and 2% cyno serum was minimal when compared to reaction buffer. Both the endpoint and kinetic assays gave similar concentration response curves. The kinetic assay measures the rate of change of the trans-cinnamic acid production and is more prone to deviations. The endpoint assay measures the trans-cinnamic acid production after a finite time point and is less susceptible to variability. Evaluation of both endpoint and kinetic assays showed that a rAvPAL-PEG concentration of between 5-10 μg/mL would give an OD signal that was robust yet could be inhibited by an antibody control. Further tests established that 5 μg/mL is an appropriate amount of rAvPAL-PEG to use for the activity assay. The endpoint assay is preferred over the kinetic assay because the latter is more variable. A 30 minute endpoint using 5% serum with rAvPAL-PEG at 5 μg/mL was determined to be a feasible approach for the activity assay.

Baseline Activity in Normal Serum

Naïve sera were tested to establish a 95% confidence interval using the endpoint method with increasing concentrations of rAvPAL-PEG.

Pooled cyno serum was compared to 20 naïve individual samples (10 male and 10 female) for signal variability. Similarly, pooled human serum was compared test 10 individual lots of naïve human serum. 5% serum (1:20 dilution) was used in the activity assay. Following 30 minutes of incubation, enzyme activity was neutralized with 50 μL 2N $H_2SO_4$ and read via endpoint measurement. Each sample was examined using a range of rAvPAL-PEG concentrations (312.5-20,000 ng/mL), and the average signal, standard deviation, cutpoint factor and plate cutpoint using 95% confidence interval were determined.

The mean signals for cyno serum samples using 2.5, 5, and 10 μg/mL rAvPAL-PEG were 0.307, 0.436, and 0.666, respectively. The variability was minimal (CV % less than 10%) within conditions and between individuals. By applying a 95% confidence interval to the data set, the plate cutpoint was determined. The cutpoint factor is calculated as [(95% CI)=1.645×standard deviation]. The plate cutpoint is calculated as [pooled normal cyno or human serum sample OD minus the cutpoint factor]. A sample is deemed as having positive neutralizing anti-rAvPAL-PEG antibody activity if the OD is below the plate cutpoint. For 5% cyno serum, the cutpoint factor using 5 μg/mL rAvPAL-PEG was 0.048 and the plate cutpoint was 0.431. The cutpoint factor accounted for an 11% reduction in signal (0.048÷0.431× 100=11%). Although slightly more variable (CV % of 4.7%-10.3%), a 95% confidence interval and plate cutpoint were calculated for 5% human serum using 5 μg/mL rAvPAL-PEG. The cutpoint factor was 0.065 and the plate cutpoint was 0.405. The cutpoint corresponded to a modest decrease in signal that equated to approximately 10%-20% reduction that could be relied upon to determine antibody mediated neutralization of rAvPAL-PEG.

Specificity

The specificity of antibody mediated neutralization of rAvPAL-PEG activity was established. The response to 0, 10, 100, and 300 μg/mL neutralizing rAvPAL-PEG antibody (KK84, affinity-purified cyno anti-rAvPAL-PEG antibody) was compared to 300 μg/mL non-neutralizing rhASB antibody (G192), using 2.5, 5, and 10 μg/mL of rAvPAL-PEG in the endpoint assay in both human and cyno serum.

Increasing amounts of anti-rAvPAL-PEG antibody (KK84) reduced the activity of rAvPAL-PEG. The 100 and 300 μg/mL concentrations of KK84 worked best. The reduction was more marked in human serum than in cyno serum. The 300 μg/mL anti-rhASB antibody (G192) did not significantly reduce enzymatic activity. These results demonstrate a concentration response relationship and specific nature of the antibody-enzyme interaction.

Sensitivity/Limit of Detection

The lowest concentration of neutralizing antibody in a sample which can be detected (i.e., decrease rAvPAL-PEG activity) was determined.

Positive control antibodies were prepared in cyno and human serum in a dilution series, and the lowest concentration that gave a signal below the assay cutpoint was identified. 2.5, 5, and 10 μg/mL rAvPAL-PEG was tested in combination with 0, 10, 100, and 300 μg/mL positive control rAvPAL-PEG antibody (KK84).

The KK84 antibody at 10 μg/mL reduced the 2.5, 5 and 10 μg/mL rAvPAL-PEG signal by less than 10% in both cyno and human serum. This reduction was to a level that was not less than the cutpoint and therefore unlikely to be consistently positive. However, the KK84 antibody at 100 μg/mL reduced the 2.5, 5, and 10 μg/mL rAvPAL-PEG signal by 12%-21% in both cyno and human serum, and at 300 μg/mL up to 32% reduction in cyno serum and up to 38% in human serum, depending on the level of rAvPAL-PEG. Therefore, the limit of detection was approximately 100 μg/mL using the KK84 antibody. The 5 μg/mL concentration of rAvPAL-PEG seemed most responsive using either cyno or human serum. The limit of detection is an approximation of the sensitivity of the assay and is dependent on the specific character of the positive control antibody used in the assay (i.e., affinity and epitope). Several anti-rAvPAL-PEG antibodies were examined, but only the KK84 antibody had measurable neutralizing activity response. The nature of the rAvPAL-PEG enzyme (i.e., pegylated AvPAL tetramer) supports the notion that activity neutralization via antibody interaction may be difficult to measure. A neutralizing antibody may need to block or sterically modify the catalytic pocket to achieve the desired effect.

Interference by Free Drug

The effect of free drug on the antibody-activity response relationship was evaluated. The samples obtained for antibody analysis are typically acquired several days post injection, and immediately before the next injection. Prior pharmacokinetic analysis has demonstrated that the half-life of rAvPAL-PEG is several days (~5 days). Therefore, measurable concentrations of free drug may be present and cause interference.

Increasing amounts of rAvPAL-PEG (0, 1, 10, and 100 µg/mL) were added into the serum along with 0, 1, 10, and 100 µg/mL positive control antibody (KK84), and the drug-antibody mixtures were pre-incubated for 30 minutes. The level of interference at different amounts of free drug using 5 µg/mL rAvPAL-PEG in the activity assay was determined.

The neutralizing antibody activity assay was modestly sensitive to free drug in serum. Addition of 100 µg/mL of rAvPAL-PEG eliminated the neutralizing effect of the 10 and 100 µg/mL KK84 positive control antibody.

Interference by Matrix

The effect of the matrix (i.e., serum) on the antibody-activity response relationship was evaluated by increasing the amounts of cyno serum on the activity assay. Specifically, the level of inhibition obtained with the KK84 control antibody on rAvPAL-PEG in buffer, 2.5%, 5%, 10%, 20% cyno serum was measured.

Increasing serum concentrations had a minimal effect on the activity assay at 2% serum as compared to buffer. At 5% serum, modest matrix interference was observed, and at 10% serum, there was significant matrix interference. 2.5% and 5% serum did not prevent antibody neutralization obtained with KK84 at 100 µg/ml, however, 10% and 20% cyno serum caused enough matrix interference to mask the neutralization effect of KK84. Thus, dilution of a test sample by 1:20 (5%) is recommended.

Precision

The intra-assay and inter-assay variability of the activity neutralizing antibody assay over a two day period was examined. Replicate 5 µg/mL rAvPAL-PEG samples in 5% cyno serum were prepared and enzyme activity was measured in the absence and presence of KK84 (100 µg/mL). The intra-day variability and inter-day variability as measured by CV %.

The intra-assay and inter-assay replicates showed less than 5% variability as measured by CV % when tested by one analyst over two days. The KK84 was able to inhibit to below the cutpoint on both days.

Robustness

The capacity of the assay to remain unaffected by small, but deliberate variations in method parameters was determined to provide an indication of its reliability during normal usage. The reduction in activity when using KK84 at 80, 100, and 120 µg/mL was examined. Pre-incubation times and assay incubation times at 24, 30, 36 minutes, which represent 80%, 100%, and 120% of the optimized times, were examined. The stability of reagents used in the activity assay was evaluated.

The KK84 antibody, when used at 100 µg/mL, was able to inhibit the reaction to below cutpoint at increased incubation times up to 36 minutes. It is expected that decreased incubation times within 10% of the 30 minute time may not affect the assay. The substrate and dilution solutions have been used after preparation and storage at 4° C. for up to 6 months without significant loss in activity. The KK84 antibody is typically stored at 4° C. after being thawed; after storage for 1 month, the KK84 antibody was able to inhibit activity to below cutpoint and compared similarly to freshly thawed material.

Selectivity

The variability between individual matrices using pooled and individual serum samples was examined. Pooled and individual serum samples with KK84 control and rAvPAL-PEG at 5 µg/ml in 5% serum was tested in the endpoint assay.

KK84 was able to neutralize activity of 5 µg/mL rAvPAL-PEG to below cutpoint for pooled and individual serum samples. The percent reduction ranged from 14-18%. Thus, the activity assay demonstrates selectivity.

Example 12

Detection of IgG Antibodies Specific to Polyethylene Glycol (PEG) in Serum

An assay was developed to detect the presence of antibodies specific for polyethylene glycol (PEG) or derivatives thereof. In particular, an enzyme-linked immunosorbent assay (ELISA) method was developed to detect IgG antibodies to PEG in serum.

Materials

The following forms of PEG were used: 20 kDa methoxy PEG (NOF Corporation, Cat No. ME-200HS) inactivated by dissolution in TBS buffer, pH 7.5, and reconstituted to 2 mg/mL in TBS buffer, pH 7.5; and 6 kDa hydroxy PEG (Fluka, Cat No. 53770) (1.8 mg/mL in 0.1 M Tris-HCl, pH 8.0, 30% PEG 6000).

The following antibodies were used: rabbit anti-PEG IgG (Epitomics); and detection reagent: HRP-conjugated goat anti-human IgG (H+L) (KPL, Cat No. 474-1006).

The following matrices were used: Human serum (pooled); and individual human serum (Bioreclamation, Inc.).

The following ELISA reagents were used: coating buffer and wash buffer: 1×DPBS (Cellgro, Cat No. 21-031-CV); blocking buffer: Blocker Casein in PBS (Thermo, Cat No. 37528); development reagent: TMB Peroxidase EIA Substrate Kit, 250 mL (BioRad, Cat No. 172-1066); and stop solution: 2 N $H_2SO_4$.

The following chemicals were used: de-ionized water (MilliQ filtered); Dulbecco's phosphate buffered saline (DPBS), 1× (Cellgro, Cat No. 21-031-CV); sulfuric acid ($H_2SO_4$), 11 N (VWR, Cat No. VW3481-1); and Proclin 300 (Supelco, Cat No. 4-8126).

The following plasticware and other materials were used: ELISA plate: 96-well, Maxisorp, flat bottom "F" (Nalge/Nunc International, VWR Cat No. 12-565-135); microcentrifuge tubes, 2.0 mL (Eppendorf, VWR Cat No. 62111-754); microplate adhesive film (USA Scientific, Cat No. 2920-0000); pipetman tips: 20 µL, 250 µL, and 1000 µL (Rainin Instruments, Cat Nos. GPS-L1000, GPS-L250, GPS-L10); reagent reservoir, 50 mL capacity (Corning, VWR Cat No. 82026-350); and serological pipettes, 10 mL and 25 mL (VWR, Cat No. 13-678-11D and 13-678-11E).

The following equipment and software were used: Elx405 Select Plate Washer (Bio-Tek); multichannel pipetman, 12-well, LTS 20-200 µL (Rainin Instruments); multichannel pipetman, 12-well, LTS 100-1200 µL (Rainin Instruments); pipet-aid, multi-speed, Drummond (VWR, Cat No. 13-681-15E); SOFTmax Pro v 3.0 (Molecular Devices); Spectra-Max PLUS Microplate Spectrophotometer (Molecular Devices); timer, three channel alarm (VWR, Cat No. 62344-600); and titer plate shaker (Barnstead/Lab-Line Instruments).

ELISA Protocol

Preparation of Samples.

Serum samples for screening were initially diluted 1:50 in Blocking Buffer. Samples with positive results were serially diluted three-fold in Blocking Buffer.

Preparation of Positive Controls.

Positive controls were a Cyno anti-PEG polyclonal antibody and a rabbit anti-PEG monoclonal antibody. The Cyno positive control used a Protein G purified total IgG from day 84 serum from a Cynomolgous monkey that had been immunized with rAvPAL-PEG. The Cyno positive control could be replaced by other Cyno or human sera identified as positive for anti-PEG IgG antibodies in this assay. Fluka 6 kDa hydroxyl PEG and inactivated 20 kDa methoxy PEG showed similar reactivity with the Cyno and rabbit anti-PEG antibody positive controls in this assay.

ELISA Procedure.

Inactivated methoxy PEG or hydroxy PEG was diluted to 1 µg/mL with Coating Buffer and dispensed at 100 µL per well into the ELISA plate. After incubation for 1 hour at 4° C., plates were washed 3× with 300 µL/well of Wash Buffer, and then 300 µL/well of Blocking Buffer was added to each well and incubated on a shaker for 1 hour at room temperature (RT). Plates were washed 3× with 300 µL/well of Wash Buffer. Serum samples and controls, diluted 1:50 in Blocking Buffer, were aliquoted at 100 µL/well according to a template plate map and incubated on a shaker for 1 hour at RT. Plates were washed 3× with 300 µL/well of Wash Buffer. HRP-conjugated Detection Reagent was prepared in Blocking Buffer at a 1:1,000 dilution, dispensed at 100 µL/well, and incubated on a shaker for 1 hour at RT. Plates were washed 3× with 300 µL/well of Wash Buffer. Development Reagent was added at 100 µL/well and the plate was incubated on a shaker for 15 minutes at RT. Stop Solution was added at 100 µL/well and the plate was read immediately at 450 nm.

Using this assay, anti-PEG antibodies of the IgG isotype can be specifically detected in clinical (e.g., serum) samples from humans, Example 13

Detection of IgM Antibodies Specific to Polyethylene Glycol (PEG) in Serum

An assay was developed to detect the presence of antibodies specific for polyethylene glycol (PEG) or derivatives thereof. In particular, an enzyme-linked immunosorbent assay (ELISA) method was developed to detect IgM antibodies to PEG in serum.

Materials

The following forms of PEG were used: 20 kDa methoxy PEG (NOF Corporation, Cat No. ME-200HS) inactivated by dissolution in TBS buffer, pH 7.5, and reconstituted to 2 mg/mL in TBS buffer, pH 7.5; and 6 kDa hydroxy PEG (Fluka, Cat No. 53770) (1.8 mg/mL in 0.1 M Tris-HCl, pH 8.0, 30% PEG 6000).

The following antibodies were used: detection reagent: HRP-conjugated goat anti-human IgM (Fc specific) (BioMarin).

The following matrices were used: Human serum (pooled); and individual human serum (Bioreclamation, Inc.).

The following ELISA reagents were used: coating buffer and wash buffer: 1×DPBS (Cellgro, Cat No. 21-031-CV); blocking buffer: Blocker Casein in PBS (Thermo, Cat No. 37528); development reagent: TMB Peroxidase EIA Substrate Kit, 250 mL (BioRad, Cat No. 172-1066); and stop solution: 2 N $H_2SO_4$.

The following chemicals were used: de-ionized water (MilliQ filtered); Dulbecco's phosphate buffered saline (DPBS), 1× (Cellgro, Cat No. 21-031-CV); sulfuric acid ($H_2SO_4$), 11 N (VWR, Cat No. VW3481-1); and Proclin 300 (Supelco, Cat No. 4-8126).

The following plasticware and other materials were used: ELISA plate: 96-well, Maxisorp, flat bottom "F" (Nalge/Nunc International, VWR Cat No. 12-565-135); microcentrifuge tubes, 2.0 mL (Eppendorf, VWR Cat No. 62111-754); microplate adhesive film (USA Scientific, Cat No. 2920-0000); pipetman tips: 20 µL, 250 µL, and 1000 µL (Rainin Instruments, Cat Nos. GPS-L1000, GPS-L250, GPS-L10); reagent reservoir, 50 mL capacity (Corning, VWR Cat No. 82026-350); and serological pipettes, 10 mL and 25 mL (VWR, Cat No. 13-678-11D and 13-678-11E).

The following equipment and software were used: Elx405 Select Plate Washer (Bio-Tek); multichannel pipetman, 12-well, LTS 20-200 µL (Rainin Instruments); multichannel pipetman, 12-well, LTS 100-1200 µL (Rainin Instruments); pipet-aid, multi-speed, Drummond (VWR, Cat No. 13-681-15E); SOFTmax Pro v 3.0 (Molecular Devices); Spectra-Max PLUS Microplate Spectrophotometer (Molecular Devices); timer, three channel alarm (VWR, Cat No. 62344-600); and titer plate shaker (Barnstead/Lab-Line Instruments).

ELISA Protocol

Preparation of Samples.

Serum samples for screening were initially diluted 1:50 in Blocking Buffer. Samples with positive results were serially diluted in Blocking Buffer as needed.

Preparation of Positive Controls.

Positive controls were Cyno anti-Peg polyclonal antibodies. The Cyno positive control used a Protein G purified total IgG from day 84 serum from a Cynomolgous monkey that had been immunized with rAvPAL-PEG. This sera elicited a strong anti-PEG IgG and an even stronger IgM antibody response. The Cyno positive control could be replaced by other Cyno or human sera identified as positive for anti-PEG IgM antibodies in this assay. Fluka 6 kDa hydroxy PEG and inactivated 20 kDa methoxy PEG showed similar reactivity with the Cyno anti-PEG antibody positive control in this assay.

ELISA Procedure.

Inactivated methoxy PEG or hydroxy PEG was diluted to 1 µg/mL with Coating Buffer and dispensed at 100 µL per well into the ELISA plate. After incubation for 1 hour at 4° C., plates were washed 3× with 300 µL/well of Wash Buffer, and then 300 µL/well of Blocking Buffer was added to each well and incubated on a shaker for 1 hour at room temperature (RT). Plates were washed 3× with 300 µL/well of Wash Buffer. Serum samples and controls, diluted 1:50 in Blocking Buffer, were aliquoted at 100 µL/well according to a template plate map and incubated on a shaker for 1 hour at RT. Plates were washed 3× with 300 μL/well of Wash Buffer. HRP-conjugated Detection Reagent was prepared in Blocking Buffer at a 1:5,000 dilution, dispensed at 100 μL/well, and incubated on a shaker for 1 hour at RT. Plates were washed 3× with 300 μL/well of Wash Buffer. Development Reagent was added at 100 μL/well and the plate was incubated on a shaker for 15 minutes at RT. Stop Solution was added at 100 μL/well and the plate was read immediately at 450 nm.

Using this assay, anti-PEG antibodies of the IgM isotype can be specifically detected in clinical (e.g., serum) samples from humans.

Example 14

Toxicity/Pharmacokinetic Studies of Pegylated Forms of AvPAL Variants (Cysteine Mutants) in Cynomolgus Monkeys and Rats Toxicity/pharmacokinetic studies were performed to determine the effect of administration of a single dose of a pegylated form of an AvPAL polypeptide variant (e.g., with serine substitution of the cysteine residues at positions 503 and 565) in Cynomolgus monkeys and in rats.

The pegylated AvPAL double cysteine mutant AvPAL_C565SC503S was prepared as described in Example 5.

Cynomolgus Monkey Toxicity/Pharmacokinetic Study

This study used four (4) groups of monkeys, each with three males and three females. Group 1 received placebo (mL/kg); and Groups 2, 3 and 4 received a single subcutaneous injection of pegylated AvPAL double cysteine mutant AvPAL_C565SC503S in solution at 4, 12 and 60 mg/kg, respectively. Plasma samples were collected from the monkeys pre-dose, and at various times post-dose, from 3 to 504 hours. The 60 mg/kg dose was found to be toxic to the monkeys, so the Group 4 portion of this study was terminated.

Figure 7A:
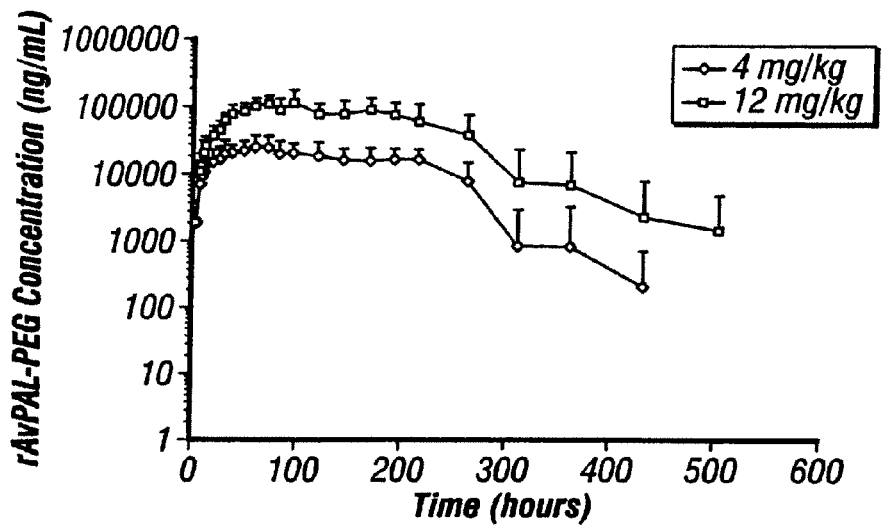
FIGS. 7A-7B.
Figure 7B:
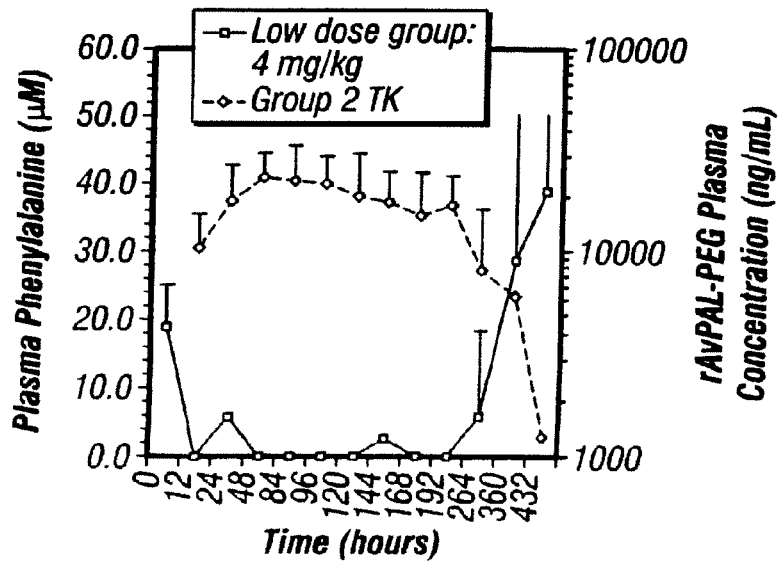

FIG. 7A shows the concentration of pegylated AvPAL double cysteine mutant AvPAL_C565SC503S in the plasma at various times after a single subcutaneous injection at 4 and 12 mg/kg. The data shows monophasic elimination of the pegylated AvPAL double cysteine mutant AvPAL_C565SC503S. A single compartment model with $1^{st}$ order absorption appears to describe the plasma profile of the pegylated AvPAL double cysteine mutant AvPAL_C565SC503S after a single subcutaneous injection.

FIG. 87B shows the concentrations of phenylalanine (Phe) and pegylated AvPAL double cysteine mutant AvPAL_C565SC503S in the plasma at various times after a single subcutaneous injection at 4 mg/kg. At this dose, the plasma Phe concentration was reduced to below the limit of quantitation in the GC/MS assay within 24 hours, and the drop in plasma Phe was sustained over 10 days.

Rat Toxicity/Pharmacokinetic Study

This study used eight (8) groups of rats, with 3 males and 3 females in the placebo groups, and 6 males and 6 females in the test groups. Groups 1 and 5 received single intravenous and subcutaneous injections of placebo. Groups 2, 3 and 4 received single intravenous injections of pegylated AvPAL double cysteine mutant AvPAL_C565SC503S at 1, 5 and 25 mg/kg, respectively. Groups 6, 7 and 8 received single subcutaneous injections of pegylated AvPAL double cysteine mutant AvPAL_C565SC503S at 10, 25 and 250 mg/kg, respectively. Blood samples were collected from the rats pre-dose, and at various times post-dose, from 1 to 360 hours. At each collection time, blood was collected from 3 rats in each group. No toxicity was observed in the rats in this study.

Figure 8A:
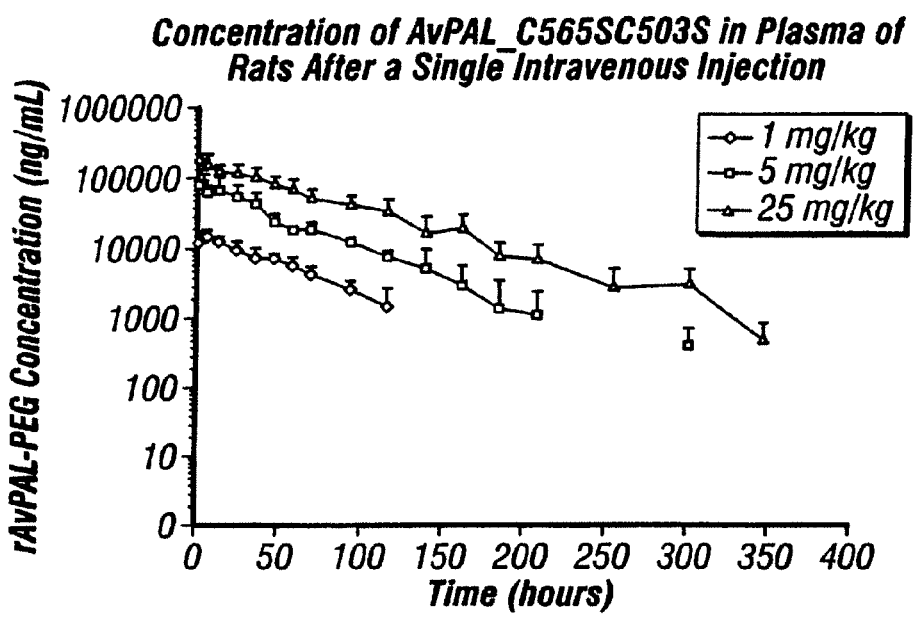
FIGS. 8A-8B.

FIG. 8A shows the concentration of pegylated AvPAL double cysteine mutant AvPAL_C565SC503S in the plasma at various times after a single intravenous injection at 1, 5 and 25 mg/kg. The data shows monophasic elimination of the pegylated AvPAL double cysteine mutant AvPAL_C565SC503S from the plasma after a single intravenous injection.

Figure 8B:
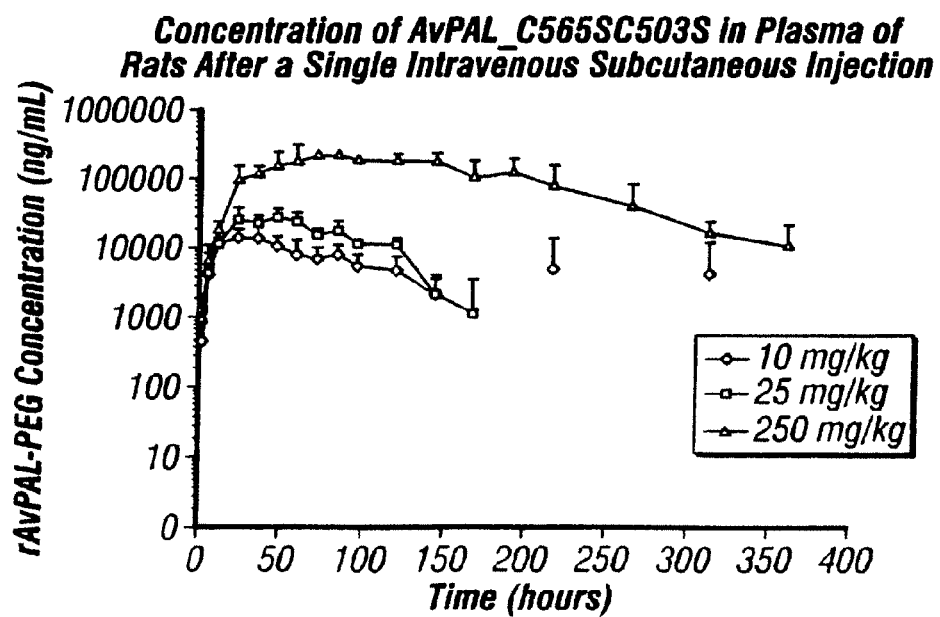

FIG. 8B shows the concentration of pegylated AvPAL double cysteine mutant AvPAL_C565SC503S in the plasma at various times after a single subcutaneous injection at 10, 25 and 250 mg/kg. A single compartment model with first order absorption appears to describe the plasma profile of the pegylated AvPAL double cysteine mutant AvPAL_C565SC503S after a single subcutaneous injection.

Table 2 shows pharmacokinetic parameters of the pegylated AvPAL double cysteine mutant AvPAL_C565SC503S after a single intravenous or subcutaneous injection.

TABLE 2

Pharmacokinetic Parameters of Pegylated Double Cysteine Mutant AvPAL_C565SC503S After a Single Intravenous or Subcutaneous Dose

| Route | Dose (mg/kg) | $AUC_{0-\infty}$ (ng-hr/mL) | $C_{max}$ (ng/mL) | $T_{max}$ (hr) | $t_{1/2}$* (hr) | F (%) |
|---|---|---|---|---|---|---|
| Intravenous | 1 | 657131 | 12600 | 4.5 | 27.9 | — |
|  | 5 | 3579327 | 87667 | 2 | 39.1 | — |
|  | 25 | 10860907 | 202238 | 9.0 | 30.4 | — |
| Subcutaneous | 10 | 1304016 | 16674 | 18.0 | 46.9 | 19.7 |
|  | 25 | 2290754 | 29260 | 42.0 | 21.0 | 12.5# |
|  | 250 | 37254683 | 225200 | 72.0 | 62.8 | 34.0 |

*For the subcutaneous route of administration, terminal $t_{1/2}$ is longer than intravenous; this may be due to a slower rate of absorption from subcutaneous tissues than the rate of elimination (so that the $t_{1/2}$ observed is actually absorption).
Bioavailability using intravenous AUC data at 25 mg/kg is 21.5%.

There appeared to be no gender difference in this pharmacokinetic study. The $AUC_{inf}$ and $C_{max}$ were roughly proportional with dose for both the intravenous and subcutaneous routes of administration.

Multiple Dose Toxicity Studies in Rats and Cynomolgus Monkeys

The safety of pegylated AvPAL double cysteine mutant AvPAL_C565SC503S was evaluated in repeat-dose toxicity studies in rats and Cynomolgus monkeys.

Rats administered up to 25 mg/kg pegylated AvPAL double cysteine mutant AvPAL_C565SC503S twice weekly, subcutaneously over 28 days exhibited no toxicity.

Cynomolgus monkeys administered up to doses of 1 mg/kg pegylated AvPAL double cysteine mutant AvPAL_C565SC503S twice weekly, subcutaneously over 28 days exhibited no significant toxicity. A dose dependent decrease in plasma Phe levels was observed after the first dose; however, after the seventh dose, plasma Phe levels returned to baseline in all dose groups, indicating a possible antibody response toward the administered enzyme. Minimal anti-AvPAL_C565SC503S IgG titers were observed in most 1 mg/kg treated animals at day 28. No IgM titers were observed in any animal in the study at day 28.

Example 15

Effects of AvPAL Variants (Cysteine Mutants) on Tumor Cells in Culture

Studies were performed to investigate the effect a pegylated form of an AvPAL polypeptide variant (e.g., with serine substitution of the cysteine residues at positions 503 and 565) on the proliferation of tumor cells grown in culture in vitro.

The pegylated AvPAL double cysteine mutant AvPAL_C565SC503S was prepared as described in Example 7.

The proliferation of tumor cells in vitro was measured using a propidium iodide fluorescence assay as described in Dengler, et al., Anti-Cancer Drugs 6:522-532 (1995).

Hematological Tumors

A panel of twenty-four (24) hematological tumor cell lines, including 14 leukemias, 5 lymphomas and 5 myelomas, were evaluated for the effect of pegylated double cysteine mutant AvPAL_C565SC503S on cell proliferation in vitro.

The hematological tumor cell lines were seeded into culture plates at 5,000 cells/well on Day 0. On Day 1, pegylated double cysteine mutant AvPAL_C565SC503S was added to the cultures at various concentrations, from 0.01 to 100 µg/mL. On Day 5, cells were harvested and DNA content was measured by propidium iodide staining. The $IC_{50}$, $IC_{70}$ and $IC_{90}$ were determined. These experiments were performed twice or three times for each hematological tumor cell line.

Table 3 shows that pegylated double cysteine mutant AvPAL_C565SC503S was effective in inhibiting in vitro proliferation, as measured by propidium iodide staining, of several hematological tumor cell lines.

TABLE 3

Inhibition of Propidium Iodide Staining of Hematological Tumor Lines In Vitro by Pegylated Double Cysteine Mutant AvPAL_C565SC503S

| Tumor Line | Cell Type | $IC_{50}$ µg/mL | $IC_{70}$ µg/mL |
|---|---|---|---|
| CCRF CEM | ALL - T Cell Lymphoma | 1 | >100 |
|  |  | >100 | >100 |
|  |  | >100 | >100 |
| EM2 | CML | >100 | >100 |
|  |  | >100 | >100 |
|  |  | >100 | >100 |
| HL-60 | APL | 0.904 | >100 |
|  |  | >100 | >100 |
|  |  | 46.41 | >100 |
| JURKAT | Human T Cell Leukemia | 0.38 | 2.928 |
|  |  | 14.125 | >100 |
|  |  | 10.000 | >100 |
| JURLMK1 | CML | 0.766 | >100 |
|  |  | 10 | >100 |
|  |  | 3.162 | >100 |
| K562 | CML | 0.701 | 59.948 |
|  |  | >100 | >100 |
|  |  | 11.659 | >100 |
| KCL22 | CML | 0.9 | 15.399 |
|  |  | >100 | >100 |
|  |  | 1 | >100 |
| KG1 | AML | 43.287 | >100 |
|  |  | >100 | >100 |
|  |  | >100 | >100 |
| MEG01 | CML | 1.258 | >100 |
|  |  | >100 | >100 |
|  |  | 0.926 | >100 |
| MOLT4 | ALL - T cell lymphoma | 0.326 | 1.873 |
|  |  | 1.082 | 5.298 |
|  |  | 1.096 | 6.918 |
| Mv411 | AML | 5.994 | 74.989 |
|  |  | >100 | >100 |
|  |  | >100 | >100 |
| NOMO1 | AML | 0.304 | 2.511 |
|  |  | 0.732 | 8.659 |
|  |  | 0.863 | 6.449 |

TABLE 3-continued

Inhibition of Propidium Iodide Staining of Hematological Tumor Lines In Vitro by Pegylated Double Cysteine Mutant AvPAL_C565SC503S

| Tumor Line | Cell Type | $IC_{50}$ µg/mL | $IC_{70}$ µg/mL |
|---|---|---|---|
| OCIAML2 | AML | 0.261 | 0.938 |
|  |  | >100 | >100 |
|  |  | 7.305 | >100 |
| PL21 | AML | >100 | >100 |
|  |  | >100 | >100 |
|  |  | >100 | >100 |
| HUT78 | Lym CTL | 6.105 | 18.276 |
|  |  | 17.782 | >100 |
|  |  | 0.096 | >100 |
| L5178Y | Mouse T cell Leukemia | 6.683 | 41.595 |
|  |  | 3.981 | 10 |
|  |  | 3.019 | 7.585 |
| MYLA | Lym CTL | 4.436 | >100 |
|  |  | 5.379 | >100 |
|  |  | 8.171 | >100 |
| RAJI | Burkitt Lymphoma | 0.261 | 0.938 |
|  |  | 21.544 | >100 |
|  |  | 2.154 | >100 |
| U937 | Histio Lymphoma | 0.803 | >100 |
|  |  | >100 | >100 |
|  |  | >100 | >100 |
| 8226 | Myeloma | 0.229 | 0.825 |
|  |  | >100 | >100 |
|  |  | 0.691 | 7.742 |
| IM9 | Human Lymphoblastic Cells | 0.271 | 1.467 |
|  |  | 0.295 | 1.311 |
|  |  | 0.063 | 0.188 |
| L363 | Human Plasma Cell Leukemia | 7.943 | >100 |
|  |  | 1.73 | 15.505 |
| LP1 | Human Multiple Myeloma | 0.774 | 100 |
|  |  | 0.71 | 6.309 |
| NCIH929 | Human Multiple Myeloma | >100 | >100 |
|  |  | 11.288 | >100 |
|  |  | 2.154 | >100 |

Figure 9A:
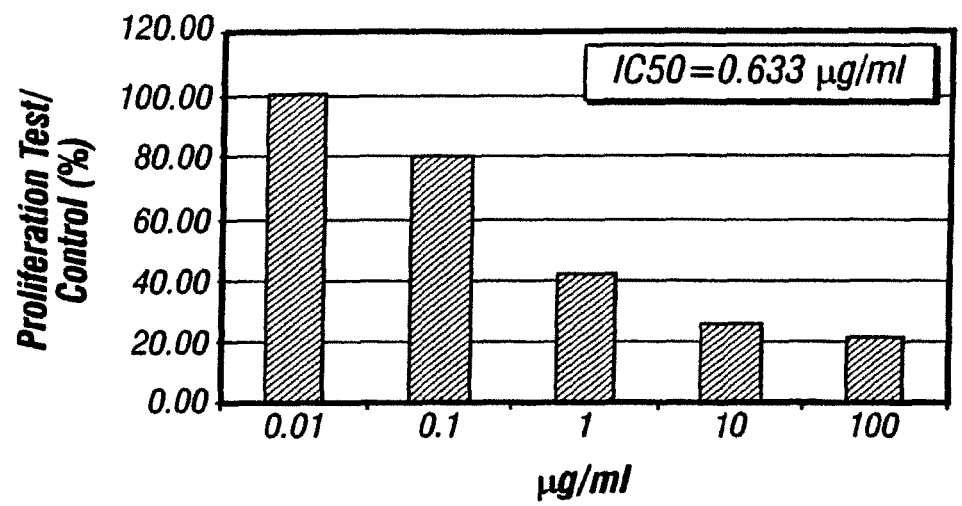
FIGS. 9A-9B.
Figure 9B:
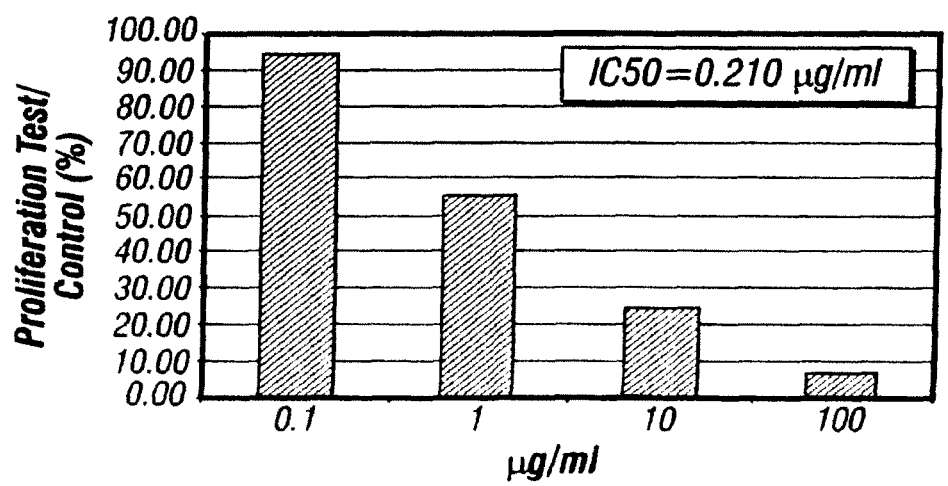
Figure 10A:
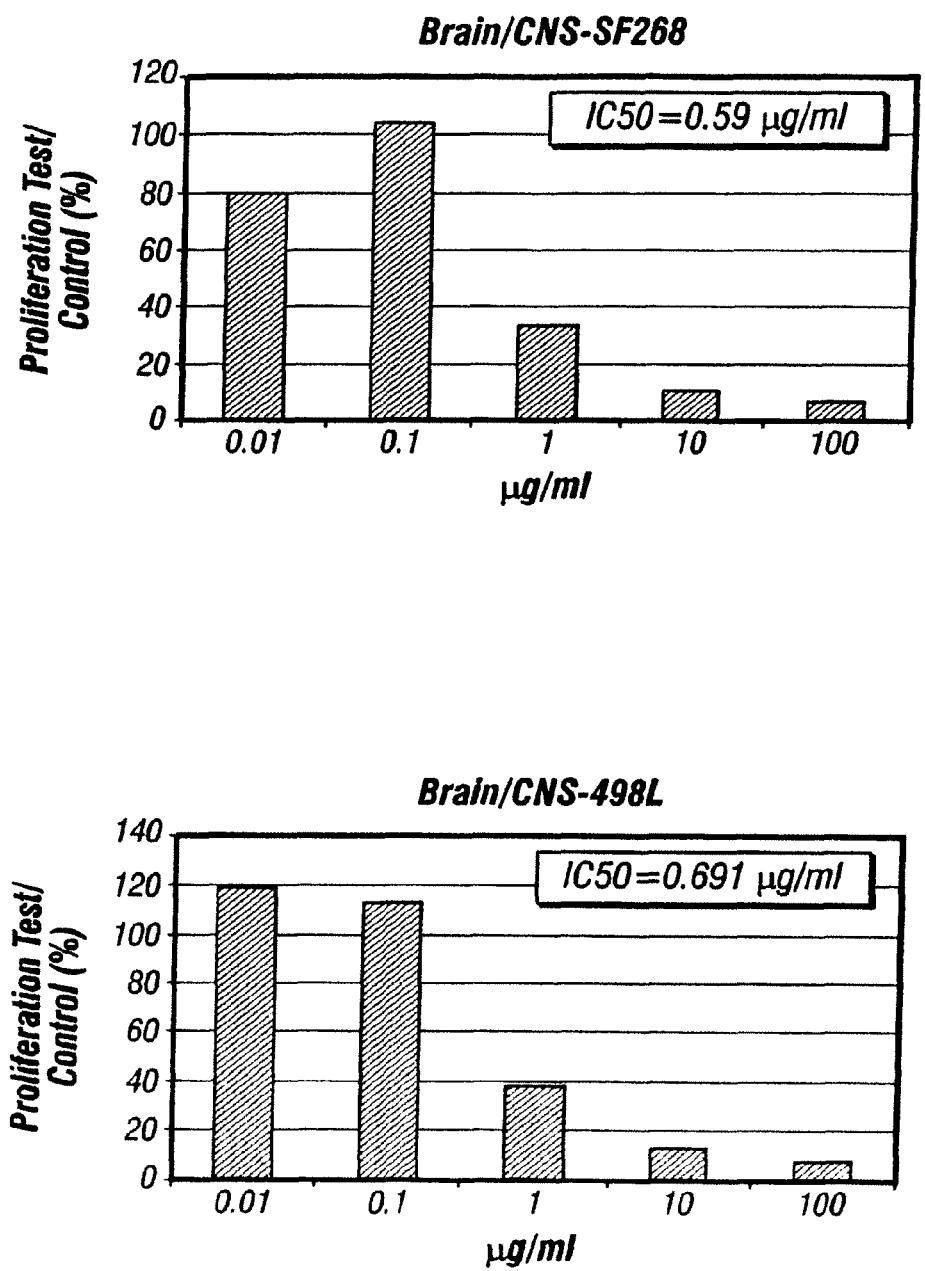
FIGS. 10A-10D.
Figure 10B:
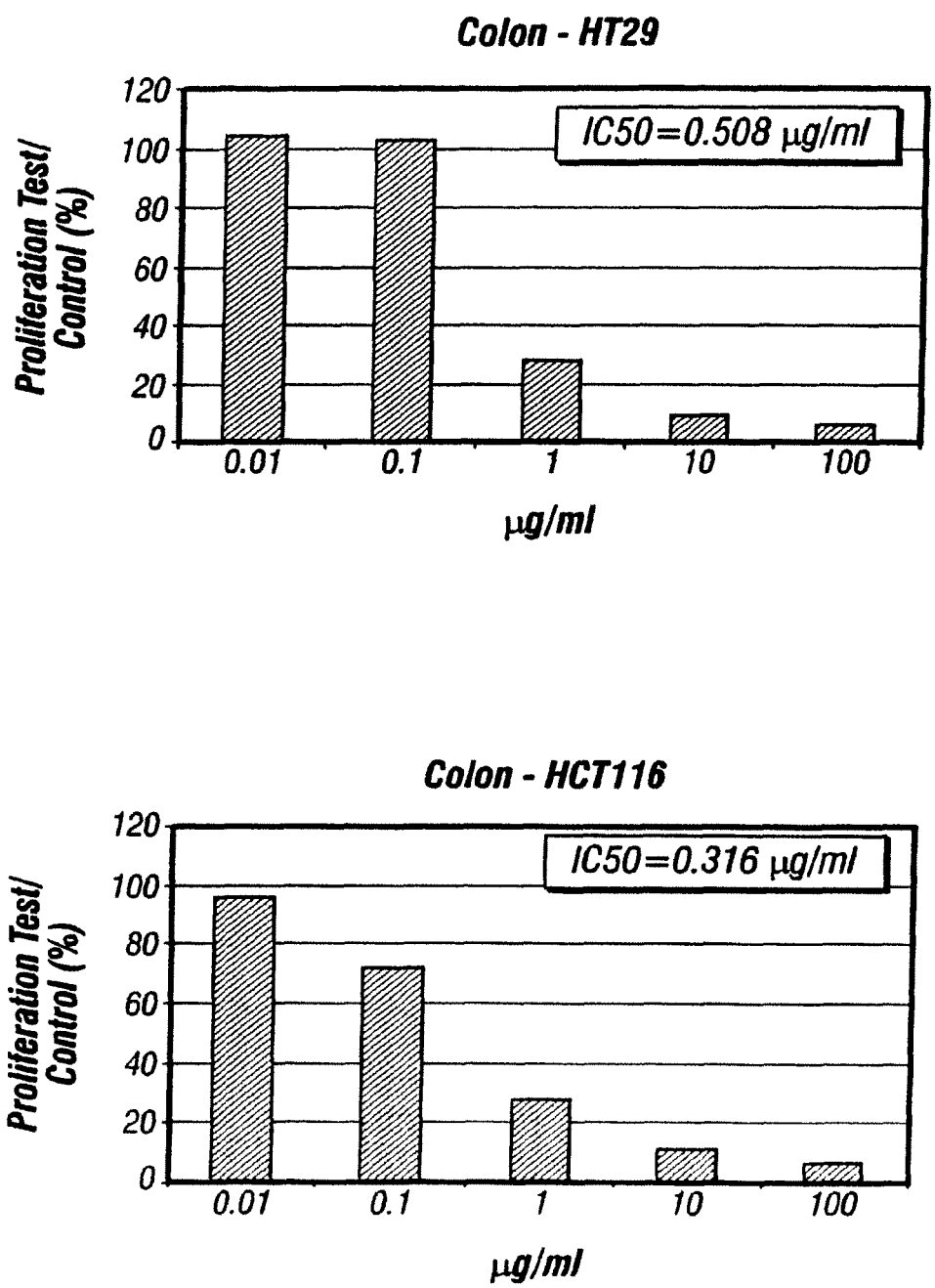
Figure 10C:
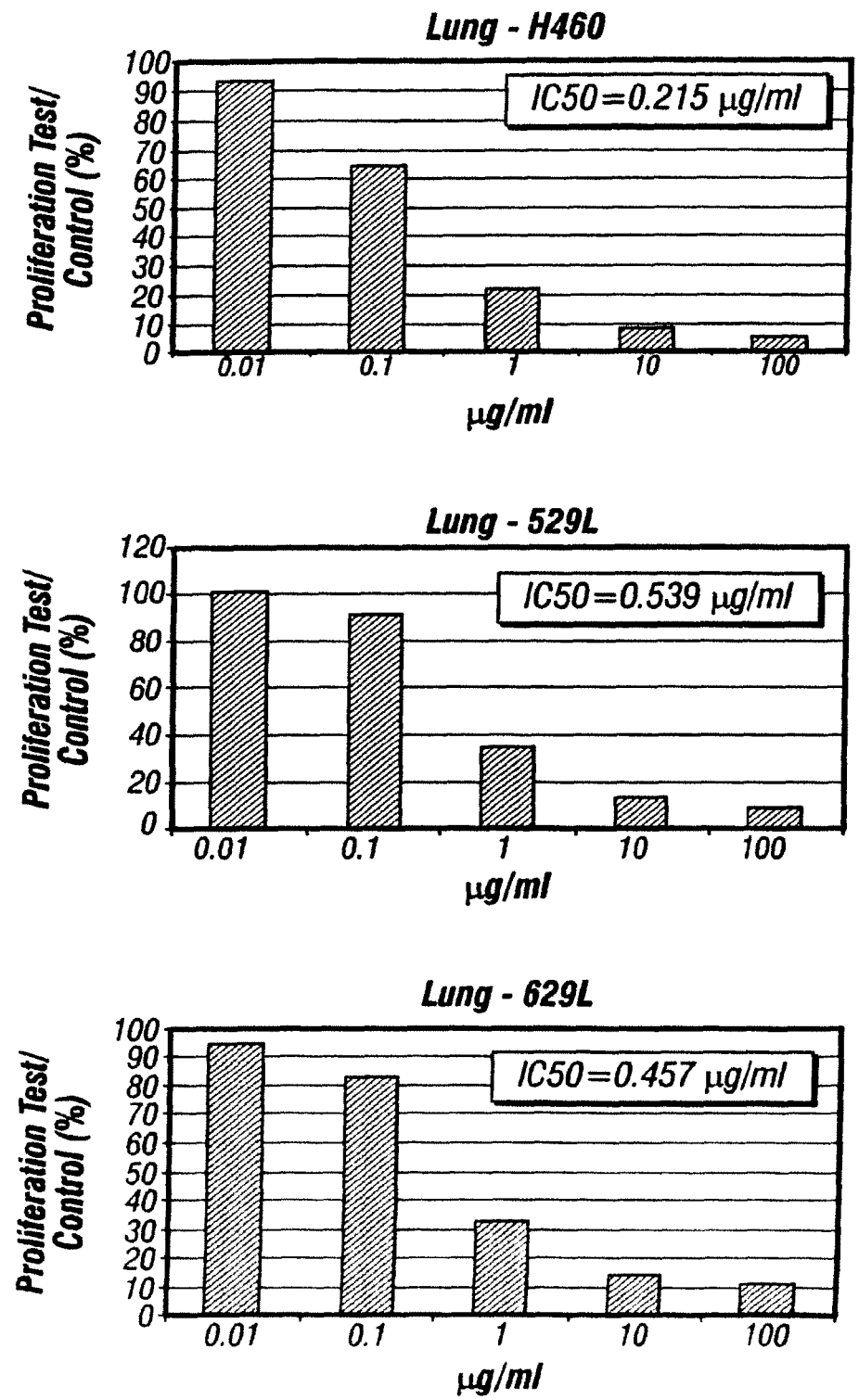
Figure 10D:
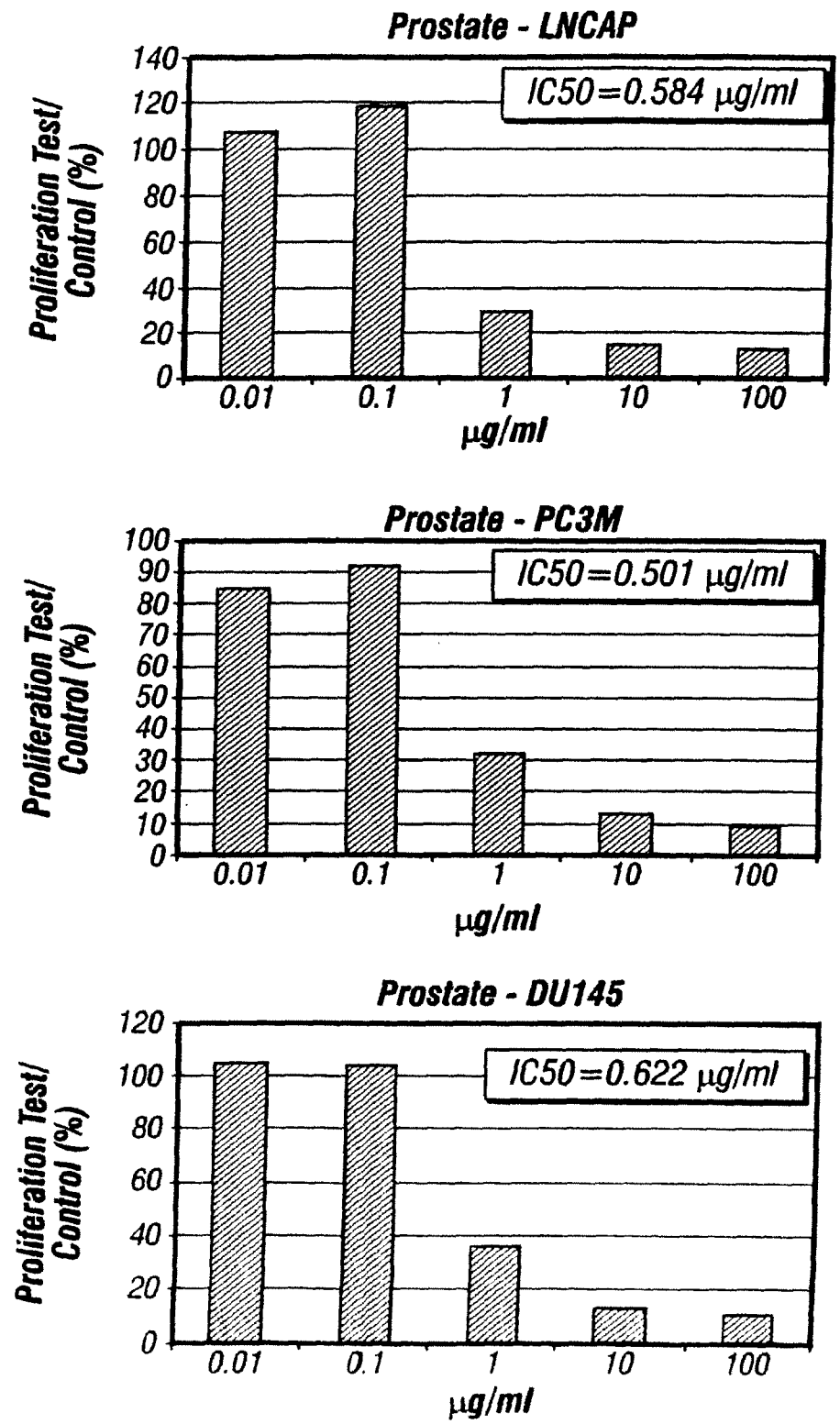

Dose-dependent inhibition of cell proliferation, as determined by a reduction in propidium iodide staining, by the pegylated double cysteine mutant AvPAL_C565SC503S in two sensitive hematological tumor cells, NOMO1 and IM9, are shown in FIGS. 9A and 9B, respectively. These tumor cell lines had $IC_{50}$ and $IC_{70}$ of less than 1.0 and 10.0 µg/mL, respectively. For comparison, asparaginase has an $IC_{50}$ of 1-10 µg/mL in human leukemia cell lines. In general, however, the hematological tumor cell lines were more resistant, as judged by $IC_{70}$ values, than the solid tumor lines (see below).

Solid Tumors

A panel of thirty-six (36) solid tumor cell lines, including tumors derived from bladder, brain, colon, stomach, head and neck, lung, breast, ovary, pancreas, prostate, kidney and uterus, were evaluated for the effect of pegylated double cysteine mutant AvPAL_C565SC503S on cell proliferation in vitro. The solid tumor cell lines were seeded into culture plates at 5,000 cells/well on Day 0. On Day 1, pegylated double cysteine mutant AvPAL_C565SC503S was added to the cultures at various concentrations, from 0.01 to 100 µg/mL. On Day 5, DNA content was measured by propidium iodide staining. The $IC_{50}$, $IC_{70}$ and $IC_{90}$ were determined.

Table 4 shows that pegylated double cysteine mutant AvPAL_C565SC503S was effective in inhibiting in vitro proliferation, as measured by propidium iodide staining, of several solid tumor cell lines.

TABLE 4

Inhibition of Propidium Iodide Staining of Solid Tumor Lines In Vitro by Pegylated Double Cysteine Mutant AvPAL_C565SC503S

| Tumor Line | Organ/Cell Type | IC$_{50}$ µg/mL | IC$_{70}$ µg/mL |
|---|---|---|---|
| Bladder | | | |
| 1218L | ATCC, Freiburg; Urothelial Adenocarcinoma | 1.1 | 7.498 |
| T24 | Xenograft | 0.617 | 2.154 |
| Brain/CNS | | | |
| 498NL | Xenograft, Freiburg | 0.691 | 2.154 |
| SF268 | NCI | 0.59 | 1.492 |
| Colon | | | |
| HCT116 | NCI; Adenocarcinoma, pd | 0.316 | 0.9 |
| HT29 | NCI; Adenocarcinoma, pd | 0.508 | 0.94 |
| Gastric | | | |
| 251L | Xenograft, Freiburg; Adenocarcinoma, pd | 2.682 | 37.275 |
| Head and Neck | | | |
| 536L | Xenograft, Freiburg; Hypopharynx Carcinoma | 0.606 | 1.887 |
| Lung | | | |
| 1121L | Xenograft | 0.715 | 3.548 |
| 289L | Xenograft, Freiburg; Adenocarcinoma, pd | 2.807 | 23.101 |
| 529L | Xenograft, Freiburg; Large Cell, du | 0.539 | 1.73 |
| 629L | Xenograft, Freiburg; Adenocarcinoma, pd | 0.457 | 1.467 |
| H460 | NCI; Large Cell Carcinoma | 0.215 | 0.644 |
| Breast | | | |
| 401NL | Xenograft, Freiburg; Pap Adenocarcinoma, wd | 1.873 | 7.564 |
| MCF7 | NCI; Mammary Carcinoma | 0.599 | 1.623 |
| Melanoma | | | |
| 276L | Xenograft | 4.124 | 268.269 |
| 394NL | Xenograft | 0.887 | 3.856 |
| 462NL | Xenograft | 0.954 | 6.189 |
| 514L | Xenograft | 0.828 | 4.216 |
| 520L | Xenograft | 1.359 | 6.309 |
| Ovarian | | | |
| 1619L | Xenograft, Freiburg; Adenocarcinoma, md | 0.322 | 0.688 |
| 899L | Xenograft, Freiburg; Pap Serous Carcinoma, md | 1.279 | 6.628 |
| OVCAR3 | NCI; Adenocarcinoma, md | 1.185 | 6.528 |
| Pancreatic | | | |
| 1657L | Xenograft, Freiburg; Adenocarcinoma, md | 1.951 | 8.619 |
| PANC1 | ATCC | 0.825 | 5.179 |
| Prostate | | | |
| 22RV1 | ATCC; Adenocarcinoma, md | 0.87 | 7.079 |
| DU145 | NCI; Adenocarcinoma, md | 0.622 | 1.873 |
| LNCAP | DSMZ; Adenocarcinoma, md | 0.584 | 0.974 |
| PC3M | NCI; Adenocarcinoma, md | 0.501 | 1.274 |
| Pleuramesothelioma | | | |
| 1752L | Xenograft, Freiburg; Pleuramesothelioma | 1.637 | 8.483 |
| Renal | | | |
| 1781L | Xenograft, Freiburg; Renal Carcinoma | 2.371 | 10 |
| 393NL | Xenograft, Freiburg; Hypernephroma, wd | 0.55 | 1.995 |
| 486L | Xenograft | 0.859 | 5.336 |
| 944L | Xenograft | 0.71 | 3.727 |
| Uterine | | | |
| 1138L | Xenograft, Freiburg; Carcinosarcoma, wd | 0.621 | 1.258 |

Dose-dependent inhibition of cell proliferation, as determined by a reduction of propidium iodide staining, by the pegylated double cysteine mutant AvPAL_C565SC503S in tumor cell lines derived from brain/CNS, colon, lung and prostate cancer is shown in FIGS. 10A-10D, respectively.

The AvPAL_C565SC503S displayed a selective anti-proliferative activity in this broad panel of solid tumor cell lines, and was particularly potent (i.e., IC$_{50}$ between 0.2 and 0.7 µg/mL) in tumor cell lines derived from lung, brain/CNS, colon, prostate and kidney. At least on tumor cell line derived from bladder, head and neck, breast, ovary and uterus were also sensitive to cell killing by AvPAL_C565SC503S. Several melanomas were also sensitive to cell killing by AvPAL_C565SC503S.

Example 16

Antitumor Activity of AvPAL Variants (Cysteine Mutants) in Nude Mice

Studies are performed to investigate the effect of a pegylated form of an AvPAL polypeptide variant (e.g., with serine substitution of the cysteine residues at positions 503 and 565) on the proliferation of tumor cells grown in nude mice in vivo.

The pegylated AvPAL double cysteine mutant AvPAL_C565SC503S is prepared as described in Example 7.

Subcutaneous xenografts of human tumor cells in immunodeficient nude or SCID mice have been successfully used as models for human cancers to test the in vivo efficacy of cancer therapeutic agents as well as targeted cancer therapeutic agents, such as antibodies and toxin conjugates (for review, see Kerbel, Cancer Biol. Ther. 2(4): Suppl. 1:S134-S139 (2003)).

The in vivo antitumor activity of the pegylated AvPAL double cysteine mutant AvPAL_C565SC503S can be tested alone or in combination with cancer therapeutic agents or targeted cancer therapeutic agents, or in combination with a phenylalanine-restricted diet, using xenografts of human tumor cells in nude mice.

To establish human tumor xenografts, nude mice are injected subcutaneously with about 5×10$^6$ human tumor cells in 0.2 mL PBS. The average tumor size increases over time. Human xenograft tumors are excised from the tumor bearing nude mice and tumor tissue blocks of approximately 30 mm$^3$ are prepared. Naive nude mice to be used for evaluating in vivo antitumor activity of pegylated AvPAL double cysteine mutant AvPAL_C565SC503S are each implanted subcutaneously with one tumor tissue block. Therapeutic treatment is initiated before tumor initiation or when the average tumor size within a group of nude mice is approximately 100-150 mm$^3$ (prevention model), and/or after the establishment of tumors when the average tumor size within a group of nude mice is above 500 mm$^3$ (treatment model).

In a first step, the dose of pegylated AvPAL double cysteine mutant AvPAL_C565SC503S that will lower plasma phenylalanine (Phe) levels to near zero is determined. Experiments are performed such as those described in Examples 7 to 9 and 14 in prior co-pending U.S. patent application Ser. No. 11/451,999 filed on Jun. 12, 2006, except nude mice rather than ENU2 mice are used. The PAL enzyme dose and the frequency of administration are determined in this initial step.

In a second step, the anti-tumor activity of pegylated AvPAL double cysteine mutant AvPAL_C565SC503S is assessed in various human tumor xenografts derived from patients or cell lines. Tumor models include different cancer types, for example and not for limitation, central nervous system (CNS), colon, lung, prostate, metastatic melanoma and renal cancer. Non-comprehensive lists of tumors and tumor cell lines that can be tested are provided in Tables 3 (hematological tumors) and 4 (solid tumors).

To assess the antitumor activity of pegylated AvPAL double cysteine mutant AvPAL_C565SC503S, nude mice bearing different human tumor xenografts subcutaneously are treated with AvPAL_C565SC503S given subcutaneously at, e.g., three different dose levels, ranging from about 5 to 500 mg/kg. This dose may result in a human dose of about 0.1 to 10 mg/kg. Antitumor activity is analyzed as tumor volume inhibition and/or absolute growth delay. The tolerability of the AvPAL_C565SC503S is also evaluated as mortality and/or body weight changes.

Each in vivo antitumor study consists of at least four groups, one vehicle control group and at least three prokaryotic PAL enzyme-treated groups. The group size will be at least 8 mice, resulting in a total of 32 mice receiving subcutaneous tumor implantations. Mice with similar sized tumors (100-150 mm$^3$) will be used for randomization (Day 0).

In the case of an antitumor effect, mice may be monitored for additional 2 weeks after termination of prokaryotic PAL enzyme treatment to detect a possible reinitiation of tumor growth. According to regulations for animal experiments, mice are sacrificed if the tumor diameters exceed 1.6 cm.

Tumor diameters are measured twice weekly together with body weight. Tumor volume is calculated according to the formula a*b$^2$/2 (where 'a' is the largest diameter of the tumor and 'b' is the perpendicular axis). Relative tumor volumes and body weights are calculated for each individual tumor based on the value on Day 0 (the first day of dosing). Treatment starts when the tumors have reached a volume of approximately 100-150 mm$^3$. Mice are sacrificed if the tumor volume exceeds 1600 mm$^3$, per regulations for animal studies.

Patient-derived tumors established in serial passage in nude mice can also be used as test tumors. Typically, these tumors retain important characteristics of the original patient tumor, including histology and drug sensitivity. For certain tumors, e.g., one CNS and both prostate cancers, cancer cell line-derived tumors are used.

Example 17

Clinical Evaluation with Prokaryotic PAL Compositions for Treatment of Cancer

The following example provides guidance on the parameters to be used for the clinical evaluation of compositions comprising prokaryotic PAL or biologically active fragments, mutant, variants or analogs thereof in the therapeutic methods and kits provided herein. As discussed herein throughout, prokaryotic PAL compositions can be used, e.g., in the treatment of cancer. Clinical trials will be conducted which will provide an assessment of oral or subcutaneous doses of prokaryotic PAL for safety, pharmacokinetics, and initial response of both surrogate and defined clinical endpoints. The trial will be conducted for a minimum, but not necessarily limited to, 24 weeks to collect sufficient safety information for 100 evaluable patients. The initial dose for the trials will vary from about 0.001 to about 1.0 mg/kg/week. In the event that this dose does not produce a reduction in plasma phenylalanine (Phe) levels in a patient, e.g., a reduction from the normal range about 50 μM to about 70 μM to a range from below the level of detection to less than about 30 μM, preferably less than about 20 μM, and even more preferably less than about 10 μM, the dose should be increased as necessary, and maintained for an additional minimal period of, but necessarily limited to, 24 weeks to establish safety and to evaluate further efficacy.

Measurements of safety will include adverse events, allergic reactions, complete clinical chemistry panel (kidney and liver function), urinalysis, and CBC with differential. In addition, other parameters including the reduction in levels of blood Phe levels, neuropsychological and cognitive testing, and global assessments also will be monitored. The present example also contemplates the determination of pharmacokinetic parameters of the drug in the circulation, and general distribution and half-life of PAL in blood. It is anticipated that these measures will help relate dose to clinical response.

Methods

Cancer-free control patients and patients who have been diagnosed with a form of cancer will undergo a baseline a medical history and physical exam, neuropsychological and cognitive testing, a standard set of clinical laboratory tests (CBC, Panel 20, CH50, UA), levels of urinary pterins, dihydropteridine reductase (DHPR) levels, and a fasting blood (plasma) panel of serum amino acids. Baseline blood, serum or plasma Phe levels will be measured. The patient will be followed closely with weekly visits to the clinic. Patients will return to the clinic for a complete evaluation one week after completing the treatment period. Should dose escalation be required, the patients will follow the same schedule outlined above. Safety will be monitored throughout the trial.

Diagnosis and Inclusion/Exclusion Criteria

The patient may be male or female, with a documented diagnosis of a form of cancer. The study will include cancer patients who have previously undergone surgery, chemotherapy, radiation therapy and/or other anti-cancer therapy and are in remission (e.g., disease-free for at least 5 years). A patient will be excluded from this initial study if the patient has been diagnosed with a form of cancer, but has not undergone some form of anti-cancer therapy.

Prokaryotic PAL Safety

Prokaryotic PAL therapy will be determined to be safe if no significant acute or chronic drug reactions occur during the course of the study. The longer-term administration of the drug will be determined to be safe if no significant abnormalities are observed in the clinical examinations, clinical labs, or other appropriate studies.

Prokaryotic PAL Efficacy

Once prokaryotic PAL therapy has been determined to be safe and effective to reduce the plasma phenylalanine (Phe) levels in a patient, e.g., a reduction from the normal range about 50 μM to about 70 μM to a range from below the level of detection to less than about 30 μM, preferably less than about 20 μM, and even more preferably less than about 10 μM, the prokaryotic PAL compositions provided herein can be tested in cancer patients who have previously undergone surgery, chemotherapy, radiation therapy and/or other anti-cancer therapy and are in remission (e.g., disease-free for at least 5 years), as well as in patients who have been diagnosed with a form of cancer, but have not as yet undergone any form of anti-cancer therapy.

For cancer patients in remission, prokaryotic PAL is administered, alone or in combination with standard cancer therapy for the particular form of cancer, to determine whether patients given the PAL therapy remain in remission (i.e., disease-free) for a longer period of time than patients not given prokaryotic PAL compositions provided herein.

For cancer patients with an active form of cancer, prokaryotic PAL is administered, alone or in combination with standard cancer therapy for the particular form of cancer, to determine whether patients given the PAL therapy have a better response to the cancer therapy (e.g., remain disease-free longer, have longer survival time, or have lower tumor growth, tumor size or tumor burden) than patients not given prokaryotic PAL compositions provided herein.

Prokaryotic PAL therapy can be administered alone, or in combination with a cancer therapeutic agent or targeted cancer therapeutic agent, or with a protein-restricted diet (i.e., phenylalanine-free), or both.

SEQUENCE LISTING

The present specification is being filed with a computer readable form (CRF) copy of the Sequence Listing. The CRF entitled 11808-253-999_SEQLIST.txt, which was created on Jan. 20, 2016, is 45,021 bytes in size, and also serves as the paper copy of the Sequence Listing, is incorporated herein by reference in its entirety.

What is claimed:

1. A method for detecting the presence of pegylated *Anabaena variabilis* phenylalanine ammonia-lyase (AvPAL-PEG)-specific antibodies in a sample, said method comprising:
   (a) contacting the sample with recombinant AvPAL-PEG enzyme, wherein the recombinant AvPAL-PEG enzyme is immobilized on a solid support via a PEG-specific antibody;
   (b) optionally removing unbound sample;
   (c) adding a phenylalanine substrate; and
   (d) detecting the presence of enzymatic activity between the immobilized recombinant AvPAL-PEG enzyme and phenylalanine substrate;
   wherein a reduction of enzymatic activity as compared to a reference sample having no neutralizing AvPAL-PEG-specific antibodies indicates the presence of neutralizing AvPAL-PEG-specific antibodies in the sample.

2. The method of claim 1, wherein the enzymatic activity is conversion of the phenylalanine substrate to trans-cinnamic acid.

3. The method of claim 1, further comprising measuring the amount of the neutralizing AvPAL-PEG-specific antibodies in the sample.

4. The method of claim 1, wherein the AvPAL is an AvPAL variant.

5. The method of claim 4, wherein the AvPAL variant is AvPAL_C503S, AvPAL_C565S or AvPAL_C565SC503S.

6. The method of claim 1, wherein the sample comprises a bodily fluid or tissue.

7. The method of claim 6, wherein the bodily fluid is blood, serum or plasma.

8. The method of claim 1, wherein the sample is from a patient.

9. The method of claim 8, wherein the patient is a mammal.

10. The method of claim 9, wherein the mammal is a human.

11. The method of claim 8, wherein the patient is a patient having elevated phenylalanine levels.

12. The method of claim 8, wherein the patient has phenylketonuria.

13. The method of claim 8, wherein the patient has cancer.

14. The method of claim 8, wherein the patient has been, is, or will be administered a PAL, PAL variant, PAL-PEG, PAL-PEG variant or any combination thereof.

* * * * *

SEQUENCE LISTING

<160> NUMBER OF SEQ ID NOS: 31

<210> SEQ ID NO 1
<211> LENGTH: 1710
<212> TYPE: DNA
<213> ORGANISM: Nostoc punctiforme

<400> SEQUENCE: 1

```
atgaatataa catctctaca acagaacata acgcgttctt ggcaaatacc tttcactaat      60
agttcagatt caatcgtaac tgtaggcgat cgcaatctga caatcgacga ggttgtaaat     120
gttgctcgtc atggaacaca ggtgcgctta actgataatg cagatgtcat tcggggtgtt     180
caagcatctt gtgattacat taacaatgca gtcgaaacag cacagccaat ttacggggtg     240
acatctggct ttggcggtat ggcagatgtt gtcatctctc gcgaacaagc agcggaactt     300
cagactaatt taatttggtt tctgaaatcc ggcgcaggaa acaaattatc gttagcagac     360
gtgcgtgcag ctatgctctt acgtgcaaat tcacatttgt atggtgcgtc tggtatacga     420
ctcgaactta ttcagcggat tgaaactttc ctcaacgctg gcgtgacacc ccatgtctat     480
gagtttggct ctatcggtgc tagcggcgat ttggtgccat tatcctacat tactggggca     540
ctaatcggtc tagatcctag ctttacagtt gacttcgacg gtaaagaaat ggatgccgtt     600
acagccttgt ctcgtttggg tttgccaaag ttgcaattgc aaccgaaaga aggtttagca     660
atgatgaatg gcacctcagt catgacaggt attgcagcta actgtgtgta cgatgcgaaa     720
gttttgctcg ctctgacaat gggtgtacac gccttagcca tccaaggttt atacggaacg     780
aatcaatctt tccacccgtt tattcatcag tgcaagccac atcccggtca actatggaca     840
gcagatcaaa tgttttctct gctgaaagat tcatctttag ttcgtgaaga gttggatggt     900
aaacacgaat accgtggtaa agatctgata caggatcgtt attctctccg ctgtctggca     960
cagttcatag ggccaatcgt tgatggggta tcagagatta ccaagcaaat cgaggtagaa    1020
atgaactcag tcaccgataa cccattgatt gatgtcgaga accaagttag ttatcacggc    1080
ggcaattttc tcggacagta tgtgggtgtg acaatggatc gcctacgtta ttacataggg    1140
ctattggcca aacacatcga tgtgcagatt gcacttcttg tctcgccaga gtttagcaac    1200
ggcttaccac cctctttagt tggtaatagc gatcgcaaag ttaatatggg actcaaaggt    1260
ttgcaaatca gtggaaactc gattatgcca ctgttgagct tctatggaaa ttccctagcc    1320
gatcgctttc ctacccacgc cgagcaattt aatcaaaata ttaacagcca aggctatatt    1380
tccgcaaatt tgacacgtcg ttccgtagac atatttcaga attatatggc gatcgcgttg    1440
atgtttggag ttcaagctgt tgacctccgc acatataaga tgaaaggtca ttatgatgca    1500
cgtacatgcc tctcacccaa tactgtgcag ttatacacag cagtctgcga ggtagttgga    1560
aagccactaa cgtctgtgcg tccatacatt tggaacgaca acgagcaatg tttagatgag    1620
catattgccc ggatttcagc tgatatcgct ggtggtggtt taattgtgca agcagttgag    1680
```

```
catatttttt cgagcttaaa gtcaacgtaa                                              1710
```

<210> SEQ ID NO 2
<211> LENGTH: 569
<212> TYPE: PRT
<213> ORGANISM: Nostoc punctiforme

<400> SEQUENCE: 2

```
Met Asn Ile Thr Ser Leu Gln Gln Asn Ile Thr Arg Ser Trp Gln Ile
1               5                   10                  15

Pro Phe Thr Asn Ser Ser Asp Ser Ile Val Thr Val Gly Asp Arg Asn
            20                  25                  30

Leu Thr Ile Asp Glu Val Val Asn Val Ala Arg His Gly Thr Gln Val
        35                  40                  45

Arg Leu Thr Asp Asn Ala Asp Val Ile Arg Gly Val Gln Ala Ser Cys
    50                  55                  60

Asp Tyr Ile Asn Asn Ala Val Glu Thr Ala Gln Pro Ile Tyr Gly Val
65                  70                  75                  80

Thr Ser Gly Phe Gly Gly Met Ala Asp Val Val Ile Ser Arg Glu Gln
                85                  90                  95

Ala Ala Glu Leu Gln Thr Asn Leu Ile Trp Phe Leu Lys Ser Gly Ala
            100                 105                 110

Gly Asn Lys Leu Ser Leu Ala Asp Val Arg Ala Ala Met Leu Leu Arg
        115                 120                 125

Ala Asn Ser His Leu Tyr Gly Ala Ser Gly Ile Arg Leu Glu Leu Ile
    130                 135                 140

Gln Arg Ile Glu Thr Phe Leu Asn Ala Gly Val Thr Pro His Val Tyr
145                 150                 155                 160

Glu Phe Gly Ser Ile Gly Ala Ser Gly Asp Leu Val Pro Leu Ser Tyr
                165                 170                 175

Ile Thr Gly Ala Leu Ile Gly Leu Asp Pro Ser Phe Thr Val Asp Phe
            180                 185                 190

Asp Gly Lys Glu Met Asp Ala Val Thr Ala Leu Ser Arg Leu Gly Leu
        195                 200                 205

Pro Lys Leu Gln Leu Gln Pro Lys Glu Gly Leu Ala Met Met Asn Gly
    210                 215                 220

Thr Ser Val Met Thr Gly Ile Ala Ala Asn Cys Val Tyr Asp Ala Lys
225                 230                 235                 240

Val Leu Leu Ala Leu Thr Met Gly Val His Ala Leu Ala Ile Gln Gly
                245                 250                 255

Leu Tyr Gly Thr Asn Gln Ser Phe His Pro Phe Ile His Gln Cys Lys
            260                 265                 270

Pro His Pro Gly Gln Leu Trp Thr Ala Asp Gln Met Phe Ser Leu Leu
        275                 280                 285

Lys Asp Ser Ser Leu Val Arg Glu Glu Leu Asp Gly Lys His Glu Tyr
    290                 295                 300

Arg Gly Lys Asp Leu Ile Gln Asp Arg Tyr Ser Leu Arg Cys Leu Ala
305                 310                 315                 320

Gln Phe Ile Gly Pro Ile Val Asp Gly Val Ser Glu Ile Thr Lys Gln
                325                 330                 335

Ile Glu Val Glu Met Asn Ser Val Thr Asp Asn Pro Leu Ile Asp Val
            340                 345                 350

Glu Asn Gln Val Ser Tyr His Gly Gly Asn Phe Leu Gly Gln Tyr Val
        355                 360                 365
```

```
Gly Val Thr Met Asp Arg Leu Arg Tyr Tyr Ile Gly Leu Leu Ala Lys
        370                 375                 380

His Ile Asp Val Gln Ile Ala Leu Leu Val Ser Pro Glu Phe Ser Asn
385                 390                 395                 400

Gly Leu Pro Pro Ser Leu Val Gly Asn Ser Asp Arg Lys Val Asn Met
            405                 410                 415

Gly Leu Lys Gly Leu Gln Ile Ser Gly Asn Ser Ile Met Pro Leu Leu
        420                 425                 430

Ser Phe Tyr Gly Asn Ser Leu Ala Asp Arg Phe Pro Thr His Ala Glu
        435                 440                 445

Gln Phe Asn Gln Asn Ile Asn Ser Gln Gly Tyr Ile Ser Ala Asn Leu
    450                 455                 460

Thr Arg Arg Ser Val Asp Ile Phe Gln Asn Tyr Met Ala Ile Ala Leu
465                 470                 475                 480

Met Phe Gly Val Gln Ala Val Asp Leu Arg Thr Tyr Lys Met Lys Gly
            485                 490                 495

His Tyr Asp Ala Arg Thr Cys Leu Ser Pro Asn Thr Val Gln Leu Tyr
            500                 505                 510

Thr Ala Val Cys Glu Val Val Gly Lys Pro Leu Thr Ser Val Arg Pro
        515                 520                 525

Tyr Ile Trp Asn Asp Asn Glu Gln Cys Leu Asp Glu His Ile Ala Arg
        530                 535                 540

Ile Ser Ala Asp Ile Ala Gly Gly Leu Ile Val Gln Ala Val Glu
545                 550                 555                 560

His Ile Phe Ser Ser Leu Lys Ser Thr
            565
```

<210> SEQ ID NO 3
<211> LENGTH: 1704
<212> TYPE: DNA
<213> ORGANISM: Anabaena variabilis

<400> SEQUENCE: 3

```
atgaagacac tatctcaagc acaaagcaaa acctcatctc aacaattttc ttttactgga      60
aattcttctg ccaatgtaat tattggtaat cagaaactca caatcaatga tgttgcaagg     120
gtagcgcgta atggcacctt agtgtcttta accaataaca ctgatatttt gcagggtatt     180
caggcatctt gtgattacat taataatgct gttgaatctg gggaaccaat ttatggagtg     240
acatctggtt ttggcggtat ggccaatgtt gccatatccc gtgaacaagc atctgaactc     300
caaaccaact tagtttggtt cctgaaaaca ggtgcaggga caaattacc  cttggcggat     360 gtgcgcgcag ctatgctctt gcgtgcaaac tctcatatgc gcggtgcatc tggcatcaga     420
ttagaactta tcaagcgtat ggagattttc cttaacgctg tgtcacacc  atatgtgtat     480 gagtttggtt caattggtgc aagtggtgat ttagtgccac tatcctacat tactggttca     540
ctgataggct tagatcccag ttttaaggtt gacttcaacg gtaaagaaat ggatgcgcca     600
acagctctac gtcaactgaa tttgtcaccc ttgacattgt tgccgaagga aggcttggcg     660
atgatgaacg gcacttcagt catgacaggt attgcagcaa actgcgtcta cgatactcaa     720 atttaactg cgatcgctat gggcgttcac gctctagata ccaagctttt aaacggaacc     780
aatcaatcat tccatccatt tatccataat tccaaaccac atcctggtca attatgggca     840
gcagatcaga tgtttctttt gttagccaat tcccagttag ttcgtgatga gttagatggt     900
aaacacgatt atcgtgatca cgagttgatt caagatcgtt actcactccg atgccttccc     960
```

```
cagtatttgg ggccaatcgt tgatggaatt tcccagattg ccaaacaaat tgaaatcgaa    1020
atcaactcag tcaccgataa cccactaatt gatgttgata accaagctag ctatcatgga    1080
ggaaatttcc tcggacagta cgtgggtatg ggaatggatc acctgcgtta ctatattggg    1140
ttattggcta aacacctaga tgtgcagatt gccctcctcg cctcaccaga gtttagcaat    1200
ggactaccac catctttatt aggcaaccga gaacgtaaag tcaatatggg actcaaaggt    1260 ctgcaaaatat gcggtaactc aattatgcca ctgttgacct tctatggaaa ttccatcgcc    1320
gatcgctttc ctaccatgc agaacaattt aatcagaaca tcaacagtca aggatacact    1380
tcagcgactc tagcccgccg ttctgtggat atcttccaga attatgtggc gatcgctctg    1440
atgtttggag tccaagctgt tgacctccgc acatataaaa agactggtca ttacgatgca    1500
cgcgcctgtc tatcacctgc aactgagcgc ttatattcag cagtccgcca cgtagttgga    1560
caaaaaccaa cttcagatcg cccatatatt tggaatgata atgagcaagg actggatgag    1620
catattgccc ggatttctgc tgatatcgct gctggtggtg tgattgtgca agcagttcaa    1680
gatatcttac cctgcttgca ttaa                                            1704
```

<210> SEQ ID NO 4
<211> LENGTH: 567
<212> TYPE: PRT
<213> ORGANISM: Anabaena variabilis

<400> SEQUENCE: 4

```
Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240
```

```
Ile Leu Thr Ala Ile Ala Met Gly Val His Ala Leu Asp Ile Gln Ala
                245                 250                 255
Leu Asn Gly Thr Asn Gln Ser Phe His Pro Phe Ile His Asn Ser Lys
            260                 265                 270
Pro His Pro Gly Gln Leu Trp Ala Ala Asp Gln Met Ile Ser Leu Leu
        275                 280                 285
Ala Asn Ser Gln Leu Val Arg Asp Glu Leu Asp Gly Lys His Asp Tyr
    290                 295                 300
Arg Asp His Glu Leu Ile Gln Asp Arg Tyr Ser Leu Arg Cys Leu Pro
305                 310                 315                 320
Gln Tyr Leu Gly Pro Ile Val Asp Gly Ile Ser Gln Ile Ala Lys Gln
                325                 330                 335
Ile Glu Ile Glu Ile Asn Ser Val Thr Asp Asn Pro Leu Ile Asp Val
            340                 345                 350
Asp Asn Gln Ala Ser Tyr His Gly Gly Asn Phe Leu Gly Gln Tyr Val
        355                 360                 365
Gly Met Gly Met Asp His Leu Arg Tyr Tyr Ile Gly Leu Leu Ala Lys
    370                 375                 380
His Leu Asp Val Gln Ile Ala Leu Leu Ala Ser Pro Glu Phe Ser Asn
385                 390                 395                 400
Gly Leu Pro Pro Ser Leu Leu Gly Asn Arg Glu Arg Lys Val Asn Met
                405                 410                 415
Gly Leu Lys Gly Leu Gln Ile Cys Gly Asn Ser Ile Met Pro Leu Leu
            420                 425                 430
Thr Phe Tyr Gly Asn Ser Ile Ala Asp Arg Phe Pro Thr His Ala Glu
        435                 440                 445
Gln Phe Asn Gln Asn Ile Asn Ser Gln Gly Tyr Thr Ser Ala Thr Leu
    450                 455                 460
Ala Arg Arg Ser Val Asp Ile Phe Gln Asn Tyr Val Ala Ile Ala Leu
465                 470                 475                 480
Met Phe Gly Val Gln Ala Val Asp Leu Arg Thr Tyr Lys Lys Thr Gly
                485                 490                 495
His Tyr Asp Ala Arg Ala Cys Leu Ser Pro Ala Thr Glu Arg Leu Tyr
            500                 505                 510
Ser Ala Val Arg His Val Val Gly Gln Lys Pro Thr Ser Asp Arg Pro
        515                 520                 525
Tyr Ile Trp Asn Asp Asn Glu Gln Gly Leu Asp Glu His Ile Ala Arg
    530                 535                 540
Ile Ser Ala Asp Ile Ala Ala Gly Gly Val Ile Val Gln Ala Val Gln
545                 550                 555                 560
Asp Ile Leu Pro Cys Leu His
                565
```

<210> SEQ ID NO 5
<211> LENGTH: 43
<212> TYPE: DNA
<213> ORGANISM: Artificial Sequence
<220> FEATURE:
<223> OTHER INFORMATION: Anabaena variabilis PAL primer to create
      cysteine to serine substitution at position 318 (forward)

<400> SEQUENCE: 5
caagatcgtt actcactccg atcccttccc cagtatttgg ggc          43

<210> SEQ ID NO 6

-continued

```
<211> LENGTH: 43
<212> TYPE: DNA
<213> ORGANISM: Artificial Sequence
<220> FEATURE:
<223> OTHER INFORMATION: Anabaena variabilis PAL primer to create
      cysteine to serine substitution at position 318 (reverse)

<400> SEQUENCE: 6
gccccaaata ctggggaagg gatcggagtg agtaacgatc ttg                             43

<210> SEQ ID NO 7
<211> LENGTH: 567
<212> TYPE: PRT
<213> ORGANISM: Artificial Sequence
<220> FEATURE:
<223> OTHER INFORMATION: Cysteine to serine substitution at position 64
      in Anabaena variabilis PAL

<400> SEQUENCE: 7
```

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Ser
50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
290                 295                 300

-continued

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
            325                 330                 335

Ile Glu Ile Glu Ile Asn Ser Val Thr Asp Asn Pro Leu Ile Asp Val
        340                 345                 350

Asp Asn Gln Ala Ser Tyr His Gly Gly Asn Phe Leu Gly Gln Tyr Val
            355                 360                 365

Gly Met Gly Met Asp His Leu Arg Tyr Tyr Ile Gly Leu Leu Ala Lys
370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
            405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
            435                 440                 445

Gln Phe Asn Gln Asn Ile Asn Ser Gln Gly Tyr Thr Ser Ala Thr Leu
450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
            485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
            515                 520                 525

Tyr Ile Trp Asn Asp Asn Glu Gln Gly Leu Asp Glu His Ile Ala Arg
            530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 8
<211> LENGTH: 567
<212> TYPE: PRT
<213> ORGANISM: Artificial Sequence
<220> FEATURE:
<223> OTHER INFORMATION: Cysteine to serine substitution at position 318
      in Anabaena variabilis PAL

<400> SEQUENCE: 8

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

```
Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
    290                 295                 300

Arg Asp His Glu Leu Ile Gln Asp Arg Tyr Ser Leu Arg Ser Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510
```

-continued

```
Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 9
<211> LENGTH: 567
<212> TYPE: PRT
<213> ORGANISM: Artificial Sequence
<220> FEATURE:
<223> OTHER INFORMATION: Cysteine to serine substitution at position 503
      in Anabaena variabilis PAL

<400> SEQUENCE: 9

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
            85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
            165                 170                 175

Ile Thr Gly Ser Leu Ile Gly Leu Asp Pro Ser Phe Lys Val Asp Phe
        180                 185                 190

Asn Gly Lys Glu Met Asp Ala Pro Thr Ala Leu Arg Gln Leu Asn Leu
        195                 200                 205

Ser Pro Leu Thr Leu Pro Lys Glu Gly Leu Ala Met Met Asn Gly
            210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
290                 295                 300
```

```
Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Ser Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 10
<211> LENGTH: 567
<212> TYPE: PRT
<213> ORGANISM: Artificial Sequence
<220> FEATURE:
<223> OTHER INFORMATION: Cysteine to serine substition at position 565
      in Anabaena variabilis PAL

<400> SEQUENCE: 10

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Gly Asn Gln Lys
                20                  25                  30

Leu Thr Ile Asn Asp Val Ala Arg Val Ala Arg Asn Gly Thr Leu Val
            35                  40                  45

Ser Leu Thr Asn Asn Thr Asp Ile Leu Gln Gly Ile Gln Ala Ser Cys
        50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
```

```
                     85                  90                  95
Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
            115                 120                 125

Ala Asn Ser His Met Arg Gly Ala Ser Gly Ile Arg Leu Glu Leu Ile
            130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
            195                 200                 205

Ser Pro Leu Thr Leu Leu Pro Lys Glu Gly Leu Ala Met Met Asn Gly
            210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
            275                 280                 285

Ala Asn Ser Gln Leu Val Arg Asp Glu Leu Asp Gly Lys His Asp Tyr
            290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
            355                 360                 365

Gly Met Gly Met Asp His Leu Arg Tyr Tyr Ile Gly Leu Leu Ala Lys
            370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
            435                 440                 445

Gln Phe Asn Gln Asn Ile Asn Ser Gln Gly Tyr Thr Ser Ala Thr Leu
            450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510
```

-continued

```
Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Ser Leu His
                565

<210> SEQ ID NO 11
<211> LENGTH: 567
<212> TYPE: PRT
<213> ORGANISM: Artificial Sequence
<220> FEATURE:
<223> OTHER INFORMATION: Cysteine to serine substitutions at positions
      565 and 503 in Anabaena variabilis PAL

<400> SEQUENCE: 11

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
            85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
            115                 120                 125

Ala Asn Ser His Met Arg Gly Ala Ser Gly Ile Arg Leu Glu Leu Ile
        130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
            165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
            195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
            245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
            275                 280                 285

Ala Asn Ser Gln Leu Val Arg Asp Glu Leu Asp Gly Lys His Asp Tyr
```

```
            290                 295                 300
Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Ser Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Ser Leu His
                565

<210> SEQ ID NO 12
<211> LENGTH: 38
<212> TYPE: DNA
<213> ORGANISM: Artificial Sequence
<220> FEATURE:
<223> OTHER INFORMATION: Nostoc punctiforme PAL primer 1 (forward)

<400> SEQUENCE: 12
cactgtcata tgaatataac atctctacaa cagaacat                          38

<210> SEQ ID NO 13
<211> LENGTH: 45
<212> TYPE: DNA
<213> ORGANISM: Artificial Sequence
<220> FEATURE:
<223> OTHER INFORMATION: Nostoc punctiforme PAL primer 2 (reverse)

<400> SEQUENCE: 13
gacagtggcg gccgctcacg ttgactttaa gctcgaaaaa atatg                  45

<210> SEQ ID NO 14
```

```
<211> LENGTH: 38
<212> TYPE: DNA
<213> ORGANISM: Artificial Sequence
<220> FEATURE:
<223> OTHER INFORMATION: Anabaena variabilis PAL primer 1 (forward,
      N-terminal fragment)

<400> SEQUENCE: 14
cactgtgcta gcatgaagac actatctcaa gcacaaag                             38

<210> SEQ ID NO 15
<211> LENGTH: 49
<212> TYPE: DNA
<213> ORGANISM: Artificial Sequence
<220> FEATURE:
<223> OTHER INFORMATION: Anabaena variabilis PAL primer 2 (reverse,
      N-terminal fragment)

<400> SEQUENCE: 15
ggaaatttcc tccatgatag ctggcttggt tatcaacatc aattagtgg                 49

<210> SEQ ID NO 16
<211> LENGTH: 49
<212> TYPE: DNA
<213> ORGANISM: Artificial Sequence
<220> FEATURE:
<223> OTHER INFORMATION: Anabaena variabilis PAL primer 3 (forward,
      C-terminal fragment)

<400> SEQUENCE: 16
ccactaattg atgttgataa ccaagccagc tatcatggag gaaatttcc                 49

<210> SEQ ID NO 17
<211> LENGTH: 41
<212> TYPE: DNA
<213> ORGANISM: Artificial Sequence
<220> FEATURE:
<223> OTHER INFORMATION: Anabaena variabilis PAL primer 4 (reverse,
      C-terminal fragment)

<400> SEQUENCE: 17
cactgtgcgg ccgcttaatg caagcagggt aagatatctt g                        41

<210> SEQ ID NO 18
<211> LENGTH: 35
<212> TYPE: DNA
<213> ORGANISM: Artificial Sequence
<220> FEATURE:
<223> OTHER INFORMATION: Anabaena variabilis PAL forward primer

<400> SEQUENCE: 18
cactgtcata tgaagacact atctcaagca caaag                               35

<210> SEQ ID NO 19
<211> LENGTH: 36
<212> TYPE: DNA
<213> ORGANISM: Artificial Sequence
<220> FEATURE:
<223> OTHER INFORMATION: Anabaena variabilis PAL reverse primer

<400> SEQUENCE: 19
cactgtctcg agatgcaagc agggtaagat atcttg                              36

<210> SEQ ID NO 20
<211> LENGTH: 38
<212> TYPE: DNA
<213> ORGANISM: Artificial Sequence
```

<220> FEATURE:
<223> OTHER INFORMATION: Anabaena variabilis PAL primer to create 5'
      NheI site and delete internal NheI site (forward, N-terminal)

<400> SEQUENCE: 20
cactgtgcta gcatgaagac actatctcaa gcacaaag                          38

<210> SEQ ID NO 21
<211> LENGTH: 49
<212> TYPE: DNA
<213> ORGANISM: Artificial Sequence
<220> FEATURE:
<223> OTHER INFORMATION: Anabaena variabilis PAL primer to create 5'
      NheI site and delete internal NheI site (reverse, N-terminal )

<400> SEQUENCE: 21
ggaaatttcc tccatgatag ctggcttggt tatcaacatc aattagtgg              49

<210> SEQ ID NO 22
<211> LENGTH: 49
<212> TYPE: DNA
<213> ORGANISM: Artificial Sequence
<220> FEATURE:
<223> OTHER INFORMATION: Anabaena variabilis PAL primer to create 5'
      NheI site and delete internal NheI site (forward, C-terminal
      fragment)

<400> SEQUENCE: 22
ccactaattg atgttgataa ccaagccagc tatcatggag gaaatttcc              49

<210> SEQ ID NO 23
<211> LENGTH: 41
<212> TYPE: DNA
<213> ORGANISM: Artificial Sequence
<220> FEATURE:
<223> OTHER INFORMATION: Anabaena variabilis PAL primer to create 5'
      NheI site and delete internal NheI site (reverse, C-terminal
      fragment)

<400> SEQUENCE: 23
acagtggcgg ccgcttaatg caagcagggt aagatatctt g                     41

<210> SEQ ID NO 24
<211> LENGTH: 38
<212> TYPE: DNA
<213> ORGANISM: Artificial Sequence
<220> FEATURE:
<223> OTHER INFORMATION: Anabaena variabilis PAL primer to create 5'
      NheI site and 3' SmaI site (forward)

<400> SEQUENCE: 24
cactgtgaat tcatgaagac actatctcaa gcacaaag                         38

<210> SEQ ID NO 25
<211> LENGTH: 37
<212> TYPE: DNA
<213> ORGANISM: Artificial Sequence
<220> FEATURE:
<223> OTHER INFORMATION: Anabaena variabilis PAL primer to create 5'
      NheI site and 3' SmaI site (reverse)

<400> SEQUENCE: 25
cactgtcccg ggttaatgca agcagggtaa gatatct                          37

<210> SEQ ID NO 26
<211> LENGTH: 41
<212> TYPE: DNA

-continued

```
<213> ORGANISM: Artificial Sequence
<220> FEATURE:
<223> OTHER INFORMATION: Anabaena variabilis PAL primer to create
      cysteine to serine substitution at position 503 (forward)

<400> SEQUENCE: 26
gtcattacga tgcacgcgcc tctctatcac ctgcaactga g                    41

<210> SEQ ID NO 27
<211> LENGTH: 41
<212> TYPE: DNA
<213> ORGANISM: Artificial Sequence
<220> FEATURE:
<223> OTHER INFORMATION: Anabaena variabilis PAL primer to create
      cysteine to serine substitution at position 503 (reverse)

<400> SEQUENCE: 27
ctcagttgca ggtgatagag aggcgcgtgc atcgtaatga c                    41

<210> SEQ ID NO 28
<211> LENGTH: 42
<212> TYPE: DNA
<213> ORGANISM: Artificial Sequence
<220> FEATURE:
<223> OTHER INFORMATION: Anabaena variabilis PAL primer to create
      cysteine to serine substitution at position 565 (forward)

<400> SEQUENCE: 28
cagttcaaga tatcttaccc tccttgcatt aacccgggct gc                   42

<210> SEQ ID NO 29
<211> LENGTH: 42
<212> TYPE: DNA
<213> ORGANISM: Artificial Sequence
<220> FEATURE:
<223> OTHER INFORMATION: Anabaena variabilis PAL primer to create
      cysteine to serine substitution at position 565 (reverse)

<400> SEQUENCE: 29
gcagcccggg ttaatgcaag gagggtaaga tatcttgaac tg                   42

<210> SEQ ID NO 30
<211> LENGTH: 44
<212> TYPE: DNA
<213> ORGANISM: Artificial Sequence
<220> FEATURE:
<223> OTHER INFORMATION: Anabaena variabilis PAL primer to create
      cysteine to serine substitution at position 64 (forward)

<400> SEQUENCE: 30
gcagggtatt caggcatctt ctgattacat taataatgct gttg                 44

<210> SEQ ID NO 31
<211> LENGTH: 44
<212> TYPE: DNA
<213> ORGANISM: Artificial Sequence
<220> FEATURE:
<223> OTHER INFORMATION: Anabaena variabilis PAL primer to create
      cysteine to serine substitution at position 64 (reverse)

<400> SEQUENCE: 31
caacagcatt attaatgtaa tcagaagatg cctgaatacc ctgc                 44
```